(12) United States Patent
Chang et al.

(10) Patent No.: US 9,192,664 B2
(45) Date of Patent: Nov. 24, 2015

(54) THERAPEUTIC USE OF ANTI-CD22 ANTIBODIES FOR INDUCING TROGOCYTOSIS

(71) Applicant: Immunomedics, Inc., Morris Plains, NJ (US)

(72) Inventors: Chien-Hsing Chang, Downingtown, PA (US); David M. Goldenberg, Mendham, NJ (US); Hans J. Hansen, Picayune, MS (US); Edmund A. Rossi, Woodland Park, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 13/693,476

(22) Filed: Dec. 4, 2012

(65) Prior Publication Data

US 2013/0142787 A1 Jun. 6, 2013

Related U.S. Application Data

(60) Provisional application No. 61/566,828, filed on Dec. 5, 2011, provisional application No. 61/609,075, filed on Mar. 9, 2012, provisional application No. 61/682,508, filed on Aug. 13, 2012, provisional application No. 61/718,226, filed on Oct. 25, 2012.

(51) Int. Cl.
| | |
|---|---|
| *G01N 33/53* | (2006.01) |
| *A61K 39/395* | (2006.01) |
| *A61K 45/06* | (2006.01) |
| *C07K 16/28* | (2006.01) |
| *C07K 16/00* | (2006.01) |
| *A61K 39/00* | (2006.01) |

(52) U.S. Cl.
CPC ............. *A61K 39/3955* (2013.01); *A61K 45/06* (2013.01); *C07K 16/2803* (2013.01); *A61K 2039/505* (2013.01); *C07K 2317/54* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| | | |
|---|---|---|
| 4,036,945 A | 7/1977 | Haber |
| 4,046,722 A | 9/1977 | Rowland |
| 4,331,647 A | 5/1982 | Goldenberg |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Howthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |

(Continued)

FOREIGN PATENT DOCUMENTS

| | | |
|---|---|---|
| CA | 2752553 | 8/2003 |
| CA | 2835591 | 7/2004 |

(Continued)

OTHER PUBLICATIONS

Youinou et al. Autoimmunity Reviews 2006 5:215-221.*
Rossi et al. Blood 2009, 113:6161-6171.*
Williams et al. The Journal of Immunology, 2006, 177:7435-7443.*
Goldenberg et al. and Tedder et al. Arthritis & Rheumatism 2006 54;7:2344-2345.*
Steinfeld et al. (Arthritis Research & Therapy 2006, 8:R129.*
Motta et al. (Clinical and Developmental Immunology 2010, pp. 1-14.*

(Continued)

*Primary Examiner* — Chun Dahle
(74) *Attorney, Agent, or Firm* — Richard A. Nakashima

(57) ABSTRACT

Disclosed are methods and compositions of anti-B cell antibodies, preferably anti-CD22 antibodies, for diagnosis, prognosis and therapy of B-cell associated diseases, such as B-cell malignancies, autoimmune disease and immune dysfunction disease. In certain embodiments, trogocytosis induced by anti-B cell antibodies may determine antibody efficacy, disease responsiveness and prognosis of therapeutic intervention. In other embodiments, optimal dosages of therapeutic antibody may be selected by monitoring the degree of trogocytosis induced by anti-B cell antibodies. Other characteristics of anti-B-cell antibodies that may be monitored include inducing phosphorylation of CD22, CD79a and CD79b; inducing translocation of CD22, CD79a and CD79b to lipid rafts; inducing caspase-dependent apoptosis; increasing pLyn, pERKs and pJNKs; decreasing constitutively-active p38; or inducing mitochondrial membrane depolarization, generation of reactive oxygen species, upregulation of pro-apoptotic Bax and downregulation of anti-apoptotic Bcl-xl, Mcl-1 and Bcl-2.

7 Claims, 38 Drawing Sheets

(56) References Cited

U.S. PATENT DOCUMENTS

| | | | |
|---|---|---|---|
| 5,716,595 A | 2/1998 | Goldenberg | |
| 5,736,119 A | 4/1998 | Goldenberg et al. | |
| 5,750,105 A | 5/1998 | Newman et al. | |
| 5,776,456 A | 7/1998 | Anderson et al. | |
| 5,789,554 A | 8/1998 | Leung et al. | |
| 5,792,845 A | 8/1998 | O'Reilly et al. | |
| 5,795,967 A | 8/1998 | Aggarwal et al. | |
| 5,798,554 A | 8/1998 | Grimaldi et al. | |
| 5,874,540 A | 2/1999 | Hansen et al. | |
| 5,922,302 A | 7/1999 | Goldenberg et al. | |
| 6,051,228 A | 4/2000 | Aruffo et al. | |
| 6,051,230 A | 4/2000 | Thorpe et al. | |
| 6,077,499 A | 6/2000 | Griffiths et al. | |
| 6,096,289 A | 8/2000 | Goldenberg | |
| 6,165,440 A | 12/2000 | Esenaliev | |
| 6,183,744 B1 | 2/2001 | Goldenberg | |
| 6,187,287 B1 | 2/2001 | Leung et al. | |
| 6,254,868 B1 | 7/2001 | Leung et al. | |
| 6,306,393 B1 | 10/2001 | Goldenberg | |
| 6,331,175 B1 | 12/2001 | Goldenberg | |
| 6,379,698 B1 | 4/2002 | Leamon | |
| 6,387,350 B2 | 5/2002 | Goldenberg | |
| 6,395,276 B1 | 5/2002 | Rybak et al. | |
| 6,530,944 B2 | 3/2003 | West et al. | |
| 6,562,318 B1 | 5/2003 | Filler | |
| 6,653,104 B2 | 11/2003 | Goldenberg | |
| 7,018,809 B1 | 3/2006 | Carter | |
| 7,074,403 B1 | 7/2006 | Goldenberg et al. | |
| 7,387,779 B2 | 6/2008 | Kalluri | |
| 7,772,373 B2 | 8/2010 | Hansen et al. | |
| 7,820,161 B1 | 10/2010 | Curd et al. | |
| 7,910,103 B2 | 3/2011 | Goldenberg | |
| 7,931,903 B2 | 4/2011 | Hansen et al. | |
| 2002/0018749 A1 | 2/2002 | Hudson et al. | |
| 2004/0076683 A1 | 4/2004 | Hoarau et al. | |
| 2005/0079514 A1 | 4/2005 | Hsing-Chang et al. | |
| 2010/0330089 A1 | 12/2010 | Damle et al. | |
| 2011/0256053 A1 | 10/2011 | Chang et al. | |

FOREIGN PATENT DOCUMENTS

| | | |
|---|---|---|
| EP | 0332865 | 9/1989 |
| EP | 0510949 | 10/1992 |
| EP | 0739980 | * 10/1996 |
| EP | 1640717 | 3/2006 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 00/74718 | 12/2000 |
| WO | 2009012268 | 1/2009 |
| WO | 2010011697 | 1/2010 |

OTHER PUBLICATIONS

Longo, D. L. "Immunotherapy for non-Hodgkin's lymphoma", Curr. Opin. Oncol. 8(5):353-9 (1996).

Losman et al., "Baboon anti-idiotype antibodies mimic a carcinoembryonic antigen epitope", Int J Cancer. Aug. 15, 1990;46(2):310-4.

Lundberg, B. "Preparation of drug-carrier emulsions stabilized with phosphatidylcholine-surfactant mixtures", J. Pharm. Sci. 83(1):72-5 (1994).

Lundberg et al., "Submicron lipid emulsions containing amphipathic polyethylene glycol for use as drug-carriers with prolonged circulation time", Int. J. Pharm. 134:119-127 (1996).

Lundberg et al., "Conjugation of an anti-B-cell lymphoma monoclonal antibody, LL2, to long-circulating drug-carrier lipid emulsions", J. Pharm. Pharmacol. 51(10):1099-105 (1999).

Mack et al., "A small bispecific antibody construct expressed as a functional single-chain molecule with high tumor cell cytotoxicity", Proc. Natl. Acad. Sci. USA 92:7021-7025 (1995).

Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).

Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.

Mason et al., "Value of monoclonal anti-CD22 (p135) antibodies for the detection of normal and neoplastic B lymphoid cells", Blood. Mar. 1987;69(3):836-40.

Mills et al., "Diagnostic imaging of non-Hodgkin's lymphoma with anti-lymphomas antibody labeled with Tc-99m", Proc Am Assoc Cancer Res 1993; 34:479, Abstract #2857.

Mole S. E., "Epitope Mapping", Methods in Molecular Biology, vol. 10: Immunochemical Protocols, Manson (Ed.), Humana Press, Inc. (1992).

Morrison et al., "Chimeric human antibody molecules: mouse antigen-binding domains with human constant region domains", Proc Natl Acad Sci USA Nov. 1984;81(21):6851-5.

Murthy et al., "Lymphoma imaging with a new technetium-99m labelled antibody, LL2", Eur J Nucl Med. 1992;19(6):394-401.

Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).

Orlandi et al., "Cloning immunoglobulin variable domains for expression by the polymerase chain reaction", Proc. Natl. Acad. Sci. USA 86:3833-3837 (1989).

Pastan et al., "Immunotoxins", Cell 47:641-648 (1986).

Pawlak-Byczkowska et al., "Two new monoclonal antibodies, EPB-1 and EPB-2, reactive with human lymphoma", Cancer Res. 49(16):4568-77 (1989).

Perrota et al., "Response of chronic relapsing ITP of 10 years duration to Rituximab", Blood, vol. 92(10 Suppl.), p. 88b, 1998, Abstract# 3360.

Press et al., "Radiolabeled-antibody therapy of B-cell lymphoma with autologous bone marrow support", N. Engl. J. Med. 329(17):1219-24 (1993).

Press et al., "Phase II trial of 131I-B1 (anti-CD20) antibody therapy with autologous stem cell transplantation for relapsed B cell lymphomas", Lancet 346:336-40 (1995).

Press et al., "Prospects for the management of non-Hodgkin's lymphomas with monoclonal antibodies and immunoconjugates", Cancer J. Sci. Am. 4(Suppl 2):S19-26 (1998).

Protheroe et al., "Remission of inflammatory arthropathy in association with anti-CD20 therapy for non-Hodgkin's lymphoma", Rheumatology (Oxford) 38(11):1150-2 (1999).

Qu et al., "Carbohydrates engineered at antibody constant domains can be used for site-specific conjugation of drugs and chelates", J. Immunol. Methods 213(2):131-44 (1998).

Qu et al., "Internalization and cytotoxic effects of a humanized anti-CD74 antibody, LL1", Proc Am Assoc Cancer Res 2002;43:255, Abstract # 1269.

Queen et al., "A humanized antibody that binds to the interleukin 2 receptor", Proc Natl Acad Sci U S A. Dec. 1989;86(24):10029-33.

Renner et al., "Monoclonal antibodies in the treatment of non-Hodgkin's lymphoma: recent results and future prospects", Leukemia 11(Suppl 2):S55-9 (1997).

Riechmann et al., "Reshaping human antibodies for therapy", Nature 332(6162):323-7 (1988).

Roche et al., "Cell surface HLA-DR-invariant chain complexes are targeted to endosomes by rapid internalization", Proc Natl Acad Sci U S A. Sep. 15, 1993;90(18):8581-5.

(56) References Cited

OTHER PUBLICATIONS

Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79 (6):1979-83 (1982).
Saltzman et al., "Transport rates of proteins in porous materials with known microgeometry", Biophys. J. 55 (1):163-71 (1989).
Sandhu, J. S., "Protein engineering of antibodies", Crit. Rev. Biotechnol. 12(5-6):437-62 (1992).
Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sharkey et al., "Epratuzumab-SN-38: A New Antibody-Drug Conjugate for the Therapy of Hematologic Malignancies", Mol Cancer Ther. Dec. 16, 2011 [Epub ahead of print].
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B-B cell interactions", J Exp Med. Jan. 1, 1991;173(1):137-46.
Wilson et al., "Genomic structure and chromosomal mapping of the human CD22 gene", J Immunol. Jun. 1, 1993;150(11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.
US 6,558,648, May 2003, Griffiths et al. (Withdrawn).
Aozasa et al., "The occurrence of monocytoid B-lymphocytes in autoimmune disorders", Mod Pathol. Mar. 1993;6(2):121-4.
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Beers et al., The Merck Manual of Diagnosis and Therapy, Ch. 180, p. 1474-1476; 17th Ed., Whitehouse Station, NJ, Merck Research Labs (1999).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer. Feb. 1, 1994;73(3 Suppl):896-9.

Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid A monoclonal antibodies bind to human B cells and the i antigen on cord red blood cells", J Immunol. Nov. 1, 1993;151(9):5011-21.
Brozek et al., "Anti-DR antibodies inhibit in vitro production of human rheumatoid factor", J Clin Lab Immunol. Mar. 1990;31(3):105-9.
Carter et al., "Humanization of an anti-p185HER2 antibody for human cancer therapy", Proc. Natl. Acad. Sci. USA 89(10):4285-9 (1992).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63 (1997).
Dillman et al., "Antibodies as cytotoxic therapy", J Clin Oncol. Jul. 1994;12(7):1497-515.
Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).
Ellis et al., "Engineered anti-CD38 monoclonal antibodies for immunotherapy of multiple myeloma", J Immunol. Jul. 15, 1995;155(2):925-37.
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20(7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M. "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and in Combination with Veltuzumab, a Humanized Anti-CD20 MAb", Blood (ASH Annual Meeting Abstracts) 2010 116: Abstract 3941.
Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human Ig heavy and light chain YACs", Nature Genetics 7:13-21 (1994).
Grossbard et al., "Monoclonal antibody-based therapies of leukemia and lymphoma", Blood. Aug. 15, 1992;80(4):863-78.
Gussow et al., "Humanization of monoclonal antibodies", Methods Enzymol. 1991;203:99-121.
Hansen et al., "Internalization and catabolism of radiolabelled antibodies to the MHC class-II invariant chain by B-cell lymphomas", Biochem. J. 1996, 320:293-300.
Hashida et al., "More useful maleimide compounds for the conjugation of Fab' to horseradish peroxidase through thiol groups in the hinge", J Appl Biochem. Feb.-Apr. 1984;6(1-2):56-63.
Hekman et al. "Initial experience with treatment of human B cell lymphoma with anti-CD19 monoclonal antibody", Cancer Immunol. Immunother. 1991;32(6):364-72.

(56) References Cited

OTHER PUBLICATIONS

Hess et al., "Specificity of effector T lymphocytes in autologous graft-versus-host disease: role of the major histocompatibility complex class II invariant chain peptide", Blood 89(6):2203-9 (1997).

Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.

Imuran patient information leaflet, GlaxoSmithKline 7076598/5093, Oct. 2004.

Inaoki et al., "CD19-regulated signaling thresholds control peripheral tolerance and autoantibody production in B lymphocytes", J Exp Med. Dec. 1, 1997;186(11):1923-31.

Jones et al., "Replacing the complementarity-determining regions in a human antibody with those from a mouse" Nature 321(6069):522-5 (1986).

Juweid et al., "99Tcm-LL1: a potential new bone marrow imaging agent", Nucl. Med. Commun. 18(2):142-8 (1997).

Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).

Kaminski et al., "Radioimmunotherapy of B-cell lymphoma with [131I]anti-B1 (anti-CD20) antibody", N. Engl. J. Med. 329(7):459-65 (1993).

Kiener et al., "Stimulation of CD40 with purified soluble gp39 induces proinflammatory responses in human monocytes", J Immunol. Nov. 15, 1995;155(10):4917-25.

Kiesel et al., "Removal of cells from a malignant B-cell line from bone marrow with immunomagnetic beads and with complement and immunoglobulin switch variant mediated cytolysis", Leuk. Res. 11(12):1119-25 (1987).

Kohler et al., "Continuous cultures of fused cells secreting antibody of predefined specificity", Nature 256:495-7 (1975).

Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).

Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).

Leung et al., "Chimerization and humanization of a B-cell Lymphoma specific antibody, LL2", Proc Am Assoc Cancer Res 1993; 34:481, Abstr #2872.

Leung et al., "Chimerization of LL2, a Rapidly Internalizing Antibody Specific for B Cell Lymphoma", Hybridoma 13(6):469-476 (1994).

Leung et al., "Construction and characterization of a humanized, internalizing, b-cell (CD22)-specific, leukemia/lymphma antibody, LL2", Mol. Immunol. 32(17/18):1413-1427 (1995).

Levine et al., "IgM antibody-related polyneuropathies: B-cell depletion chemotherapy using Rituximab", Neurology 52(8):1701-4 (1999).

Li et al., "The epitope specificity and tissue reactivity of four murine monoclonal anti-CD22 antibodies", Cell Immunol. 118(1):85-99 (1989).

Lonberg et al., "Antigen-specific human antibodies from mice comprising four distinct genetic modifications", Nature 368:856-9 (1994).

Beum et al., "Binding of rituximab, trastuzumab, cetuximab, or mAb T101 to cancer cells promotes trogocytosis mediated by THP-1 cells and monocytes", J Immunol. Dec. 1, 2008:181(11):8120-32.

Hudrisier et al., "Capture of target cell membrane components via trogocytosis is triggered by a selected set of surface molecules on T or B cells", J Immunol. Mar. 15, 2007;178(6):3637-47.

International Search Report from PCT/US12/67740, filed Dec. 4, 2012. Date of mailing Apr. 5, 2013.

Rossi et al., "Trogocytosis of multiple B-cell surface markers by CD22 targeting with epratuzumab", Blood. Oct. 24, 2013;122(17):3020-9.

Taylor, R., "Gnawing at Metchnikoff's paradigm", Blood. Oct. 24, 2013;122(17):2922-4.

* cited by examiner

PBMC

PBMC-Δ Monocytes

Monocytes

A. CD14++

B. CD14+CD16+ hLL2 in the Anti-IgM potency assay induces phosphorylation of CD22, CD79a and CD79b.

hLL2 along with anti-IgM induces cap formation in Daudi (1-1) cells hLL2* on protein A beads induces colocalization of CD22 and IgM receptors in Daudi (1-1) cells

THERAPEUTIC USE OF ANTI-CD22 ANTIBODIES FOR INDUCING TROGOCYTOSIS

RELATED APPLICATIONS

The present application claims the benefit under 35 U.S.C. 119(e) of Provisional U.S. Patent Application Ser. Nos. 61/566,828, filed Dec. 5, 2011; 61/609,075, filed Mar. 9, 2012; 61/682,508, filed Aug. 13, 2012; and 61/718,226, filed Oct. 25, 2012, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 29, 2012, is named IMM337US1.txt and is 52,688 bytes in size.

FIELD OF THE INVENTION

The present invention concerns compositions and methods of use of antibodies against B-cell surface markers, in particular, CD19, CD20, and CD22. Preferably, the antibody is an anti-CD22 antibody. More preferably, the anti-CD22 antibody induces trogocytosis of multiple surface markers, which include, but are not limited to, CD19, CD20, CD21, CD22 and/or CD79b on normal, lupus, and malignant B cells (donor cells) via leukocytes, including monocytes, NK cells and granulocytes (recipient cells). Most preferably, the antibody efficacy, disease cell responsiveness and/or prognosis for disease progression are a function of trogocytosis induced by such antibodies. The trogocytosis-inducing antibody may be used alone, or in combination with other agents, which include one or more different antibodies that may or may not have trogocytosis-inducing activity. Where a combination of two antibodies is desirable, a bispecific antibody derived from the two antibodies of interest may be used in lieu of a combination of such antibodies. Bispecific antibodies are preferred to administration of combinations of separate antibodies, due to cost and convenience. However, where combinations of separate antibodies provide improved safety or efficacy, the combination may be utilized. One preferred form of the bispecific antibody is a hexavalent antibody (HexAb) that is made as a DOCK-AND-LOCK™ complex. Further, a bispecific antibody capable of bridging the donor and recipient cells may not require the presence of Fc for trogocytosis. The compositions and methods are of use in therapy and/or detection, diagnosis or prognosis of various disease states, including but not limited to autoimmune diseases, immune dysfunction diseases and cancers.

BACKGROUND

Trogocytosis (also referred to as shaving in the literature) is a process by which transfer of membrane-bound proteins and membrane components occur between two different types of live cells associated to form an immunological synapse. As a result, the membrane-bound proteins and membrane components are transferred from the donor cells to the recipient cells. Both unidirectional and bidirectional trogocytosis between the two interacting cells may occur. One prominent example of trogocytosis is the extraction of surface antigens from antigen-presenting cells (APCs) by T cells (Joly & Hudrisier, 2003, Nat Immunol 4:85). The process involves transfer of plasma membrane fragments from the APC to the lymphocyte (Joly & Hudrisier, 2003). Intercellular transfer of T cell surface molecules to APCs has also been reported (Nolte-'t Hoen et al, 2004, Eur J Immunol 34: 3115-25; Busch et al 2008, J Immunol 181: 3965-73) via mechanisms that may include trogocytosis, exosomes and ectodomain shedding (Busch et al 2008, ibid). Trogocytosis can also occur between natural killer (NK) cells and tumors and can convert activated NK cells into suppressor cells, via uptake of the immunosuppressive HLA-G molecule, which protects the tumor cells from cytolysis (Caumartin et al., 2007, EMBO J. 26:423-30). CD4+ and CD8+ T cells can, respectively, acquire MHC Class II and MHC Class I molecules from APCs in an antigen-specific manner (Caumartin et al., 2007). Trogocytosis of HLA-DR, CD80 and HLA-G1 from APCs to T cells has been shown to occur in humans (Caumartin et al., 2007). After acquiring HLA-DR and CD80, T cells stimulated resting T cells in an antigen-specific manner, acting as APCs themselves (Caumartin et al., 2007). More generally, trogocytosis may act to regulate immune system responsiveness to disease-associated antigens and can either stimulate or suppress immune response (Ahmed et al., 2008, Cell Mol Immunol 5:261-69).

The effects of trogocytosis on therapeutic antibody responsiveness and the induction of trogocytosis by therapeutic antibodies remain poorly understood. It has been suggested that induction of trogocytosis by excess amounts of rituximab may result in removal of rituximab-CD20 complexes from tumor cell surfaces by monocytes, producing antigenic modulation (shaving) and rituximab-resistant tumor cells (Beum et al., 2006, J Immunol 176:2600-8). Thus, use of lower, more frequent doses of rituximab to reduce antigen shaving has been suggested (Beum et al., 2006). Transfer of rituximab/CD20 complexes to monocytes is mediated by FcγR and it has also been suggested that polymorphisms in FcγRII and FcγRIII may affect the degree of antibody-induced shaving and predict responsiveness to antibody therapy (Beum et al., 2006). In this regard, use of antibodies or other inhibitors that block trogocytosis may enhance efficacy and reduce tumor cell escape from cytotoxicity (Beum et al., 2006). On the other hand, the functional consequences of antibody-mediated trogocytosis to confer therapeutic benefits are less explored.

A need exists in the art for a better understanding of the induction of trogocytosis by therapeutic antibodies, the effect of trogocytosis on antigen shaving, and the effects of trogocytosis and shaving on therapeutic efficacy, target cell susceptibility, and immune system responses in various disease states.

SUMMARY

The present invention concerns compositions and methods of use of antibodies against B-cell surface markers, such as CD19, CD20, CD22 and/or CD79b. Preferably, the antibody is an anti-CD22 antibody. More preferably, the anti-CD22 antibody induces trogocytosis of multiple surface markers, which include, but are not limited to, CD19, CD21, CD20, CD22 and CD79b on normal, lupus, and malignant B cells via monocytes, NK cells and granulocytes. Most preferably, the anti-CD22 antibody displays little or negligible direct cytotoxicity to normal B cells based on an in vitro cell proliferation assay that shows less than 20% growth inhibition when compared with untreated control, yet reduces CD19, CD21, CD20, CD22, and CD79b to 20% or more of the untreated control via trogocytosis in the presence of peripheral blood mononuclear cells (PBMCs) or purified FcγR-positive cells, such as NK cells, monocytes and granulocytes. One example of a preferred anti-CD22 antibody is epratuzumab, which induces trogocytosis without incurring direct cytotoxicity to B cells, thus providing an unexpected and substantial advantage in treating autoimmune diseases, such as systemic lupus erythematosus (SLE), ANCA-associated vasculitides, and other autoimmune diseases.

In certain embodiments, administration of an antibody against a selective B cell marker, such as an anti-CD22 antibody, induces trogocytosis in B cells, resulting in decreased levels of CD19, CD20, CD21, CD22 and CD79b on the surface of affected B cells. The reduction in these regulators of antigen-specific B-cell receptor (BCR), particularly CD19, inhibits B cell activation in response to T cell-dependent antigens and has a therapeutic effect on autoimmune and immune dysfunction diseases, which are mediated at least in part by B cell activation. In certain alternative embodiments, an affibody or fynomer fused to a human Fc may be used in place of an antibody.

In a preferred embodiment, the efficacy of anti-B cell antibodies for therapeutic use in autoimmune and/or immune dysfunction diseases is predicted by trogocytosis-mediated decrease in the levels of BCR regulators on the cell surface, particularly that of CD19. Efficacy of anti-B-cell antibodies, such as anti-CD22 antibodies, for therapeutic use in specific autoimmune and/or immune dysfunction diseases may be predicted by measuring the extent of trogocytosis of cell surface CD19 in B cells. The method may involve obtaining a sample of B cells from an individual with autoimmune or immune dysfunction disease, exposing the B cells to an anti-B cell (particularly anti-CD22) antibody, measuring the levels of CD19 in the B cells, and predicting the efficacy of the anti-B cell antibody for disease therapy. Alternatively, the method may involve administering the antibody to a subject and monitoring the level of trogocytosis and/or antigen shaving. In other alternative embodiments, the effect of anti-B cell antibody on inducing trogocytosis of CD19 may be used to predict the susceptibility of the diseased cell to antibody therapy and/or the prognosis of the individual with the disease. In still other embodiments, use of additional predictive factors such as FcγR polymorphisms may be incorporated into the method. The skilled artisan will realize that the same compositions and methods may be of use to provide a prognosis of autoimmune or immune dysfunction disease progression and/or to select an optimum dosage of anti-B cell antibody to administer to a patient with autoimmune and/or immune dysfunction diseases, including but not limited to systemic lupus erythematosus and ANCA-associated vasculitides.

Exemplary autoimmune or immune dysfunction diseases include acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, fibrosing alveolitis, graft-versus-host disease (GVHD), organ transplant rejection, sepsis, septicemia and inflammation.

In another embodiment, trogocytosis and/or antigen shaving may be utilized to select an optimal dosage of anti-B cell antibody, such as anti-CD22 antibody, to be administered to a subject with a malignancy, preferably a B-cell malignancy, such as non-Hodgkin's lymphoma, B-cell acute and chronic lymphoid leukemias, Burkitt lymphoma, Hodgkin's lymphoma, hairy cell leukemia, multiple myeloma and Waldenstrom's macroglobulinemia. Either in vitro or in vivo analysis may be performed. For example, a sample of whole blood or PBMCs may be obtained from a patient with a B-cell malignancy and incubated with different concentrations of anti-B cell antibody, such as anti-CD22 antibody. Dose-response curves may be constructed based on evidence of trogocytosis and/or antigen shaving from B cells. For example, relative cell surface expression levels of CD19, CD20, CD21, CD22 and/or CD79b may be determined by standard assays, such as flow cytometry using fluorescence labeled antibodies. Depending on the disease to be treated, the optimum concentration of antibody to administer to the patient may be selected to either maximize or minimize trogocytosis and/or antigen shaving. The skilled artisan will realize that, for example, selection of an optimal dosage of anti-CD22 antibody to administer may preferably involve monitoring of relative cell surface expression of CD22. Selection of optimal dosage of anti-CD20 antibody may preferably involve monitoring of relative cell surface expression of CD20. However, the method is not limiting and monitoring of surrogate antigens or combinations of antigens may provide a preferred result. For example, monitoring relative cell surface expression of CD22 may in some cases predict optimal levels of anti-CD19, anti-CD20, anti-CD21 or anti-CD79b antibody to administer, or vice-versa. The skilled artisan will realize that the same methods and compositions may be used to determine the efficacy of an anti-B cell antibody against a B-cell malignancy, the prognosis of a B-cell malignancy, and/or the susceptibility of a malignant B cell to anti-B cell antibody.

Antibodies against B-cell surface proteins, such as CD19, CD20, CD21, CD22 and/or CD79b, are known in the art and any such known antibody might be used in the claimed compositions and methods. An exemplary anti-CD20 antibody is hA20 (veltuzumab), disclosed for example in U.S. Pat. No. 7,251,164, the Examples section of which is incorporated herein by reference. Other known anti-CD20 antibodies of potential use include, but are not limited to, rituximab (Genentech, South San Francisco, Calif.), GA101 (obinutuzumab; RO5072759, Roche, Basle, Switzerland), ofatumumab (GlaxoSmithKline, London, England), ocrelizumab (Roche, Nutley, N.J.), AME-133v (ocaratuzumab, MENTRIK Biotech, Dallas, Tex.), ibritumomab (Spectrum Pharmaceuticals, Irvine, Calif.) and PRO131921 (Genentech, South San Francisco, Calif.). An exemplary anti-CD19 antibody is hA19, disclosed for example in U.S. Pat. No. 7,109,304, the Examples section of which is incorporated herein by reference. Other known anti-CD19 antibodies of potential use include, but are not limited to, XmAb5574 (Xencor, Monrovia, Calif.), 5F3 (OriGene, Rockville, Md.), 4G7 (Pierce, Rockford, Ill.), 2E2 (Pierce, Rockford, Ill.), 1G9 (Pierce, Rockford, Ill.), LT19 (Santa Cruz Biotechnology, Santa Cruz, Calif.) and HD37 (Santa Cruz Biotechnology, Santa Cruz, Calif.). An exemplary anti-CD22 antibody is hLL2 (epratuzumab), disclosed for example in U.S. Pat. No. 7,074,403, the Examples section of which is incorporated herein by reference. Other known anti-CD22 antibodies of potential use include, but are not limited to, inotuzumab (Pfizer, Groton, Conn.), CAT-3888 (Cambridge Antibody Technology Group, Cambridge, England), CAT-8015 (Cambridge Antibody Technology Group, Cambridge, England), HB22.7 (Duke University, Durham, N.C.) and RFB4 (e.g., Invitrogen, Grand Island, N.Y.; Santa Cruz Biotechnology, Santa Cruz, Calif.). Exemplary anti-CD21 antibodies of potential use include, but are not limited to, LS-B7297 (LSBio, Seattle, Wash.), HB5 (eBioscience, San Diego, Calif.), A-3 (Santa Cruz Biotechnology, Santa Cruz, Calif.), D-19 (Santa Cruz Biotechnology, Santa Cruz, Calif.), Bly4 (Santa Cruz Biotechnology, Santa Cruz, Calif.), 1F8 (Abcam, Cambridge, Mass.) and Bu32 (BioLegend, San Diego, Calif.). Exemplary anti-CD79b antibodies of potential use include, but are not limited to, B29 (LSBio, Seattle, Wash.), 3A2-2E7 (LSBio, Seattle, Seattle, Wash.), CD3-1 (eBioscience, San Diego, Calif.) and SN8 (Santa Cruz Biotechnology, Santa Cruz, Calif.). Many such antibodies are publicly known and/or commercially available and any such known antibody may be utilized.

An antibody of use may be chimeric, humanized or human. The use of chimeric antibodies is preferred to the parent murine antibodies because they possess human antibody constant region sequences and therefore do not elicit as strong a human anti-mouse antibody (HAMA) response as murine antibodies. The use of humanized antibodies is even more preferred, in order to further reduce the possibility of inducing a HAMA reaction. Techniques for humanization of murine antibodies by replacing murine framework and constant region sequences with corresponding human antibody framework and constant region sequences are well known in the art and have been applied to numerous murine anti-cancer antibodies. Antibody humanization may also involve the substitution of one or more human framework amino acid residues with the corresponding residues from the parent murine framework region sequences. As discussed below, techniques for production of human antibodies are also well known.

The antibody may also be multivalent, or multivalent and multispecific. The antibody may include human constant regions of IgG1, IgG2, IgG3, or IgG4.

In certain embodiments, one or more anti-B-cell antibodies may be administered to a patient as part of a combination of antibodies. The antibodies may bind to different epitopes of the same antigen or to different antigens. Preferably, the antigens are selected from the group consisting of BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, CD56, CCD57, CD59, CD64, CD71, CD79a, CD79b, CD117, CD138, FMC-7 and HLA-DR. However, antibodies against other antigens of use for therapy of cancer, autoimmune diseases or immune dysfunction diseases are known in the art, as discussed below, and antibodies against any such disease-associated antigen known in the art may be utilized.

In more preferred embodiments, the allotype of the antibody may be selected to minimize host immunogenic response to the administered antibody, as discussed in more detail below. A preferred allotype is a non-G1m1 allotype (nG1m1), such as G1m3, G1m3,1, G1m3,2 or G1m3,1,2. The non-G1m1 allotype is preferred for decreased antibody immunoreactivity. Surprisingly, repeated subcutaneous administration of concentrated nG1m1 antibody was not found to induce significant immune response, despite the enhanced immunogenicity of subcutaneous administration.

BRIEF DESCRIPTION OF THE DRAWINGS

The following drawings are provided to illustrate preferred embodiments of the invention. However, the claimed subject matter is in no way limited by the illustrative embodiments disclosed in the drawings.

DETAILED DESCRIPTION

Definitions

Figure 1:
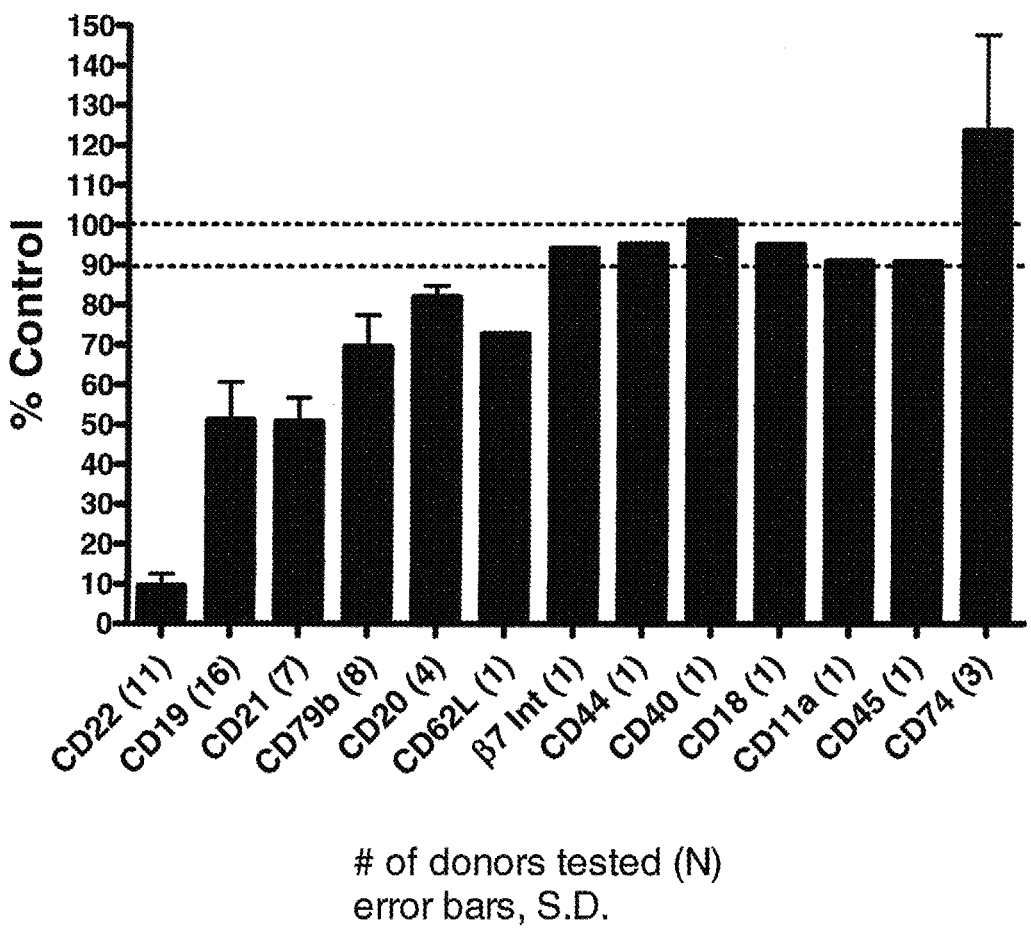
FIG. 1. Epratuzumab-induced reduction of select surface antigens on normal B cells. Fresh PBMCs isolated from the blood of healthy donors were treated overnight with 10 µg/mL epratuzumab or a non-binding isotype control mAb (hMN-14) and the relative surface levels of selected proteins on B cells were measured by flow cytometry. The effect of epratuzumab on 13 different B cell antigens was surveyed. The number of donors evaluated for each specific antigen is indicated in parentheses. The % mean fluorescence intensity of the isotype control treatment is shown. Error bars, Std. Dev.

The following definitions are provided to facilitate understanding of the disclosure herein. Where a term is not specifically defined, it is used in accordance with its plain and ordinary meaning.

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al., 2007, Science 317: 1554-1557). Regardless of structure, an antibody fragment binds with the same antigen that is recognized by the intact antibody. For example, an anti-CD22 antibody fragment binds with an epitope of CD22. The term "antibody fragment" also includes isolated fragments consisting of the variable regions, such as the "Fv" fragments consisting of the variable regions of the heavy and light chains, recombinant single chain polypeptide molecules in which light and heavy chain variable regions are connected by a peptide linker ("scFv proteins"), and minimal recognition units consisting of the amino acid residues that mimic the hypervariable region.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

A "therapeutic agent" is an atom, molecule, or compound that is useful in the treatment of a disease. Examples of therapeutic agents include but are not limited to antibodies, antibody fragments, drugs, cytokine or chemokine inhibitors, pro-apoptotic agents, tyrosine kinase inhibitors, toxins, enzymes, nucleases, hormones, immunomodulators, antisense oligonucleotides, siRNA, RNAi, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

An "immunoconjugate" is a conjugate of an antibody with an atom, molecule, or a higher-ordered structure (e.g., with a liposome), a therapeutic agent, or a diagnostic agent. A "naked antibody" is an antibody that is not conjugated to any other agent.

A "naked antibody" is generally an entire antibody that is not conjugated to a therapeutic agent. This is so because the Fc portion of the antibody molecule provides effector functions, such as complement fixation and ADCC (antibody dependent cell cytotoxicity) that set mechanisms into action that may result in cell lysis. However, it is possible that the Fc portion is not required for therapeutic function, with other mechanisms, such as apoptosis, coming into play. Naked antibodies include both polyclonal and monoclonal antibodies, as well as certain recombinant antibodies, such as chimeric, humanized or human antibodies.

As used herein, the term "antibody fusion protein" is a recombinantly produced antigen-binding molecule in which an antibody or antibody fragment is linked to another protein or peptide, such as the same or different antibody or antibody fragment or a DDD or AD peptide (of the DOCK-AND-LOCK™ complexes described below). The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity.

A "bispecific antibody" is an antibody that can bind simultaneously to two targets which are of different structure. Bispecific antibodies (bsAb) and bispecific antibody fragments (bsFab) may have at least one arm that specifically binds to, for example, a B cell, T cell, myeloid-, plasma-, and mast-cell antigen or epitope and at least one other arm that specifically binds to a targetable conjugate that bears a therapeutic or diagnostic agent. A variety of bispecific antibodies can be produced using molecular engineering. Included herein are bispecific antibodies that target a cancer-associated antigen and also an immunotherapeutic T cell, such as CD3-T cells.

The term "direct cytotoxicity" refers to the ability of an agent to inhibit the proliferation or induce the apoptosis of a cell grown in an optimized culture medium in which only the agent and the cell are present.

Preparation of Monoclonal Antibodies

The compositions, formulations and methods described herein may include monoclonal antibodies. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)). General techniques for cloning murine immunoglobulin variable domains have been disclosed, for example, by the publication of Orlandi et al., Proc. Nat'l Acad. Sci. USA 86: 3833 (1989).

Chimeric Antibodies

A chimeric antibody is a recombinant protein that contains the variable domains including the CDRs derived from one species of animal, such as a rodent antibody, while the remainder of the antibody molecule; i.e., the constant domains, is derived from a human antibody. Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and IgG$_1$ constant region domains. This publication also provides the nucleotide sequences of the LL2 light and heavy chain variable regions, $V_k$ and $V_H$, respectively.

Humanized Antibodies

A chimeric monoclonal antibody can be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)). Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

Human Antibodies

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., Molecular Cloning, A laboratory manual, $2^{nd}$ Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human antibody. Alternatively, the Vκ and $V_H$ expression cassettes can be excised and subcloned into a single expression vector, such as pdHL2, as described by Gillies et al. (*J. Immunol. Methods* 125:191 (1989) and also shown in Losman et al., *Cancer,* 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:86) and veltuzumab (SEQ ID NO:85).

hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | | | |
|---|---|---|---|---|---|---|---|
| | Complete allotype | 214 (allotype) | | 356/358 (allotype) | | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3

```
Veltuzumab heavy chain constant region sequence
                                               (SEQ ID NO: 85)
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK Rituximab heavy chain constant region sequence
                                               (SEQ ID NO: 86)
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKAEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK
```

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies

In various embodiments, the claimed methods and compositions may utilize any of a variety of antibodies known in the art. For example, therapeutic use of anti-B cell antibodies, such as anti-CD22 antibodies, may be supplemented with one or more antibodies against other disease-associated antigens. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Antibodies of use may bind to various known antigens expressed in B cells or T cells, including but not limited to BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, CD56, CCD57, CD59, CD64, CD71, CD79a, CD79b, CD117, CD138, FMC-7 and HLA-DR.

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), MN-15 (anti-CEACAM6), Mu-9 (anti-colon-specific antigen-p), Immu 31 (an anti-alpha-fetoprotein), TAG-72 (e.g., CC49), R1 (anti-IGF-1R), Tn, J591 or HuJ591 (anti-PSMA (prostate-specific membrane antigen), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), GA101 (anti-CD20; obinutuzumab) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109, 304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772, 645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575), the text of each recited patent or application is incorporated herein by reference with respect to the Figures and Examples sections.

Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); OKT3 (anti-CDR3); anti-CD40L (UCB, Brussels, Belgium); natalizumab (anti-α4 integrin) and omalizumab (anti-IgE).

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. Nos. 4,704,692, 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos.

4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780).

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797; Hwang and Foote, 2005, Methods 36:3-10; Clark, 2000, Immunol Today 21:397-402; J Immunol 1976 117: 1056-60; Ellison et al., 1982, Nucl Acids Res 13:4071-79; Stickler et al., 2011, Genes and Immunity 12:213-21).

Multispecific and Multivalent Antibodies

Methods for producing bispecific antibodies include engineered recombinant antibodies which have additional cysteine residues so that they crosslink more strongly than the more common immunoglobulin isotypes. (See, e.g., FitzGerald et al, Protein Eng. 10(10):1221-1225, (1997)). Another approach is to engineer recombinant fusion proteins linking two or more different single-chain antibody or antibody fragment segments with the needed dual specificities. (See, e.g., Coloma et al., Nature Biotech. 15:159-163, (1997)). A variety of bispecific antibodies can be produced using molecular engineering. In one form, the bispecific antibody may consist of, for example, an scFv with a single binding site for one antigen and a Fab fragment with a single binding site for a second antigen. In another form, the bispecific antibody may consist of, for example, an IgG with two binding sites for one antigen and two scFv with two binding sites for a second antigen. In alternative embodiments, multispecific and/or multivalent antibodies may be produced as DOCK-AND-LOCK™ (DNL™) complexes as described below.

In certain embodiments, one or more anti-B-cell antibodies may be administered to a patient as part of a combination of antibodies. Bispecific antibodies are preferred to administration of combinations of separate antibodies, due to cost and convenience. However, where combinations of separate antibodies provide improved safety or efficacy, the combination may be utilized. The antibodies may bind to different epitopes of the same antigen or to different antigens. Preferably, the antigens are selected from the group consisting of BCL-1, BCL-2, BCL-6, CD1a, CD2, CD3, CD4, CD5, CD7, CD8, CD10, CD11b, CD11c, CD13, CD14, CD15, CD16, CD19, CD20, CD21, CD22, CD23, CD25, CD33, CD34, CD38, CD40, CD40L, CD41a, CD43, CD45, CD55, CD56, CCD57, CD59, CD64, CD71, CD79a, CD79b, CD117, CD138, FMC-7 and HLA-DR. However, antibodies against other antigens of use for therapy of cancer, autoimmune diseases or immune dysfunction diseases are known in the art, as discussed below, and antibodies against any such disease-associated antigen known in the art may be utilized.

DOCK-AND-LOCK™ (DNL™)

In preferred embodiments, a bivalent or multivalent antibody is formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell. Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ. The R subunits have been isolated only as stable dimers and the dimerization domain has been shown to consist of the first 44 amino-terminal residues of RIIα or RIIβ (Newlon et al., Nat. Struct. Biol. 1999; 6:222). As discussed below, similar portions of the amino acid sequences of other regulatory subunits are involved in dimerization and docking, each located at or near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL™ constructs, different AD or DDD sequences may be utilized. Exemplary DDD and AD sequences are provided below.

```
DDD1
                                            (SEQ ID NO: 1)
SHIQIPPGLTELLQGYTVEVLRQQPPDLVEFAVEYFTRLREARA

DDD2
                                            (SEQ ID NO: 2)
CGHIQIPPGLTELLQGYTVEVLRQQPPDLVEFAVEYFTRLREARA

AD1
                                            (SEQ ID NO: 3)
QIEYLAKQIVDNAIQQA

AD2
                                            (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                            (SEQ ID NO: 5)
SLRECELYVQKHNIQALLKDSIVQLCTARPERPMAFLREYFERLEKEEAK
```

```
DDD3C
                                                       (SEQ ID NO: 6)
MSCGGSLRECELYVQKHNIQALLKDSIVQLCTARPERPMAFLREYFERLE
KEEAK

AD3
                                                       (SEQ ID NO: 7)
CGFEELAWKIAKMIWSDVFQQGC
```

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                                       (SEQ ID NO: 8)
SLRECELYVQKHNIQALLKDVSIVQLCTARPERPMAFLREYFEKLEKEEAK

PKA RIβ
                                                       (SEQ ID NO: 9)
SLKGCELYVQLHGIQQVLKDCIVHLCISKPERPMKFLREHFEKLEKEENRQILA

PKA RIIα
                                                       (SEQ ID NO: 10)
SHIQIPPGLTELLQGYTVEVGQQPPDLVDFAVEYFTRLREARRQ

PKA RIIβ
                                                       (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                                       (SEQ ID NO: 1)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 2

Conservative Amino Acid Substitutions in DDD1 (SEQ ID NO: 1). Consensus sequence disclosed as SEQ ID NO: 87.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K |  N |   |   |   |   |   | A |   | S | D |   |   |   | N | A | S |   | D |   | K |
|   | R |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E |   |   |   |   | D |   | L |   | D |   | S | K |   | K | D | L | K | L |
|   |   |   |   |   |   |   |   |   |   | I |   |   |   |   |   |   |   |   |   |   | I |   I |
|   |   |   |   |   |   |   |   |   |   | V |   |   |   |   |   |   |   |   |   |   | V |   V |

```
THIQIPPGLTELLQGYTVEVLRQQPPDLVEFAVEYFTRLREARA (SEQ ID NO: 12)

SKIQIPPGLTELLQGYTVEVLRQQPPDLVEFAVEYFTRLREARA (SEQ ID NO: 13)
```

TABLE 2-continued

Conservative Amino Acid Substitutions in DDD1 (SEQ ID NO: 1). Consensus sequence disclosed as SEQ ID NO: 87.

```
SRIQ

TABLE 3-continued

Conservative Amino Acid Substitutions in AD1 (SEQ ID NO: 3). Consensus sequence disclosed as SEQ ID NO: 88.

QIDYLAKQIVDNAIQQA (SEQ ID NO: 35)

QIEFLAKQIVDNAIQQA (SEQ ID NO: 36)

QIETLAKQIVDNAIQQA (SEQ ID NO: 37)

QIESLAKQIVDNAIQQA (SEQ ID NO: 38)

QIEYIAKQIVDNAIQQA (SEQ ID NO: 39)

QIEYVAKQIVDNAIQQA (SEQ ID NO: 40)

QIEYLARQIVDNAIQQA (SEQ ID NO: 41)

QIEYLAKNIVDNAIQQA (SEQ ID NO: 42)

QIEYLAKQIVENAIQQA (SEQ ID NO: 43)

QIEYLAKQIVDQAIQQA (SEQ ID NO: 44)

QIEYLAKQIVDNAINQA (SEQ ID NO: 45)

QIEYLAKQIVDNAIQNA (SEQ ID NO: 46)

QIEYLAKQIVDNAIQQL (SEQ ID NO: 47)

QIEYLAKQIVDNAIQQI (SEQ ID NO: 48)

QIEYLAKQIVDNAIQQV (SEQ ID NO: 49)

Gold et al. (2006, Mol Cell 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

```
SuperAKAP-IS
                                    (SEQ ID NO: 50)
QIEYVAKQIVDYAIHQA Alternative AKAP sequences
                                    (SEQ ID NO: 51)
QIEYKAKQIVDHAIHQA (SEQ ID NO: 52)
QIEYHAKQIVDHAIHQA (SEQ ID NO: 53)
QIEYVAKQIVDHAIHQA
```

Figure 2:
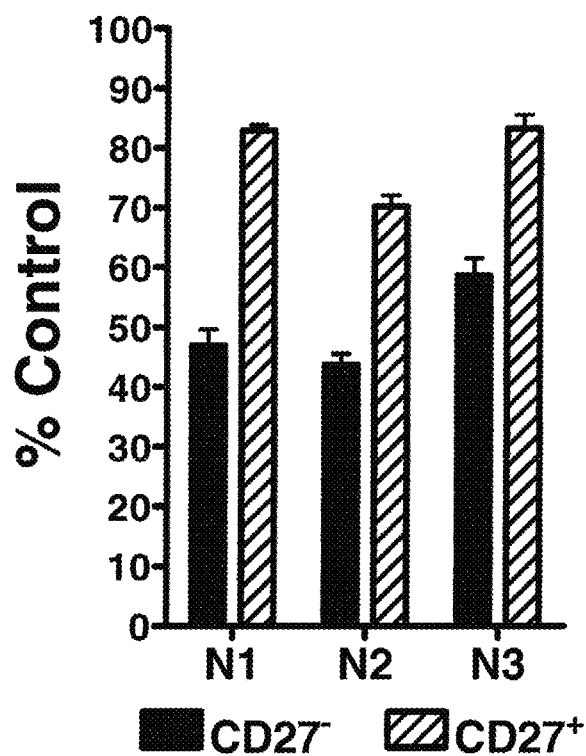
FIG. 2. Reduction of CD19 on $CD27^+$ and $CD27^-$ B cells from three healthy donors (N1, N2 and N3). The % mean fluorescence intensity of the isotype control treatment is shown. Error bars, Std. Dev.

FIG. 2 of Gold et al. disclosed additional DDD-binding sequences from a variety of AKAP proteins, shown below.

RII-Specific AKAPs

```
AKAP-KL
                                    (SEQ ID NO: 54)
PLEYQAGLLVQNAIQQAI

AKAP79
                                    (SEQ ID NO: 55)
LLIETASSLVKNAIQLSI

AKAP-Lbc
                                    (SEQ ID NO: 56)
LIKEAASRIVDAVIEQVK
```

RI-Specific AKAPs

```
AKAPce
                                    (SEQ ID NO: 57)
ALYQFADRFSELVISEAL

RIAD
                                    (SEQ ID NO: 58)
LEQVANQLADQIIKEAT

PV38
                                    (SEQ ID NO: 59)
FEELAWKIAKMIWSDVF
```

Dual-Specificity AKAPs

```
AKAP7
                                    (SEQ ID NO: 60)
ELVRLSKRLVENAVLKAV

MAP2D
                                    (SEQ ID NO: 61)
TAEEVSARIVQVVTAEAV
```

-continued

DAKAP1

QIKQAAFQLISQVILEAT (SEQ ID NO: 62)

DAKAP2

LAWKIAKMIVSDVMQQ (SEQ ID NO: 63)

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

AKAP Peptide sequences

| | Peptide Sequence |
|---|---|
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASR1PDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Stokka et al. (2006, Biochem J 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

Ht31

DLIEEAASRIVDAVIEQVKAAGAY (SEQ ID NO: 64)

RIAD

LEQYANQLADQIIKEATE (SEQ ID NO: 65)

PV-38

FEELAWKIAKMIWSDVFQQC (SEQ ID NO: 66)

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS

QIEYL<u>AKQ</u>IVDN<u>AI</u>QQA (SEQ ID NO: 3)

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties.

These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SH*IQI*PPGLT*ELL*QGY TV*EVL*RQQPP*DLVEFA*VE*YF*TR*LR*EA*R*A

A modified set of conservative amino acid substitutions for the DDD1 (SEQ ID NO:1) sequence, based on the data of Carr et al. (2001) is shown in Table 5. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 2 and Table 3.

TABLE 5

Conservative Amino Acid Substitutions in DDD1 (SEQ ID NO: 1). Consensus sequence disclosed as SEQ ID NO: 89.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | | | N | | | | | | S | | | | | | | | I<br>L<br>A | | | | |
| Q | Q | P | P | D | L | V | E | F | A | V | E | Y | F | T | R | L | R | E | A | R | A |
| N | | | | | | | | | | I<br>L<br>A | D | | | S | K | | K | | L<br>I<br>V | | L<br>I<br>V |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.). Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Affibodies and Fynomers

Certain alternative embodiments may utilize affibodies in place of antibodies. Affibodies are commercially available from Affibody AB (Solna, Sweden). Affibodies are small proteins that function as antibody mimetics and are of use in binding target molecules. Affibodies were developed by combinatorial engineering on an alpha helical protein scaffold (Nord et al., 1995, Protein Eng 8:601-8; Nord et al., 1997, Nat Biotechnol 15:772-77). The affibody design is based on a three helix bundle structure comprising the IgG binding domain of protein A (Nord et al., 1995; 1997). Affibodies with a wide range of binding affinities may be produced by randomization of thirteen amino acids involved in the Fc binding activity of the bacterial protein A (Nord et al., 1995; 1997). After randomization, the PCR amplified library was cloned into a phagemid vector for screening by phage display of the mutant proteins. The phage display library may be screened against any known antigen, using standard phage display screening techniques (e.g., Pasqualini and Ruoslahti, 1996, Nature 380:364-366; Pasqualini, 1999, Quart. J. Nucl. Med. 43:159-162), in order to identify one or more affibodies against the target antigen.

A $^{177}$Lu-labeled affibody specific for HER2/neu has been demonstrated to target HER2-expressing xenografts in vivo (Tolmachev et al., 2007, Cancer Res 67:2773-82). Although renal toxicity due to accumulation of the low molecular weight radiolabeled compound was initially a problem, reversible binding to albumin reduced renal accumulation, enabling radionuclide-based therapy with labeled affibody (Id.).

The feasibility of using radiolabeled affibodies for in vivo tumor imaging has been recently demonstrated (Tolmachev et al., 2011, Bioconjugate Chem 22:894-902). A maleimide-derivatized NOTA was conjugated to the anti-HER2 affibody and radiolabeled with $^{111}$In (Id.). Administration to mice bearing the HER2-expressing DU-145 xenograft, followed by gamma camera imaging, allowed visualization of the xenograft (Id.).

Fynomers can also bind to target antigens with a similar affinity and specificity to antibodies. Fynomers are based on the human Fyn SH3 domain as a scaffold for assembly of binding molecules. The Fyn SH3 domain is a fully human, 63 amino acid protein that can be produced in bacteria with high yields. Fynomers may be linked together to yield a multispecific binding protein with affinities for two or more different antigen targets. Fynomers are commercially available from COVAGEN AG (Zurich, Switzerland).

The skilled artisan will realize that affibodies or fynomers may be used as targeting molecules in the practice of the claimed methods and compositions.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074, 405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Targetable Constructs

In certain embodiments, targetable construct peptides labeled with one or more therapeutic or diagnostic agents for use in pre-targeting may be selected to bind to a bispecific antibody with one or more binding sites for a targetable construct peptide and one or more binding sites for a target antigen associated with a disease or condition. Bispecific antibodies may be used in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO: 90), wherein DOTA is 1,4,7,10-tetraazacyclododecane-1,4,7,10-tetraacetic acid and HSG is the histamine succinyl glycyl group. Alternatively, DOTA may be replaced by NOTA (1,4,7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties. Chelating moieties may be used, for example, to bind to a therapeutic and or diagnostic radionuclide, paramagnetic ion or contrast agent.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

Preparation of Immunoconjugates

In preferred embodiments, a therapeutic or diagnostic agent may be covalently attached to an antibody or antibody fragment to form an immunoconjugate. Where the immunoconjugate is to be administered in concentrated form by subcutaneous, intramuscular or transdermal delivery, the skilled artisan will realize that only non-cytotoxic agents may be conjugated to the antibody. Where a second antibody or fragment thereof is administered by a different route, such as intravenously, either before, simultaneously with or after the subcutaneous, intramuscular or transdermal delivery, then the type of diagnostic or therapeutic agent that may be conjugated to the second antibody or fragment thereof is not so limited, and may comprise any diagnostic or therapeutic agent known in the art, including cytotoxic agents.

In some embodiments, a diagnostic and/or therapeutic agent may be attached to an antibody or fragment thereof via a carrier moiety. Carrier moieties may be attached, for example to reduced SH groups and/or to carbohydrate side chains. A carrier moiety can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the carrier moiety can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.). For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.).

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.). Examples of such substituted cyclooctynes include difluorinated cyclooctynes, 4-dibenzocyclooctynol and azacyclooctyne (Id.). An alternative copper-free reaction involved strain-promoted alkyne-nitrone cycloaddition to give N-alkylated isoxazolines (Id.). The reaction was reported to have exceptionally fast reaction kinetics and was used in a one-pot three-step protocol for site-specific modification of peptides and proteins (Id.). Nitrones were prepared by the condensation of appropriate aldehydes with N-methylhydroxylamine and the cycloaddition reaction took place in a mixture of acetonitrile and water (Id.). These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.). Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.). The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.). The results confirmed the in vivo chemical reaction of the TCO and tetrazine-labeled molecules.

Antibody labeling techniques using biological incorporation of labeling moieties are further disclosed in U.S. Pat. No. 6,953,675 (the Examples section of which is incorporated herein by reference). Such "landscaped" antibodies were prepared to have reactive ketone groups on glycosylated sites. The method involved expressing cells transfected with an expression vector encoding an antibody with one or more N-glycosylation sites in the CH1 or Vκ domain in culture medium comprising a ketone derivative of a saccharide or saccharide precursor. Ketone-derivatized saccharides or precursors included N-levulinoyl mannosamine and N-levulinoyl fucose. The landscaped antibodies were subsequently reacted with agents comprising a ketone-reactive moiety, such as hydrazide, hydrazine, hydroxylamino or thiosemicarbazide groups, to form a labeled targeting molecule. Exemplary agents attached to the landscaped antibodies included chelating agents like DTPA, large drug molecules such as doxorubicin-dextran, and acyl-hydrazide containing peptides. The landscaping technique is not limited to producing antibodies comprising ketone moieties, but may be used instead to introduce a click chemistry reactive group, such as a nitrone, an azide or a cyclooctyne, onto an antibody or other biological molecule.

Modifications of click chemistry reactions are suitable for use in vitro or in vivo. Reactive targeting molecule may be formed either by either chemical conjugation or by biological incorporation. The targeting molecule, such as an antibody or antibody fragment, may be activated with an azido moiety, a substituted cyclooctyne or alkyne group, or a nitrone moiety. Where the targeting molecule comprises an azido or nitrone group, the corresponding targetable construct will comprise a substituted cyclooctyne or alkyne group, and vice versa. Such activated molecules may be made by metabolic incorporation in living cells, as discussed above.

Alternatively, methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

Therapeutic and Diagnostic Agents

In certain embodiments, the antibodies or fragments thereof may be used in combination with one or more therapeutic and/or diagnostic agents. Where the agent is attached to an antibody or fragment thereof to be administered by subcutaneous, intramuscular or transdermal administration of a concentrated antibody formulation, then only non-cytotoxic agents are contemplated. Non-cytotoxic agents may include, without limitation, immunomodulators, cytokines (and their inhibitors), chemokines (and their inhibitors), tyrosine kinase inhibitors, growth factors, hormones and certain enzymes (i.e., those that do not induce local necrosis), or their inhibitors. Where the agent is co-administered either before, simultaneously with or after the subcutaneous, intramuscular or transdermal antibody formulation, then cytotoxic agents may be utilized. An agent may be administered as an immunoconjugate with a second antibody or fragment thereof, or may be administered as a free agent. The following discussion applies to both cytotoxic and non-cytotoxic agents.

Therapeutic agents may be selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a tyrosine kinase inhibitor, a Bruton kinase inhibitor, a sphingosine inhibitor, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents, and combinations thereof.

Exemplary drugs may include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Immunomodulators may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -λ, or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, -λ, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, kit-ligand or FLT-3, angiostatin, thrombospondin, endostatin, tumor necrosis factor and lymphotoxin.

Chemokines of use include RANTES, MCAF, MIP1-alpha, MIP1-Beta and IP-10.

Radioactive isotopes include, but are not limited to $^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

A variety of tyrosine kinase inhibitors are known in the art and any such known therapeutic agent may be utilized. Exemplary tyrosine kinase inhibitors include, but are not limited to canertinib, dasatinib, erlotinib, gefitinib, imatinib, lapatinib, leflunomide, nilotinib, pazopanib, semaxinib, sorafenib, sunitinib, sutent and vatalanib. A specific class of tyrosine kinase inhibitor is the Bruton tyrosine kinase inhibitor. Bruton tyrosine kinase (Btk) has a well-defined role in B-cell development. Bruton kinase inhibitors include, but are not limited to, PCI-32765 (ibrutinib), PCI-45292, GDC-0834, LFM-A13 and RN486.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photo-activated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (PlGF) peptides and antibodies, anti-vascular growth factor antibodies (such as anti-VEGF and anti-PlGF), anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, interferon-lambda, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

The therapeutic agent may comprise an oligonucleotide, such as a siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p 53 (7,781,575), and apolipoprotein B (7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Mirus Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 6. Although siRNA is delivered as a double-stranded molecule, for simplicity only the sense strand sequences are shown in Table 6.

TABLE 6

Exemplary siRNA Sequences

| Target | Sequence | SEQ ID NO |
|---|---|---|
| VEGF R2 | AATGCGGCGGTGGTGACAGTA | SEQ ID NO: 91 |
| VEGF R2 | AAGCTCAGCACACAGAAAGAC | SEQ ID NO: 92 |
| CXCR4 | UAAAAUCUUCCUGCCCACCdTdT | SEQ ID NO: 93 |
| CXCR4 | GGAAGCUGUUGGCUGAAAAdTdT | SEQ ID NO: 94 |
| PPARC1 | AAGACCAGCCUCUUUGCCCAG | SEQ ID NO: 95 |
| Dynamin 2 | GGACCAGGCAGAAAACGAG | SEQ ID NO: 96 |
| Catenin | CUAUCAGGAUGACGCGG | SEQ ID NO: 97 |
| E1A binding protein | UGACACAGGCAGGCUUGACUU | SEQ ID NO: 98 |
| Plasminogen activator | GGTGAAGAAGGGCGTCCAA | SEQ ID NO: 99 |
| K-ras | GATCCGTTGGAGCTGTTGGCGTAGTT CAAGAGACTCGCCAACAGCTCCAACT TTTGGAAA | SEQ ID NO: 100 |
| Sortilin 1 | AGGTGGTGTTAACAGCAGAG | SEQ ID NO: 101 |
| Apolipoprotein E | AAGGTGGAGCAAGCGGTGGAG | SEQ ID NO: 102 |
| Apolipoprotein E | AAGGAGTTGAAGGCCGACAAA | SEQ ID NO: 103 |

TABLE 6 -continued

Exemplary siRNA Sequences

| Target | Sequence | SEQ ID NO |
|---|---|---|
| Bcl-X | UAUGGAGCUGCAGAGGAUGdTdT | SEQ ID NO: 104 |
| Raf-1 | TTTGAATATCTGTGCTGAGAACACAGTTCTCAGCACAGATATTCTTTTT | SEQ ID NO: 105 |
| Heat shock transcription factor 2 | AATGAGAAAAGCAAAAGGTGCCCTGTCTC | SEQ ID NO: 106 |
| IGFBP3 | AAUCAUCAUCAAGAAAGGGCA | SEQ ID NO: 107 |
| Thioredoxin | AUGACUGUCAGGAUGUUGCdTdT | SEQ ID NO: 108 |
| CD44 | GAACGAAUCCUGAAGACAUCU | SEQ ID NO: 109 |
| MMP14 | AAGCCTGGCTACAGCAATATGCCTGTCTC | SEQ ID NO: 110 |
| MAPKAPK2 | UGACCAUCACCGAGUUUAUdTdT | SEQ ID NO: 111 |
| FGFR1 | AAGTCGGACGCAACAGAGAAA | SEQ ID NO: 112 |
| ERBB2 | CUACCUUUCUACGGACGUGdTdT | SEQ ID NO: 113 |
| BCL2L1 | CTGCCTAAGGCGGATTTGAAT | SEQ ID NO: 114 |
| ABL1 | TTAUUCCUUCUUCGGGAAGUC | SEQ ID NO: 115 |
| CEACAM1 | AACCTTCTGGAACCCGCCCAC | SEQ ID NO: 116 |
| CD9 | GAGCATCTTCGAGCAAGAA | SEQ ID NO: 117 |
| CD151 | CATGTGGCACCGTTTGCCT | SEQ ID NO: 118 |
| Caspase 8 | AACTACCAGAAAGGTATACCT | SEQ ID NO: 119 |
| BRCA1 | UCACAGUGUCCUUUAUGUAdTdT | SEQ ID NO: 120 |
| p53 | GCAUGAACCGGAGGCCCAUUU | SEQ ID NO: 121 |
| CEACAM6 | CCGGACAGTTCCATGTATA | SEQ ID NO: 122 |

The skilled artisan will realize that Table 6 represents a very small sampling of the total number of siRNA species known in the art, and that any such known siRNA may be utilized in the claimed methods and compositions.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Administration

The subject antibodies and immunoglobulins in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active ingredients (i.e., the labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection, more preferably by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising antibodies can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The formulation thereof should be in a solution having a suitable pharmaceutically acceptable buffer such as phosphate, TRIS (hydroxymethyl)aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

The dosage of an administered antibody for humans will vary depending upon such factors as the patient's age, weight, height, sex, general medical condition and previous medical history. Typically, it is desirable to provide the recipient with a dosage of antibody that is in the range of from about 1 mg to 600 mg as a single infusion or single or multiple injections, although a lower or higher dosage also may be administered. Typically, it is desirable to provide the recipient with a dosage that is in the range of from about 50 mg per square meter ($m^2$) of body surface area or 70 to 85 mg of the antibody for the typical adult, although a lower or higher dosage also may be administered. Examples of dosages of antibodies that may be administered to a human subject are 1 to 1,000 mg, more preferably 1 to 70 mg, most preferably 1 to 20 mg, although higher or lower doses may be used. Dosages may be repeated as needed, for example, once per week for 4-10 weeks, preferably once per week for 8 weeks, and more preferably, once per week for 4 weeks. It may also be given less frequently, such as every other week for several months, or more frequently, such as twice weekly or by continuous infusion.

More recently, subcutaneous administration of veltuzumab has been given to NHL patients in 4 doses of 80, 160 or 320 mg, repeated every two weeks (Negrea et al., 2011, Haematologica 96:567-73). Only occasional, mild to moderate and transient injection reactions were observed, with no other safety issues (Id.). The objective response rate (CR+CRu+PR) was 47%, with a CR/CRu (complete response) rate of 24% (Id.). Interestingly, the 80 mg dosage group showed the highest percentage of objective response (2/3, 67%), with one of three patients showing a complete response (Id.). Four out of eight objective responses continued for 60 weeks (Id.). All serum samples evaluated for HAHA were negative (Id.). Although the low sample population reported in this study precludes any definitive conclusions on optimal dosing, it is apparent that therapeutic response was observed at the lowest dosage tested (80 mg).

In certain alternative embodiments, the antibody may be administered by transdermal delivery. Different methods of transdermal delivery are known in the art, such as by transdermal patches or by microneedle devices, and any such known method may be utilized. In an exemplary embodiment, transdermal delivery may utilize a delivery device such as the 3M hollow Microstructured Transdermal System (hMTS) for antibody based therapeutics. The hMTS device comprises a 1 $cm^2$ microneedle array consisting of 18 hollow microneedles that are 950 microns in length, which penetrate approximately 600-700 microns into the dermal layer of the skin where there is a high density of lymphatic channels. A spring-loaded device forces the antibody composition from a fluid reservoir through the microneedles for delivery to the subject. Only transient erythema and edema at the injection site are observed (Burton et al., 2011, Pharm Res 28:31-40). The hMTS device is not perceived as a needle injector, resulting in improved patient compliance.

In alternative embodiments, transdermal delivery of peptides and proteins may be achieved by (1) coadministering with a synthetic peptide comprising the amino acid sequence of ACSSSPSKHCG (SEQ ID NO:123) as reported by Chen et al. (Nat Biotechnol 2006; 24: 455-460) and Carmichael et al. (Pain 2010; 149:316-324); (2) coadministering with arginine-rich intracellular delivery peptides as reported by Wang et al. (BBRC 2006; 346: 758-767); (3) coadminstering with either AT1002 (FCIGRLCG, SEQ ID NO:124) or Tat (GRKKRRN-RRRCG, SEQ ID NO:125) as reported by Uchida et al. (Chem Pharm Bull 2011; 59:196); or (4) using an adhesive transdermal patch as reported by Jurynczyk et al (Ann Neurol 2010; 68:593-601). In addition, transdermal delivery of negatively charged drugs may be facilitated by combining with the positively charged, pore-forming magainin peptide as reported by Kim et al. (Int J Pharm 2008; 362:20-28).

In preferred embodiments where the antibody is administered subcutaneously, intramuscularly or transdermally in a concentrated formulation, the volume of administration is preferably limited to 3 ml or less, more preferably 2 ml or less, more preferably 1 ml or less. The use of concentrated antibody formulations allowing low volume subcutaneous, intramuscular or transdermal administration is preferred to the use of more dilute antibody formulations that require specialized devices and ingredients (e.g., hyaluronidase) for subcutaneous administration of larger volumes of fluid, such as 10 ml or more. The subcutaneous, intramuscular or transdermal delivery may be administered as a single administration to one skin site or alternatively may be repeated one or more times, or even given to more than one skin site in one therapeutic dosing session. However, the more concentrated the formulation, the lower the volume injected and the fewer injections will be needed for each therapeutic dosing.

Methods of Use

In preferred embodiments, the concentrated antibodies are of use for therapy of cancer. Examples of cancers include, but are not limited to, carcinoma, lymphoma, blastoma, glioma, melanoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, neuroblastoma, cervical cancer, ovarian cancer, liver cancer, bladder cancer, hepatoma, breast cancer, colon cancer, rectal cancer, endometrial cancer or uterine carcinoma, salivary gland carcinoma, kidney or renal cancer, prostate cancer, vulval cancer, thyroid cancer, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: acute childhood lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalamic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatic bile duct cancer, eye cancer, female breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lymphoproliferative disorders, macroglobulinemia, male breast cancer, malignant mesothelioma, malignant thymoma, medulloblastoma, melanoma, mesothelioma, metastatic occult primary squamous neck cancer, metastatic primary squamous neck cancer, metastatic squamous neck cancer, multiple myeloma, multiple myeloma/plasma cell neoplasm, myelodysplastic syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatic squamous neck cancer, oropharyngeal cancer, osteo-/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, Sezary syndrome, skin cancer, small cell lung cancer, small intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethral cancer, uterine cancer, uterine sarcoma, vaginal cancer, visual pathway and hypothalamic glioma, vulvar cancer, Waldenstrom's macroglobulinemia, Wilms' tumor, and any other hyperproliferative disease, besides neoplasia, located in an organ system listed above.

The methods and compositions described and claimed herein may be used to detect or treat malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected and/or treated include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

The exemplary conditions listed above that may be treated are not limiting. The skilled artisan will be aware that antibodies or antibody fragments are known for a wide variety of conditions, such as autoimmune disease, graft-versus-host-disease, organ transplant rejection, cardiovascular disease, neurodegenerative disease, metabolic disease, cancer, infectious disease and hyperproliferative disease.

Exemplary autoimmune diseases include acute idiopathic thrombocytopenic purpura, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, juvenile diabetes mellitus, Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis and fibrosing alveolitis.

Kits

Various embodiments may concern kits containing components suitable for treating diseased tissue in a patient. Exemplary kits may contain at least one concentrated antibody or fragment thereof as described herein. A device capable of delivering the kit components by injection, for example, a syringe for subcutaneous injection, may be included. Where transdermal administration is used, a delivery device such as hollow microneedle delivery device may be included in the kit. Exemplary transdermal delivery devices are known in the art, such as 3M's hollow Microstructured Transdermal System (hMTS), and any such known device may be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Alternatively, the concentrated antibody may be delivered and stored as a liquid formulation. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

Epratuzumab-Induced Trogocytosis of BCR-Response Modulating Proteins Ex Vivo

The humanized anti-CD22 antibody, epratuzumab, has demonstrated therapeutic activity in clinical trials of patients with non-Hodgkin lymphoma (NHL), acute lymphoblastic leukemia, primary Sjögren's syndrome, and systemic lupus erythematosus (SLE). Thus, epratuzumab offers a promising option for CD22-targeted immunotherapy of B-cell lymphomas and autoimmune diseases. However, its mechanism of action (MOA) remains incompletely understood to-date. Because epratuzumab has modest, but significant, antibody-dependent cell-mediated cytotoxicity and negligible complement-dependent cytotoxicity when evaluated in vitro, and its moderate depletion of circulating B cells in patients (35% on average) may be overestimated due to use of $CD19^+$ cells to measure B cells by flow cytometry (discussed below), the therapeutic action of epratuzumab in vivo may not result from B-cell depletion. We investigated whether ligation of epratuzumab to CD22 could modulate other surface molecules on B cells. In particular, we focused on those surface molecules involved in regulating antigen-specific B-cell receptor (BCR) signaling, since modulation of such molecules may lead to altered B-cell functions that ultimately mitigate symptoms of autoimmune or other diseases. With regard to its function of killing malignant B cells expressing CD22, our studies have shown that these effects are more related to the BCR signaling pathway than effector-cell function.

Here we report for the first time that epratuzumab induces a substantial reduction of CD22, along with CD19, CD21, CD20, and CD79b, on the surface of B cells in peripheral blood mononuclear cells (PBMCs) obtained from normal donors or lupus patients, and three NHL Burkitt cell lines (Daudi, Raji, and Ramos) spiked into normal PBMCs. The intriguing observation that only CD22, but not other surface markers, was appreciably decreased by epratuzumab in isolated NHL cells prompted us to assess the role of FcγR-bearing effector cells, with the finding that epratuzumab effectively mediates trogocytosis [a process whereby cells binding to antigen-presenting cells extract surface molecules from these cells and express them on their own surface] of multiple surface proteins from B cells to monocytes, NK cells, and neutrophils. This mechanism of action may explain the limited effectiveness of high doses of epratuzumab compared to lower doses in patients with SLE.

Peripheral blood mononuclear cells (PBMCs) obtained from healthy donors were incubated overnight (16-24 h) with 10 μg/mL of either epratuzumab or an isotype control mAb (hMN-14) and the relative levels of various antigens on the surface of the B cells were analyzed by flow cytometry. PBMCs from heparinized whole blood of normal donors were isolated by density gradient centrifugation on UNI-SEP tubes (Novamed Ltd, Israel). PBMCs were reconstituted in RPMI media supplemented with 10% heat inactivated fetal bovine serum and plated at a cell density of $1.5 \times 10^6$/mL in non-tissue culture treated 48-well plates. Epratuzumab or hMN-14 were added to triplicate wells at a final concentration of 10 μg/mL and incubated overnight (16-20 h) before staining with fluorescent-labeled primary antibodies (Biolegend) following the manufacturers suggested protocols. Stained cells were analyzed by flow cytometry on a FACSCALIBUR® (BD Biosciences) using Flowjo (V7.6.5) software. Initially, the lymphocyte population was gated by side vs. forward scattering, and B cells were further gated from this population with the CD19 signal. The mean fluorescence intensity (MFI), obtained with fluorochrome-conjugated antibodies to various cell surface antigens, on the gated B cells was calculated following treatment with epratuzumab, hMN-14 or without antibody. PBMCs from 16 healthy donors were assessed in various experiments.

Figure 3:
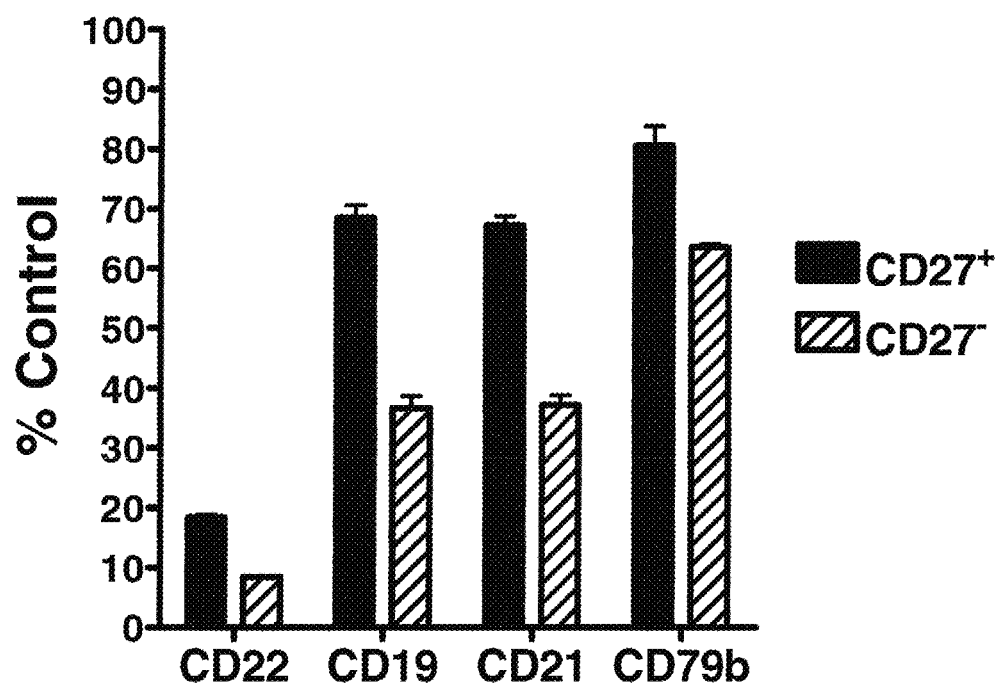
FIG. 3. Example of the reduction of CD19, CD22, CD21 and CD79b on $CD27^+$ and $CD27^-$ B cells from a healthy donor. The % mean fluorescence intensity of the isotype control treatment is shown. Error bars, Std. Dev.
Figure 4:
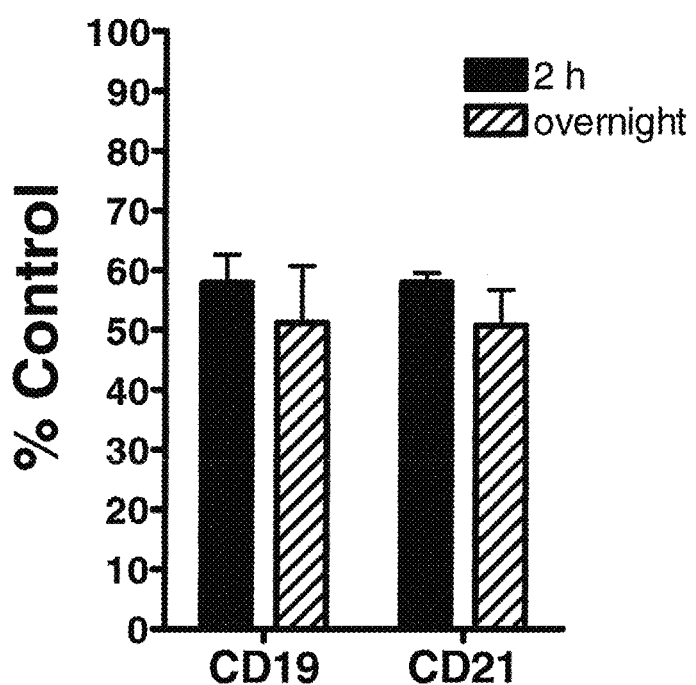
FIG. 4. Comparison of the reduction of CD19 and CD21 on B cells following 2 h (N=5 donors) vs. overnight treatment (N=16 donors) with 10 µg/mL epratuzumab or isotype control (hMN-14). The % mean fluorescence intensity of the isotype control treatment is shown. Error bars, Std. Dev.

Treatment with the control mAb (hMN-14) did not affect the levels of any of the tested proteins and resulted in MFI measurements that were very similar to untreated samples. Alternatively, epratuzumab significantly reduced the levels of key BCR-regulating proteins, including CD22, CD19, CD21 and CD79b, which were reduced to 10, 50, 52 and 70%, respectively, of the level of untreated or control mAb (FIG. 1). CD20 (82%) and CD62L (73%) also were reduced, but to a lesser extent. Other surface proteins including CD27 (on CD27$^+$ B cells), CD40, CD44, CD45, β7 integrin and LFA-1 (CD11a and CD18) were affected minimally (<10% change) by epratuzumab. CD27$^-$ naive B cells were more responsive to epratuzumab compared to CD27$^+$ memory B cells, as shown with PBMCs as shown for CD19 from 3 different healthy donors (FIG. 2). CD22, CD21 and CD79b were also reduced to a greater extent on CD27$^-$ cells (FIG. 3). The effect was essentially complete within a few hours. The reductions in surface CD19 and CD21 were not significantly different following 2-h or overnight treatment (FIG. 4).

Example 2

Effect of Various B Cell-Targeting Antibodies

Figure 5:
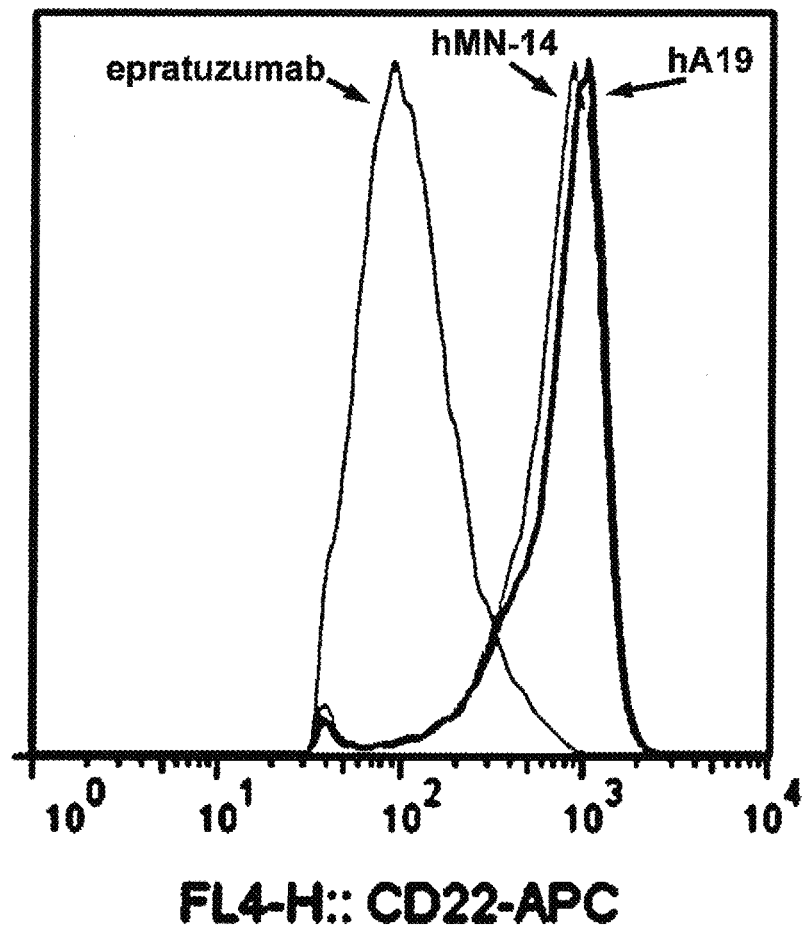
FIG. 5. Histogram showing CD22 levels on B cells gated from PBMCs of healthy donors following overnight treatment with 10 µg/mL epratuzumab, hA19 (anti-CD19) or isotype control (hMN-14).
Figure 6:
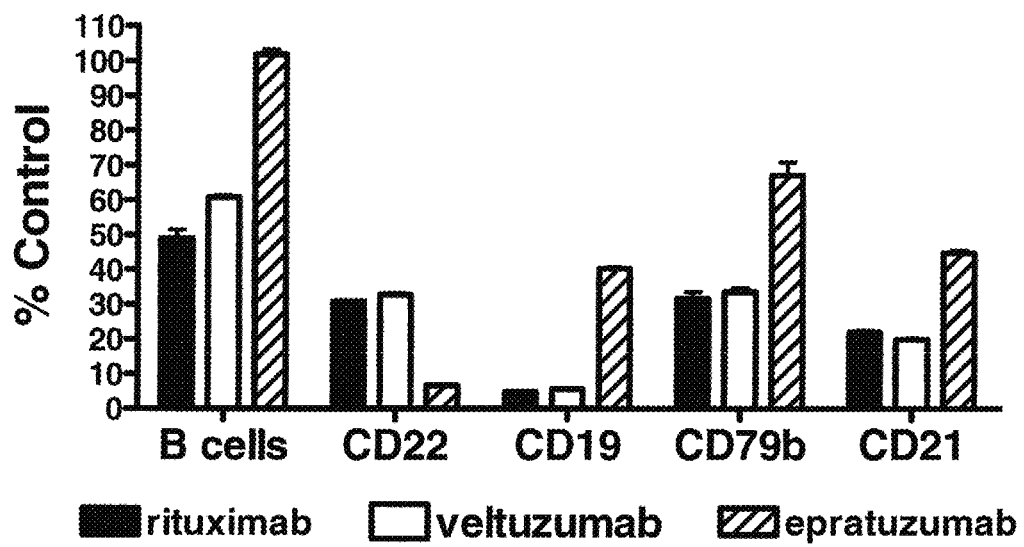
FIG. 6. Fresh PBMCs isolated from healthy donors were treated overnight with epratuzumab, veltuzumab or rituximab. The relative B cell count (B cells) and levels of CD19, CD22, CD21 and CD79b following treatment is shown as the % mean fluorescence intensity of the isotype control (hMN-14) treatment at the same protein concentration. Error bars, Std. Dev.

We investigated whether the reciprocal effect might occur, whereby a mAb to CD19 (mAb hA19) could reduce the surface level of CD22 from B cells within PBMCs. However, hA19 had no effect on the level of CD22 (FIG. 5). We were unable to determine the level of CD19 following treatment with hA19 because its binding blocked detection with anti-CD19. The CD20-targeting mAbs rituximab and veltuzumab each diminished CD19, CD21 and CD79b to a greater extent than epratuzumab (FIG. 6). Rituximab also reduced CD22, but to a lesser extent than epratuzumab. Notably, rituximab and veltuzumab (at 10 μg/mL) reduced the B cell count by 50%, and 40%, where epratuzumab did not cause significant B cell depletion, either at 10 μg/mL or 1 mg/mL.

TABLE 7

Comparison of epratuzumab with other humanized antibodies targeting different antigens on B cells.

| Target | mAb | CD19 | CD20 | CD21 | CD22 | CD74 |
|---|---|---|---|---|---|---|
| CD22 | epratuzumab | 30-60% (↓) | 10-30% (↓) | 30-60% (↓) | >60% (↓) | 10-30% (↑) |
| CD20 | veltuzumab | >60% (↓) | nd | >60% (↓) | 10-30% (↓) | 30-60% (↑) |
| CD19 | hA19 | nd | <10% | 10-30% (↓) | <10% | 30-60% (↑) |
| CD74 | milatuzumab | <10% | <10% | 10-30% (↓) | nd | nd |

↓, decreased;
↑, increased;
nd, not determined

Example 3

Dose-Dependent Trogocytosis with Epratuzumab

Figure 7:
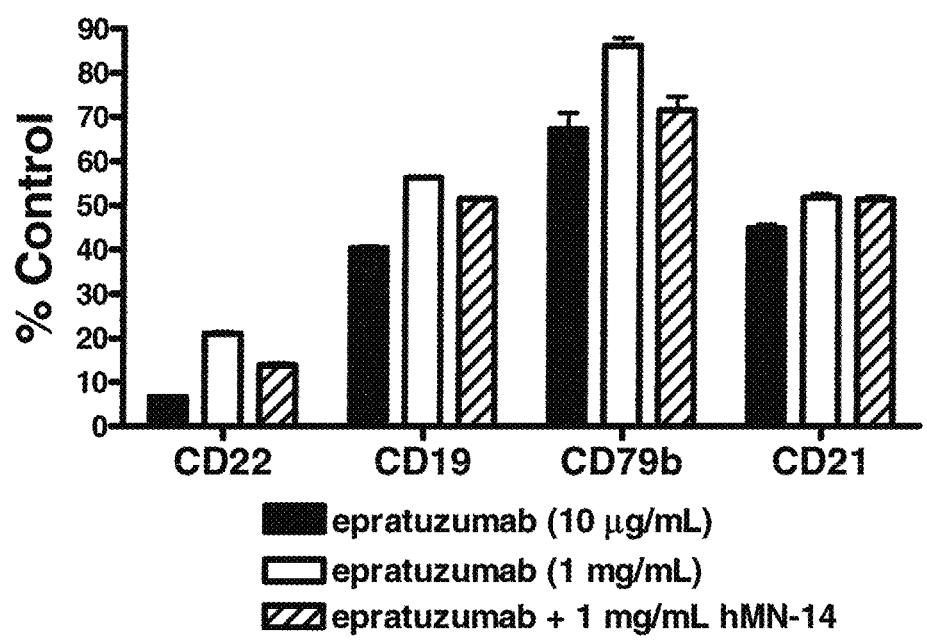
FIG. 7. Fresh PBMCs isolated from healthy donors were treated overnight with 10 µg/mL epratuzumab, 1 mg/mL epratuzumab or 10 µg/mL epratuzumab plus 1 mg/mL hMN-14. The B cell surface levels of CD19, CD21, CD22 and CD79b are shown as the % mean fluorescence intensity of the isotype control (hMN-14) treatment at the same protein concentration. Error bars, Std. Dev.
Figure 8:
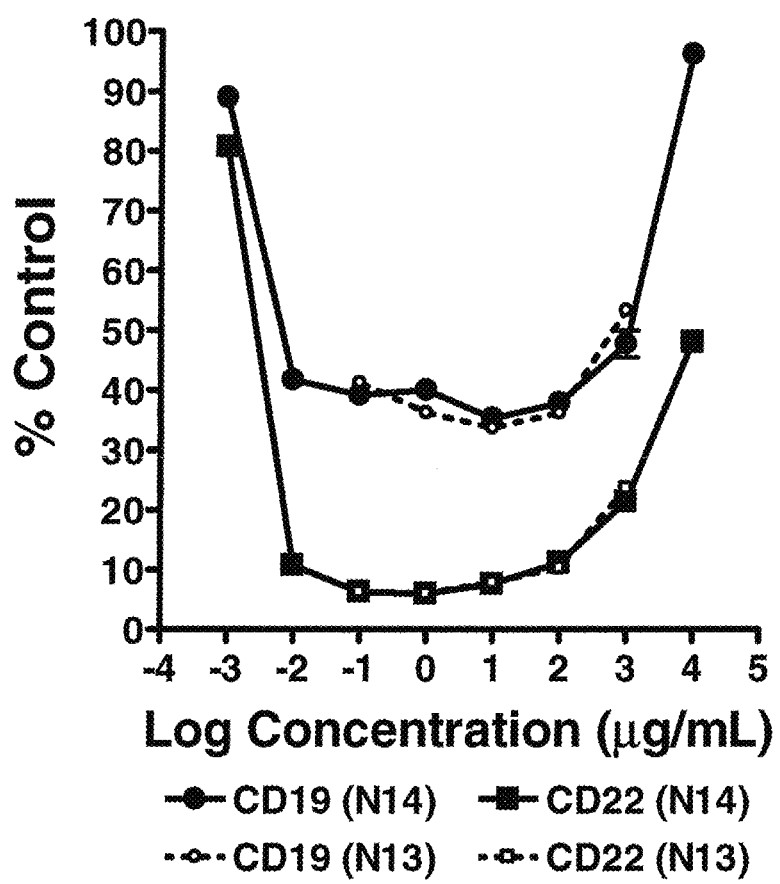
FIG. 8. PBMCs from two normal donors (N13 and N14) were treated overnight with epratuzumab or hMN-14 at varied concentrations (1 ng/mL-10 mg/mL). The B cell surface levels of CD19, CD21, CD22 and CD79b are shown as the % mean fluorescence intensity of the isotype control (hMN-14) treatment at the same protein concentration except for the 10 mg/mL epratuzumab, which was derived using 1 mg/mL hMN-14 as control. Error bars, Std. Dev.

The effect of epratuzumab on the cell surface levels of CD19, CD21, CD22 and CD79b was compared using the standard (10 μg/mL) concentration with a 100-fold higher concentration (1 mg/mL). An additional treatment included 10 μg/mL epratuzumab combined with 1 mg/mL hMN-14. Compared to the lower concentration of epratuzumab (10 μg/mL), the higher concentration (1 mg/mL) resulted in significantly (P<0.02) less reduction in CD22, CD19, CD21 and CD79b (FIG. 7). Competition with high concentration (1 mg/mL) hMN-14 significantly (P<0.003) reduced the effect of epratuzumab (10 μg/mL) on CD22 and CD19, but to a lesser extent than high-dose epratuzumab. A titration experiment, where normal PBMCs were incubated overnight with epratuzumab at concentrations ranging from 0.1-1000 μg/mL, confirmed that doses approaching 1 mg/mL dampened the effect (FIG. 8, donor N13, dashed curves). A second titration covering 8 logs (1 ng/mL-10 mg/mL) produced a classic U-shaped curve with substantial dampening at concentrations lower than 10 ng/mL or greater than 1 mg/mL (FIG. 8, donor N14, solid curves). The reduction of both CD22 and CD19 on B cells within PBMCs was similar over a wide concentration range (10 ng/mL-100 μg/mL) of epratuzumab.

Example 4

The Fc is Required for Trogocytosis

Figure 9:
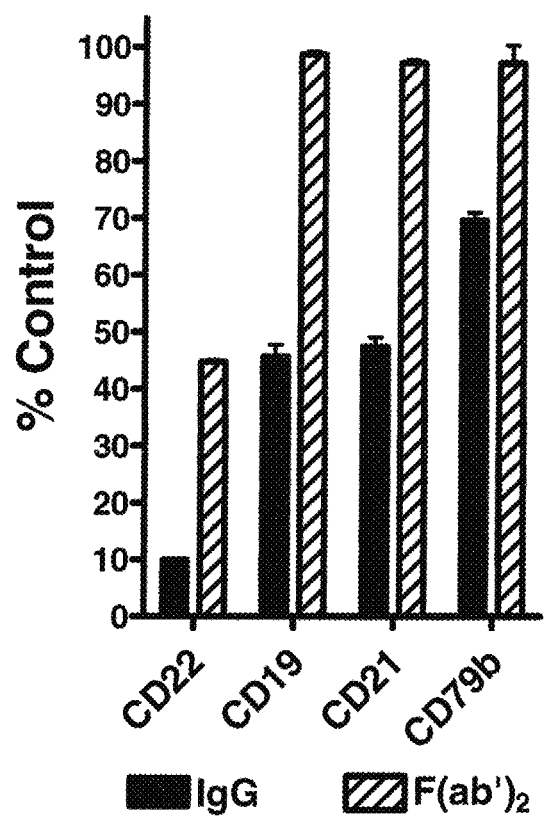
FIG. 9. PBMCs were treated with whole IgG or an F(ab')$_2$ fragment of epratuzumab at 10 µg/mL. The % mean fluorescence intensity of the isotype control (hMN-14) treatment at the same protein concentration is shown. Error bars, Std. Dev.

An F(ab')$_2$ fragment of epratuzumab, which was prepared by pepsin digestion, reduced CD22 moderately (45% control), compared to the full IgG (10% control), and had no effect on CD19, CD21 and CD79b (FIG. 9). The loss of CD22 can be attributed to internalization of the antibody/antigen complex, which is a well established phenomenon associated with epratuzumab, and not due to trogocytosis. That CD19, CD21 and CD79 are not affected by the F(ab')$_2$ indicates that no trogocytosis is induced by the Fc-lacking antibody fragment. A similar finding was observed when PBMCs from lupus patients were used instead of from healthy donors (Example 10).

Example 5

Effector Cells are Required for Epratuzumab-Induced Trogocytosis

Figure 10:
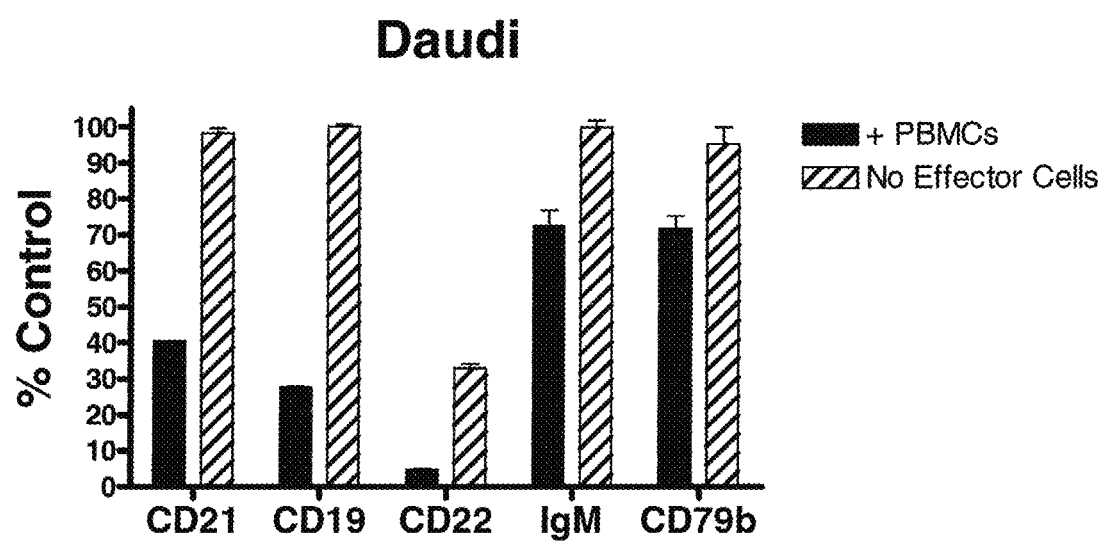
FIG. 10. Daudi human Burkitt lymphoma cells (1×10$^5$ cells) were treated overnight with 10 µg/mL epratuzumab or an isotype control mAb (hMN-14) in the presence, or absence, of PBMCs (1×10$^6$). The plot is shown as the % mean fluorescence intensity of the isotype control treatment. Error bars, Std. Dev.
Figure 11:
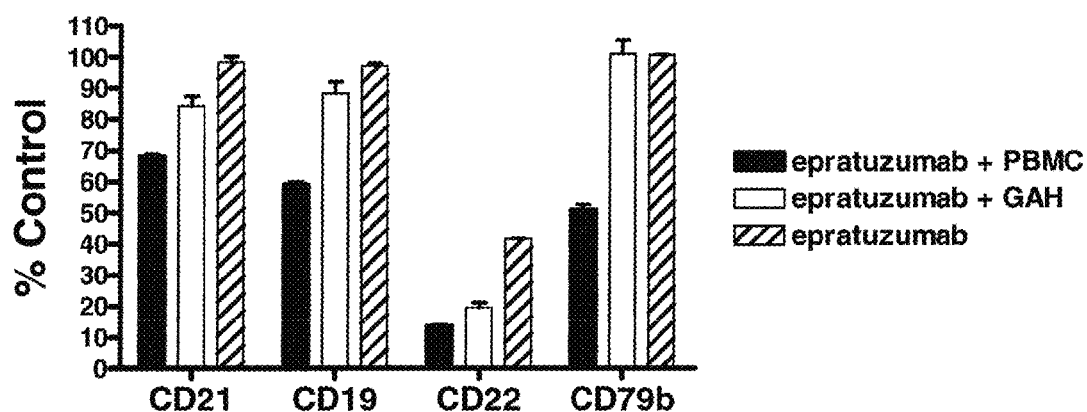
FIG. 11. Raji human Burkitt lymphoma cells (1×10$^5$ cells) were treated overnight with 10 µg/mL epratuzumab or an isotype control mAb (hMN-14) in the presence, or absence, of PBMCs ($1 \times 10^6$) or goat-anti-human IgG (20 µg/mL) as a crosslinking second antibody. The plot is shown as the % mean fluorescence intensity of the isotype control treatment. Error bars, Std. Dev.

B cell lymphoma cell lines were used as "isolated B cells" that were evaluated for epratuzumab induced trogocytosis. In vitro, epratuzumab induced an intermediate reduction (33% control) of CD22 on the surface of isolated Daudi Burkitt lymphoma cells, and did not affect the levels of other markers (FIG. 10). In an ex vivo setting, where Daudi were spiked into PBMCs from a healthy donor, epratuzumab minimized CD22 (<5% control) and significantly (P<0.0001) reduced CD19 (28% control), CD21 (40% control), CD79b (72% control) and surface IgM (73% control). Similar results were obtained with Raji lymphoma cells, where CD19, CD21 and CD79b were diminished by epratuzumab only in the presence of PBMCs (FIG. 11). The addition of a crosslinking second antibody resulted in only a modest reduction of CD19, CD21 and CD79b. That the effect only was observed in the presence of PBMCs, and it was not accomplished in the presence of PBMCs with a F(ab')$_2$ fragment (Example 4) or with a crosslinking second antibody in place of PBMCs, indicates that effector cells bearing Fc receptors are involved in the epratuzumab-induced trogocytosis process.

Example 6

Monocytes, but not T Cells can Modulate Epratuzumab-Induced Trogocytosis

Figure 12:
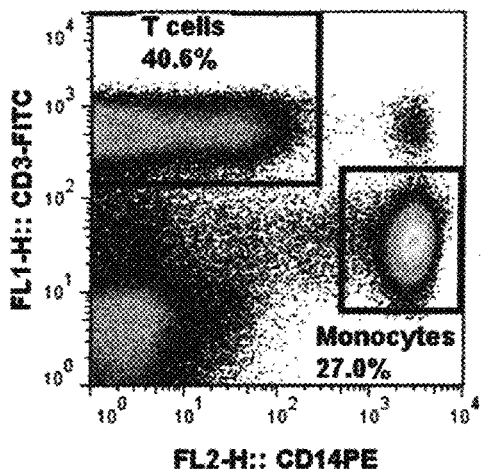
FIG. 12. Gating of monocytes and T cells with anti-CD3 and anti-CD14 from PBMCs (top), T cell-depleted PBMCs (middle) and monocyte-depleted PBMCs (bottom).
Figure 12:
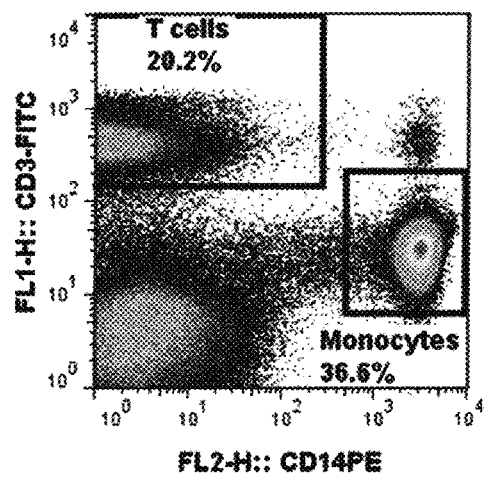
Figure 12:
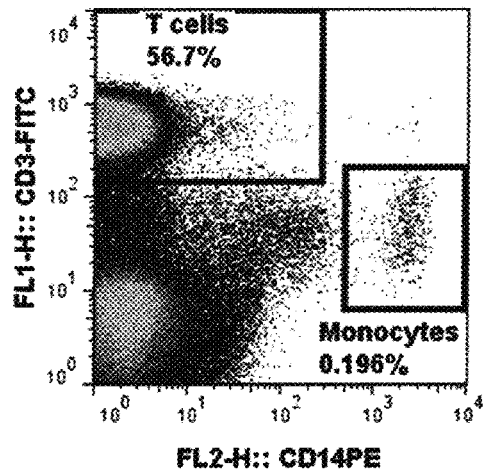
Figure 13:
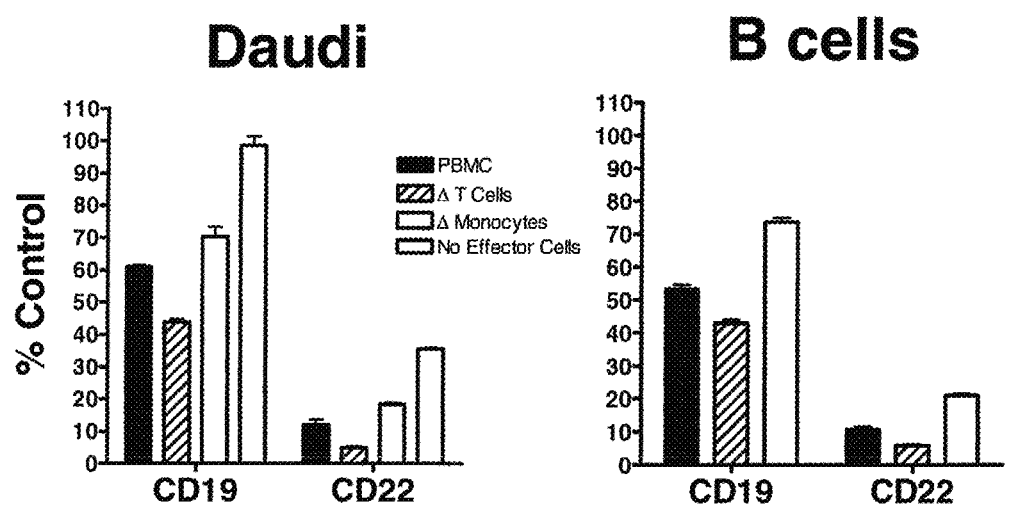
FIG. 13. Epratuzumab-induced reduction of CD19 and CD22 with monocytes. Daudi cells ($1 \times 10^5$) were mixed with effector cells ($1 \times 10^6$) comprising PBMCs, T cell depleted-PBMCs or monocyte-depleted PBMCs, which were each derived from the same donor. The cell mixtures were incubated overnight with 10 µg/mL epratuzumab or an isotype control mAb (hMN-14). The level of CD19 and CD22 on the surface of Daudi (A) and the intrinsic B cells (B) were measured by flow cytometry and plotted as the % mean fluorescence intensity of the isotype control treatment.
Figure 14:
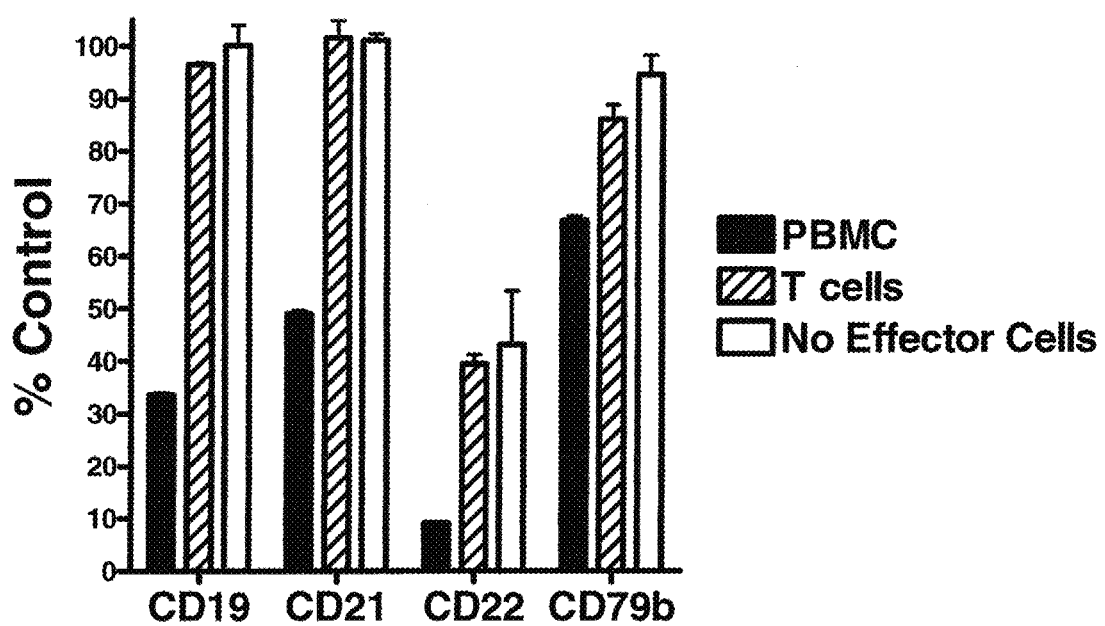
FIG. 14. Purified T cells do not participate in epratuzumab-induced trogocytosis. Daudi cells ($1 \times 10^5$) were mixed with $1 \times 10^6$ PBMCs or purified T cells, or without effector cells and treated overnight with 10 µg/mL epratuzumab or an isotype control mAb (hMN-14). The levels of CD19, CD21, CD22 and CD79b on the surface of Daudi was measured by flow cytometry and plotted as the % mean fluorescence intensity of the isotype control treatment.
Figure 15:
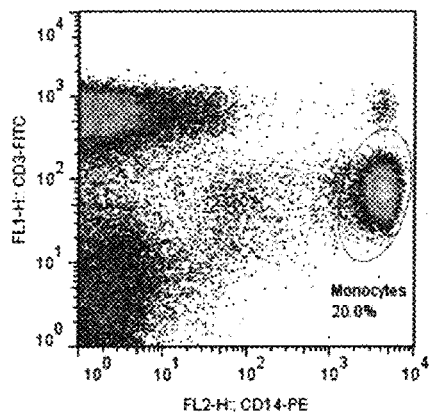
FIG. 15. Gating of monocytes with anti-CD3 and anti-CD14 from PBMCs (top), monocyte-depleted PBMCs (middle) and purified monocytes (bottom).
Figure 15:
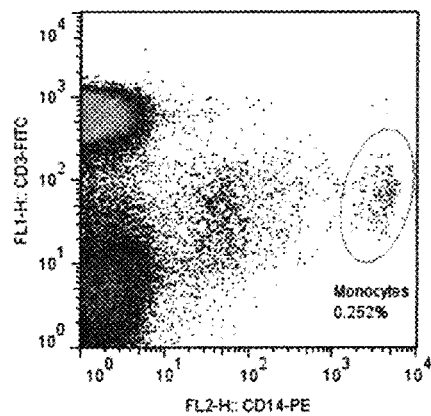
Figure 15:
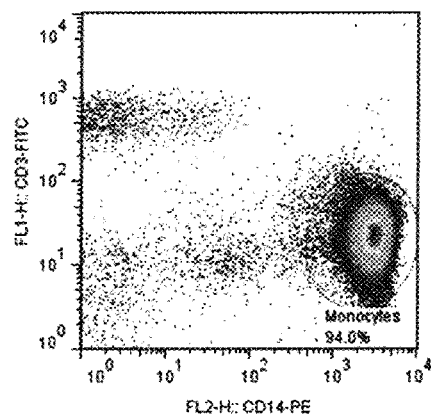
Figure 16:
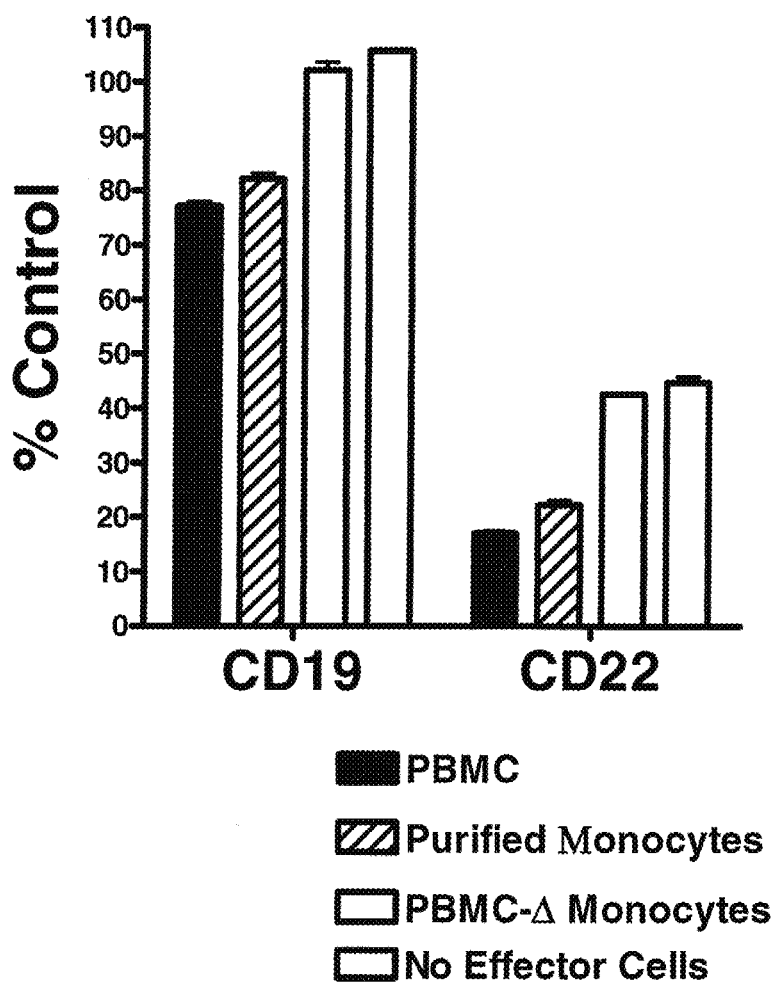
FIG. 16. Daudi cells ($1 \times 10^5$) were mixed with PBMCs ($1 \times 10^6$), monocyte-depleted PBMCs ($1 \times 10^6$) or purified monocytes ($5 \times 10^5$), which were each derived from the same donor. The cell mixtures were incubated overnight with 10 µg/mL epratuzumab or an isotype control mAb (hMN-14). The level of CD19 and CD22 on the surface of Daudi were measured by flow and plotted as the % mean fluorescence intensity of the isotype control treatment.

Combined, T cells and monocytes comprise approximately 70-80% of the total PBMCs. The ability of PBMC fractions, which were depleted of either T cells or monocytes using MACS separation technology (Miltenyi Biotec) with magnetically labeled microbeads in an LS or MS column, were evaluated for epratuzumab-induced reduction of CD22 and CD19 on Daudi and normal B cells. For this experiment the ratio of total effector cells to Daudi was held constant. Therefore, removal of a specific cell type resulted in increased numbers of the remaining cell types (FIG. 12). Depletion of T cells was only 50% efficient; however, this resulted in a 10% increase in monocytes and other cell types. The T-cell-depleted PBMCs were significantly more active than total PBMCs, indicating that T cells are not involved (FIG. 13). Indeed, purified T cells were not capable of affecting the epratuzumab-induced reduction of CD19 or CD21 on Daudi (FIG. 14). Conversely, depletion of monocytes, which was 99% efficient (FIG. 12), significantly dampened the reduction of both CD19 and CD22 on either Daudi or B cells (FIG. 13), implicating the involvement of monocytes. That there was appreciable reduction of CD19 with the monocyte-depleted PBMCs, suggests the participation of additional cell types. In a subsequent experiment, purified monocytes (94%, FIG. 15) induced a similar decrease in CD19 as the whole PBMCs, whereas the remaining monocyte-depleted PBMCs had minimal effect, comparable to the levels measured without effector cells (FIG. 16). A similar pattern was observed for CD22. This particular donor gave relatively weak activity (25% reduction in CD19) compared to most others, where we have typically observed a 40-60% reduction in CD19. Nonetheless, the results support the key role of monocytes among PBMCs.

Example 7

Epratuzumab-Induced Trogocytosis with Monocytes

Figure 17:
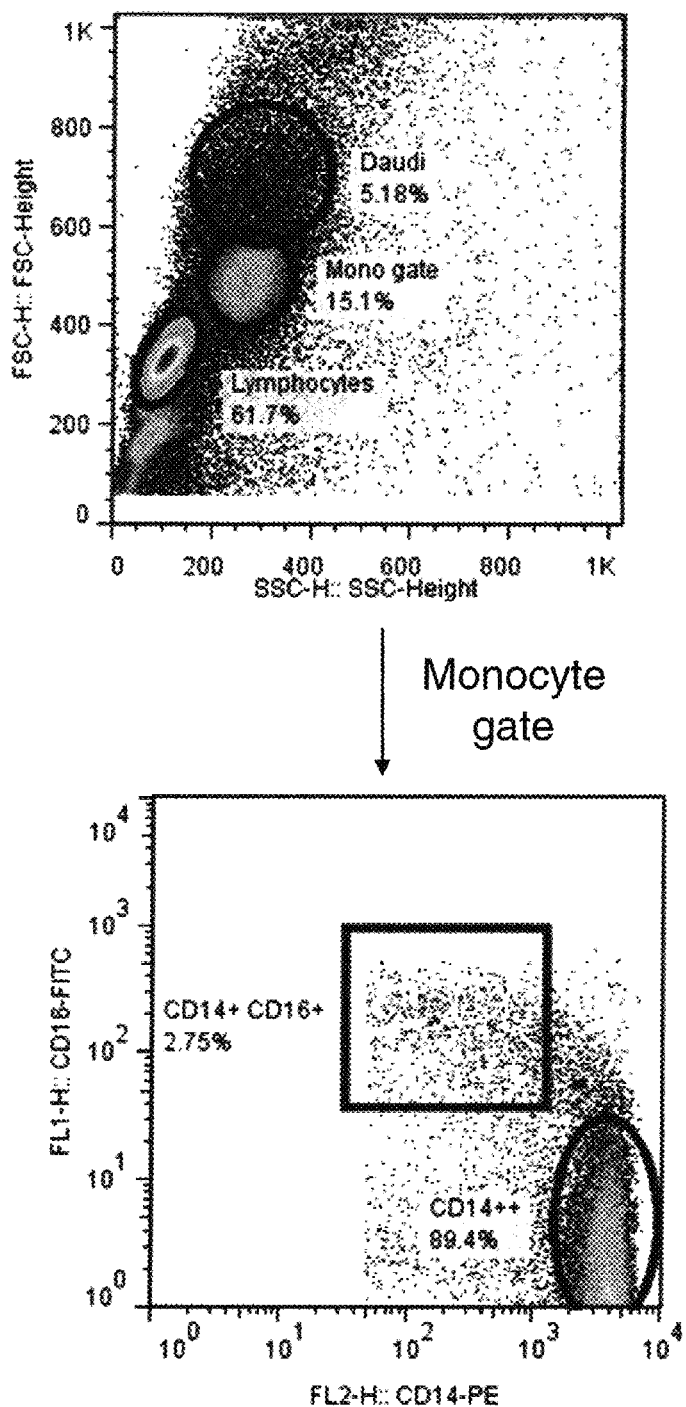
FIG. 17. Gating of monocytes from PBMCs. The monocyte gate (top) was further separated into CD14++ and CD14+CD16+ sub-populations (bottom).
Figure 18:
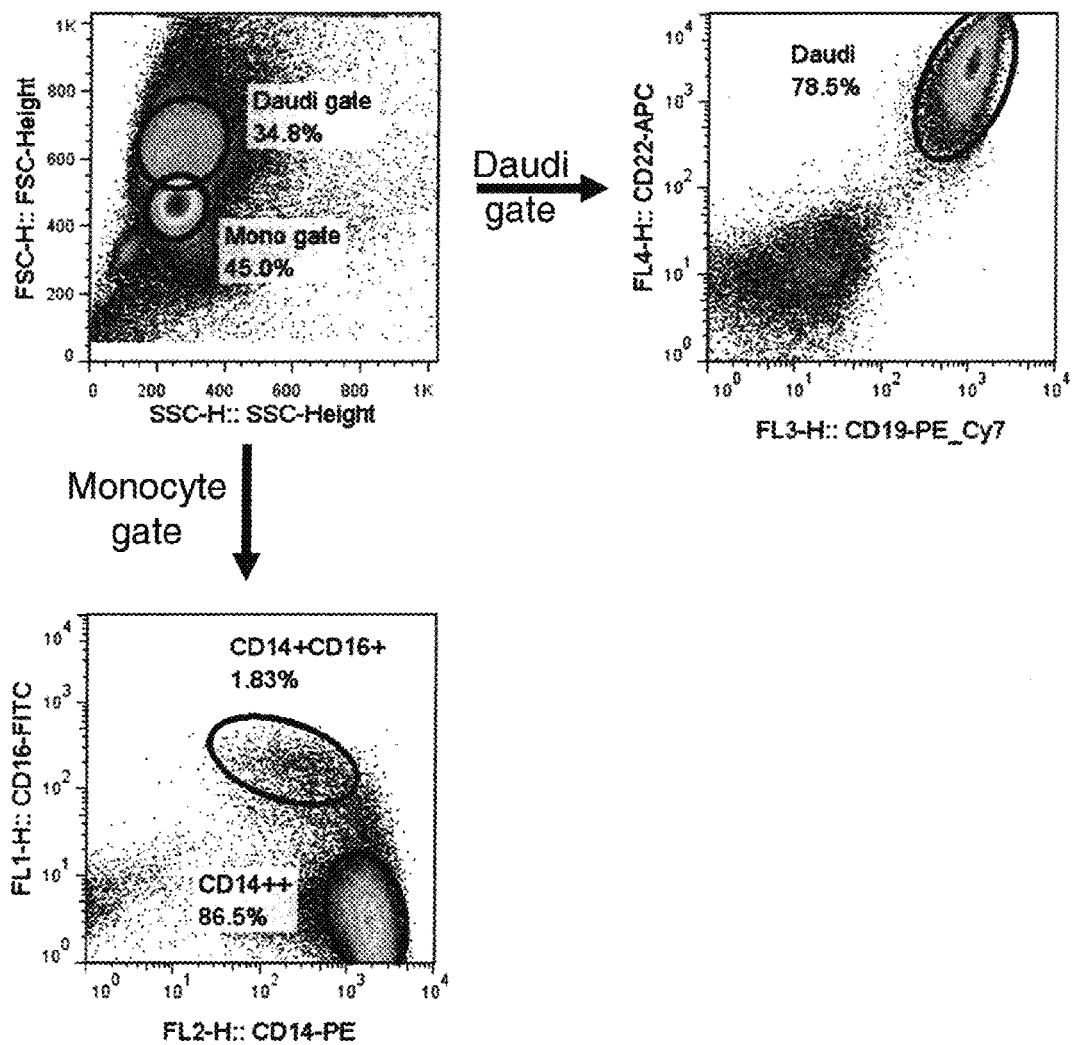
FIG. 18. (Top left) Gating by scattering from a mixture of purified monocytes and Daudi. (Top right) The Daudi cells were further identified as CD19+CD22+ cells in the Daudi gate. (Bottom) The monocyte gate was further separated into CD14++ and CD14+CD16+ sub-populations.
Figure 19:
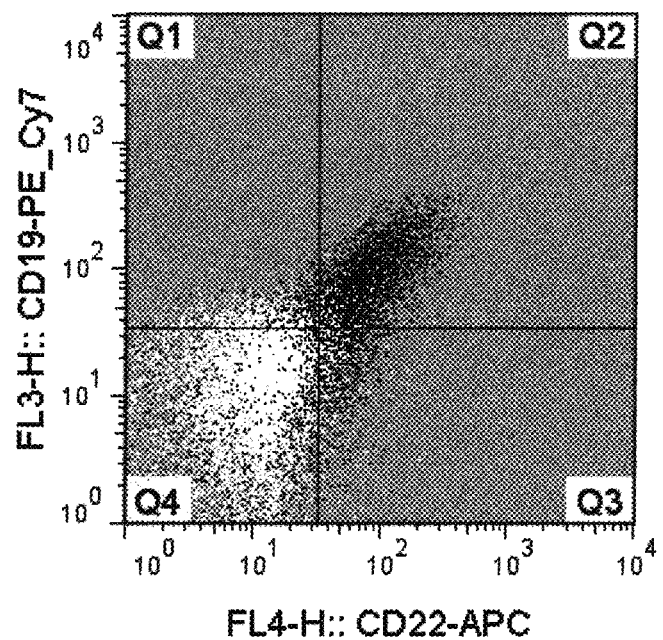
FIG. 19. Epratuzumab-induced trogocytosis with monocytes. Daudi cells were mixed with purified monocytes 1:1 and treated for 1 h with epratuzumab (black dots) or hMN-14 (white dots) before analysis by flow cytometry. The monocyte gate determined by forward vs. side scattering was further gated with anti-CD14.
Figure 20:
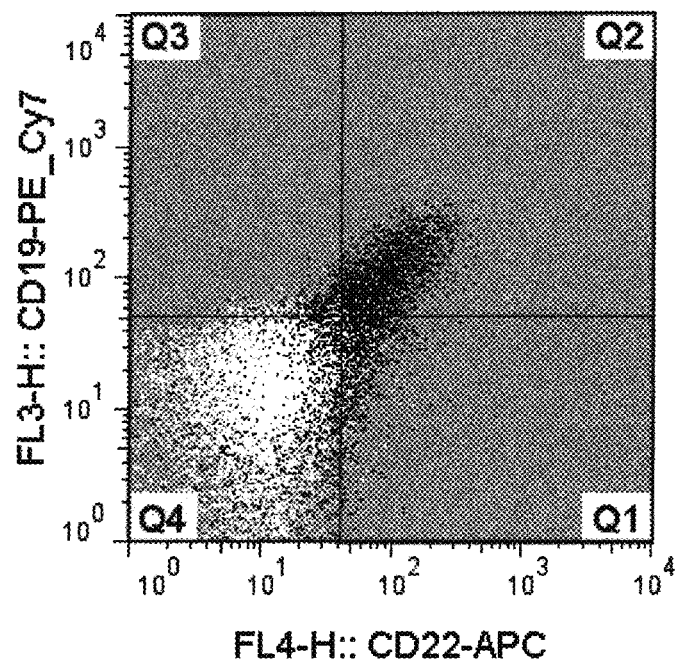
FIG. 20. Daudi cells were mixed with purified monocytes 1:1 and treated for 1 h with epratuzumab (black dots) or hMN-14 (white dots) before analysis by flow cytometry. The monocyte gate determined by forward vs. side scattering was further separated into $CD14^{++}$ (A) and $CD14^+CD16^+$ (B) monocyte populations, which were each evaluated for CD19 and CD22 levels.
Figure 20:
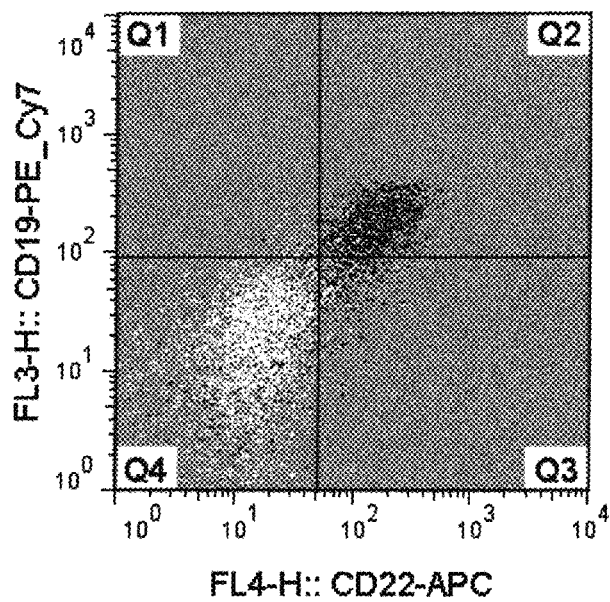
Figure 21:
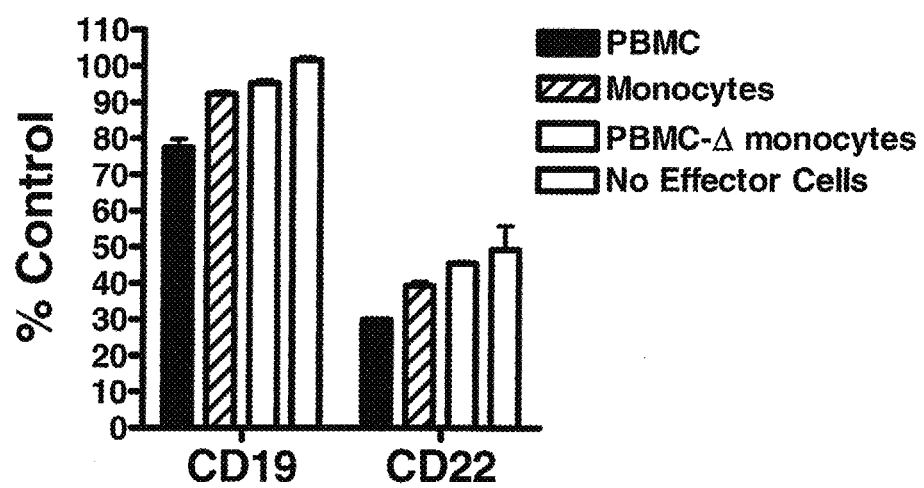
FIG. 21. The Daudi cells ($CD19^+$ cells in the Daudi gate) were analyzed for CD19 and CD22 levels following a 1-hour epratuzumab treatment with PBMCs, purified monocytes or monocyte-depleted PBMCs. The level of CD19 and CD22 on the surface of Daudi were measured by flow and plotted as the % mean fluorescence intensity of the isotype control treatment.

Trogocytosis involves the transfer of membrane components from one cell to another. To determine if the loss of surface antigen on B cells is due to their transfer to effector cells (trogocytosis), Daudi cells were mixed with PBMCs (FIG. 17), purified monocytes (FIG. 18) or monocyte-depleted PBMCs, and treated with epratuzumab or the isotype control for 1 h. Daudi, monocyte and lymphocyte populations were gated by foreword vs. side scattering. When mixed with Daudi cells and treated with epratuzumab, but not the isotype control mAb, purified monocytes (CD14 positive cells) stained positive for either CD22 (56.6% positive) and CD19 (52.4% positive), with 44% positive for both (FIG. 19). Treatment with an isotype control mAb resulted in only 1.6% double positive monocytes. The monocytes were further gated into CD14$^{++}$ (~90%) and CD14$^+$CD16$^+$ (~10%) subpopulations (FIG. 17 and FIG. 18). The CD14$^+$CD16$^+$ monocytes (FIG. 20A) exhibited more activity (66.4% CD19$^+$ CD22$^+$) compared to the more abundant CD14$^{++}$ (31.4%) cells (FIG. 20B). Even after only 1 h, CD19 and CD22 were specifically reduced from Daudi cells when treated with epratuzumab in the presence of PBMCs or purified monocytes (FIG. 21). These results demonstrate that CD19 and CD22 are transferred from Daudi cells to both populations of monocytes.

Example 8

Epratuzumab-Induced Trogocytosis with NK Cells

Figure 22:
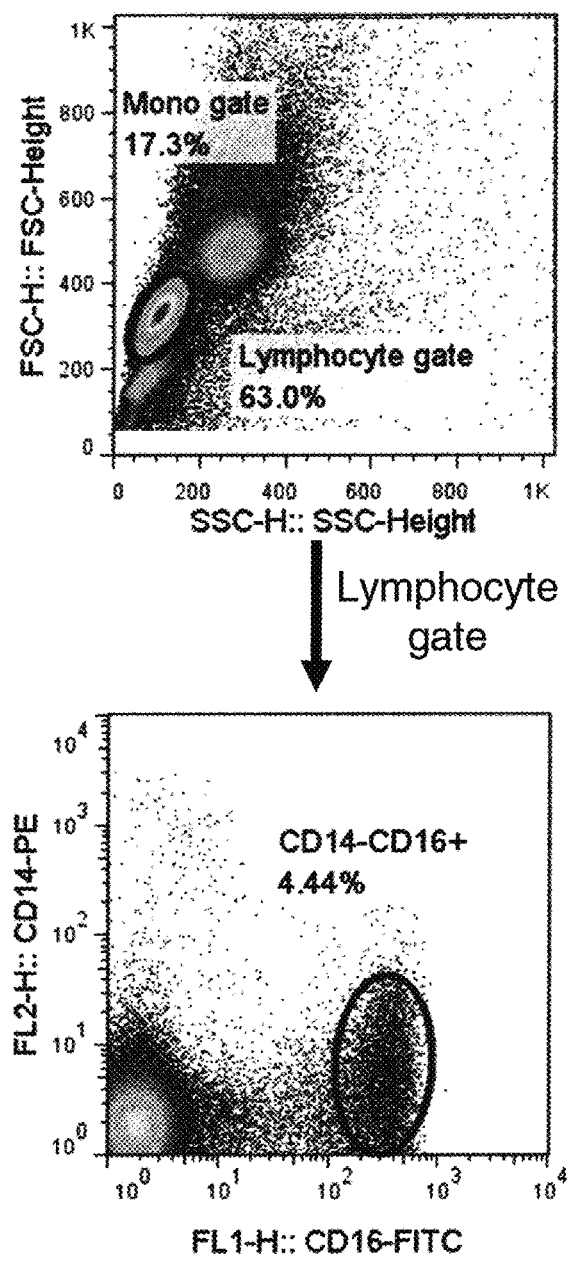
FIG. 22. (Top) Gating by scattering from a mixture of PBMCs and Daudi. (Bottom) The lymphocyte gate was further separated with CD14 and CD16 staining to identify NK cells.
Figure 23:
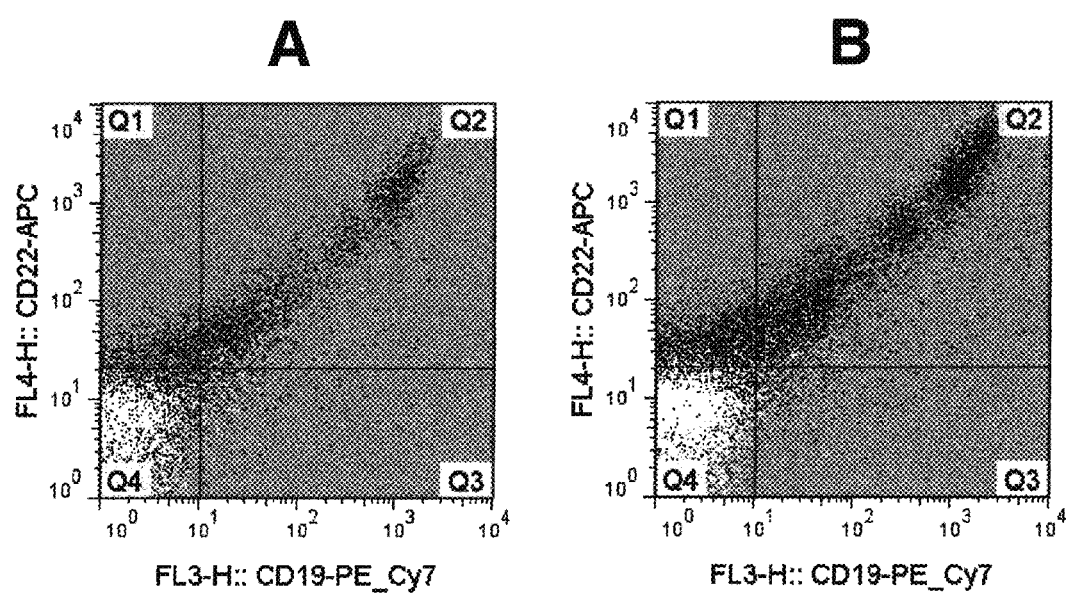
FIG. 23. Daudi cells were mixed with PBMCs 1:5 (A), monocyte-depleted PBMCs 1:5 (B) and treated for 1 h with epratuzumab (black dots) or hMN-14 (white dots) before analysis by flow cytometry. The NK cells were identified as $CD14^-CD16^+$ cells in the lymphocyte gate, which were evaluated for the levels of CD19 and CD22.

CD19 and CD22 were significantly reduced from Daudi cells in monocyte-depleted PBMCs (FIG. 21), suggesting the involvement of effector cells in addition to monocytes. NK cells, which express FcγRIII (CD16), are identified among PBMCs by flow cytometry as CD14-CD16+ cells located in the lymphocyte (forward vs. side scatter) gate. Using the Daudi/PBMC and Daudi/monocyte-depleted PBMC mixtures from Example 7, the lymphocyte gate was further gated for CD14 and CD16 to identify CD14$^-$CD16$^+$NK cells (FIG. 22). NK cells potently acquired CD19 and CD22 when either PBMCs (FIG. 23A) or monocyte-depleted PBMCs (FIG. 23B) were mixed with Daudi and epratuzumab. These results indicate that NK cells can function in epratuzumab-induced trogocytosis.

Example 9

Epratuzumab-Induced Trogocytosis with Granulocytes

Figure 24:
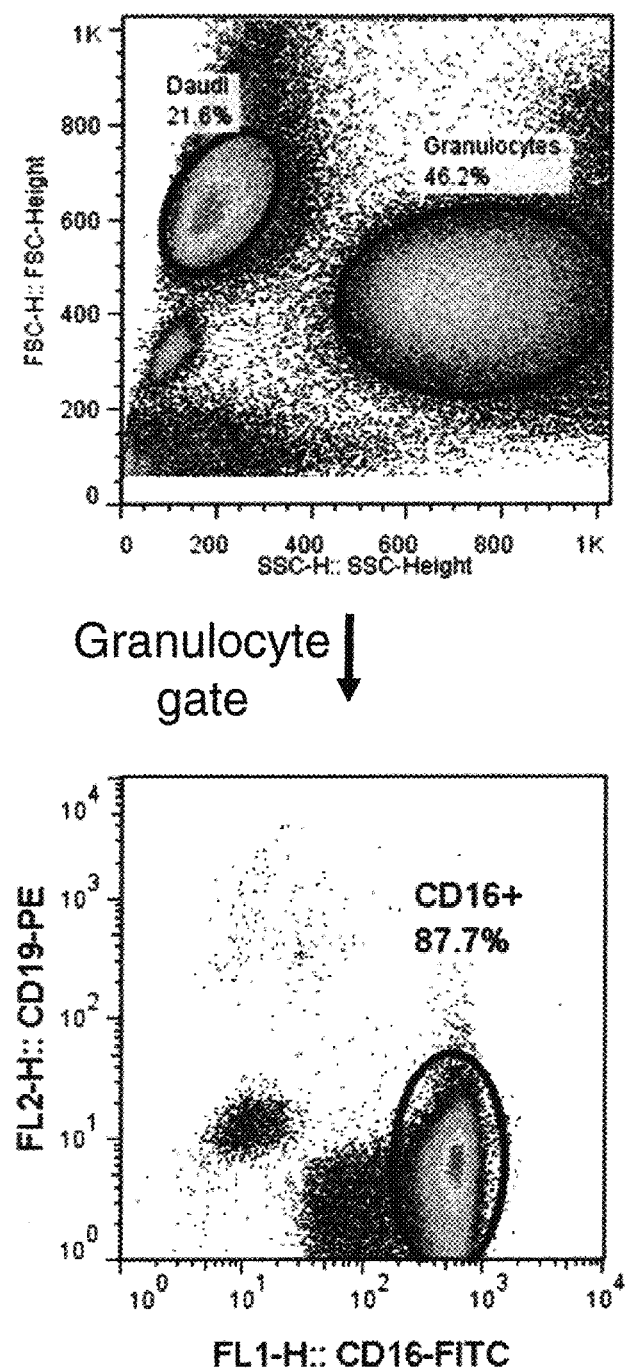
FIG. 24. Gating of granulocytes mixed with Daudi first by forward vs. side scatter (Top) followed by anti-CD16 staining.
Figure 25:
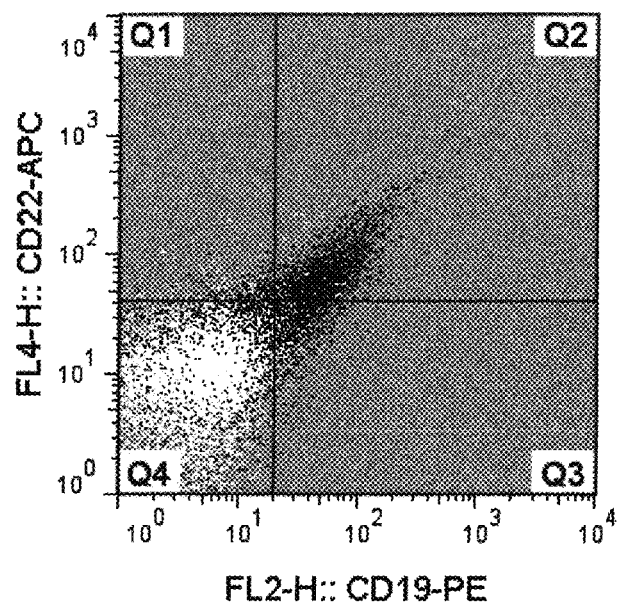
FIG. 25. Daudi cells were mixed with purified granulocytes 1:2 and treated for 1 h with epratuzumab (black dots) or hMN-14 (white dots) before analysis by flow cytometry. The granulocyte gate was further refined for $CD16^+$ cells and evaluated for CD19 (A and B), CD22 (A) and CD79b (B) levels.
Figure 25:
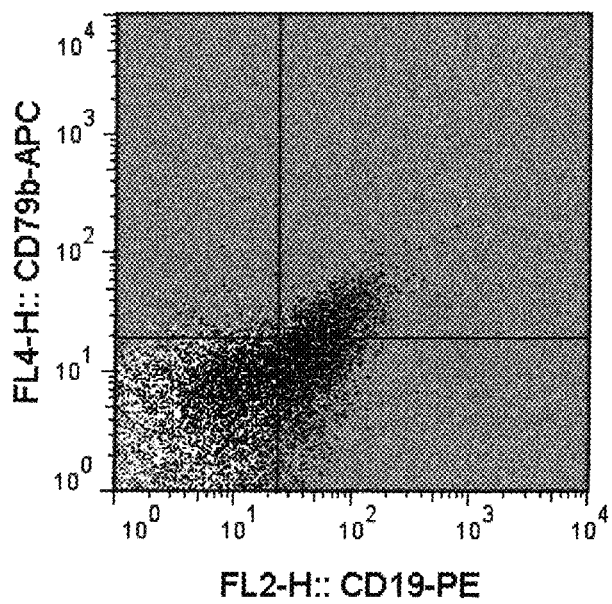
Figure 26:
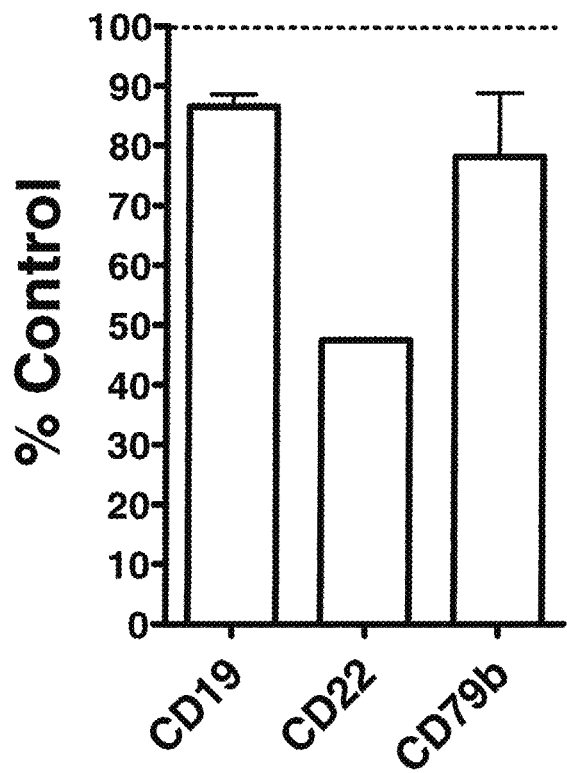
FIG. 26. Daudi cells were mixed with purified granulocytes 1:2 and treated for 1 h with epratuzumab or hMN-14 before analysis by flow cytometry. The Daudi cells ($CD19^+$ cells in the Daudi gate) were analyzed for CD19, CD22 and CD79b levels and graphed as the % mean fluorescence intensity of the isotype control treatment.

Granulocytes, or polymorphonuclear cells, which comprise mostly neutrophils, are separated from the PBMCs during processing of whole blood. Granulocytes, which express FcγRIII (CD16), were assessed for their ability to participate in trogocytosis when mixed with Daudi cells and epratuzumab. Granulocytes were readily gated from the Daudi cells by side scattering and CD16 (FIG. 24). When mixed with Daudi cells and treated with epratuzumab, but not the isotype control mAb, granulocytes stained positive for CD22 (30.4% positive), CD19 (40.9% positive) and CD79b (13.7% positive) (FIG. 25). Following the 1-h incubation, a significant reduction on Daudi of each antigen indicates their transfer from Daudi to granulocytes (FIG. 26).

TABLE 8

Trogocytosis of CD19 and CD22 from Daudi to monocytes, NK cells and granulocytes following treatment with epratuzumab.

| Cells | mAb | % CD19+ | % CD22+ | % CD19+CD22+ |
|---|---|---|---|---|
| All Monocytes | epratuzumab | 52.4 | 56.6 | 44.4 |
|  | hMN-14 | 10.1 | 5.3 | 1.6 |
| CD14+CD16+ Monocytes | epratuzumab | 67.5 | 81.6 | 66.4 |
|  | hMN-14 | 4.3 | 6.7 | 2.3 |
| CD14++ Monocytes | epratuzumab | 35.4 | 48.9 | 31.4 |
|  | hMN-14 | 2.1 | 2.6 | 0.5 |
| CD14−CD16+ NK | epratuzumab | 46.3 | 58.0 | 43.6 |
|  | hMN-14 | 3.7 | 4.7 | 2.4 |
| Granulocytes | epratuzumab | 40.9 | 30.4 | 26.8 |
|  | hMN-14 | 2.2 | 1.9 | 0.5 |

Purified monocytes, monocyte-depleted PBMCs (CD14−CD16+ NK cells), or granulocytes were mixed with an equal number of Daudi cells and treated with 10 μg/mL epratuzumab or hMN-14 (anti-CEA mAb as control) for 1 h.

Example 10

Ex Vivo Trogocytosis with SLE Patient PBMCs

Figure 27:
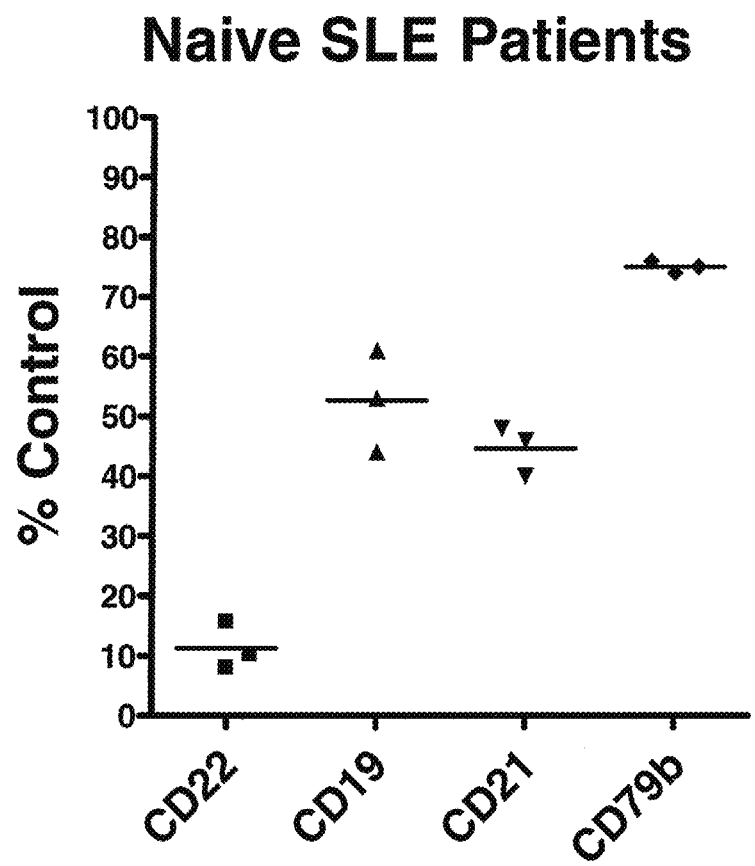
FIG. 27. PBMCs were isolated from blood specimens of three naive SLE patients and treated overnight with 10 µg/mL epratuzumab or hMN-14. The relative levels of CD19, CD22, CD21 and CD79b on B cells post-treatment were measured by flow cytometry and graphed as the % mean fluorescence intensity of the isotype control treatment.
Figure 28:
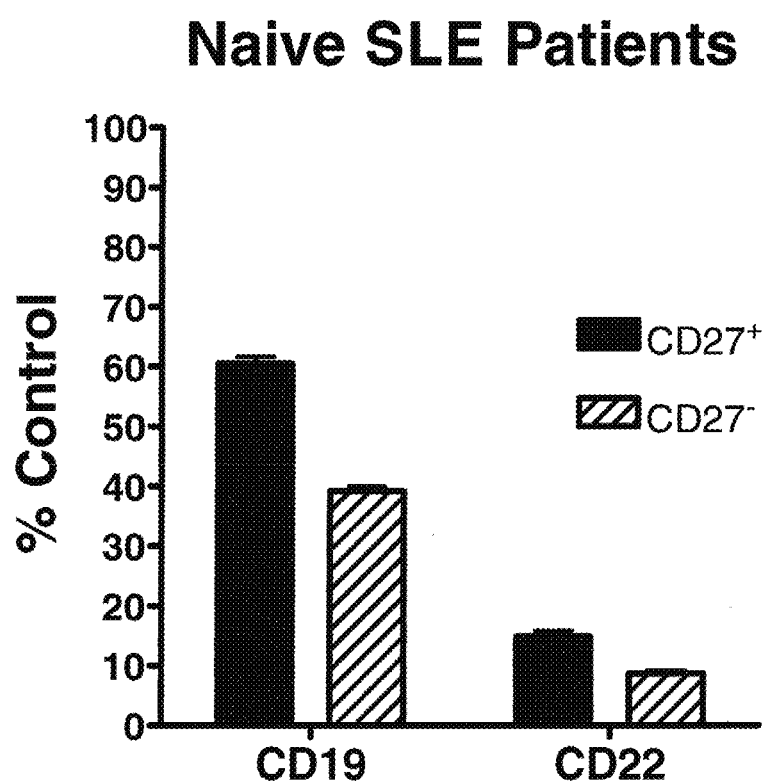
FIG. 28. PBMCs were isolated from blood specimens of three naive SLE patients and treated overnight with 10 µg/mL epratuzumab or hMN-14. B cells were gated further into $CD27^+$ and $CD27^-$ populations before analysis. The relative levels of CD19 and CD22 on the B cell sub-populations post-treatment were measured by flow cytometry and graphed as the % mean fluorescence intensity of the isotype control treatment.
Figure 29:
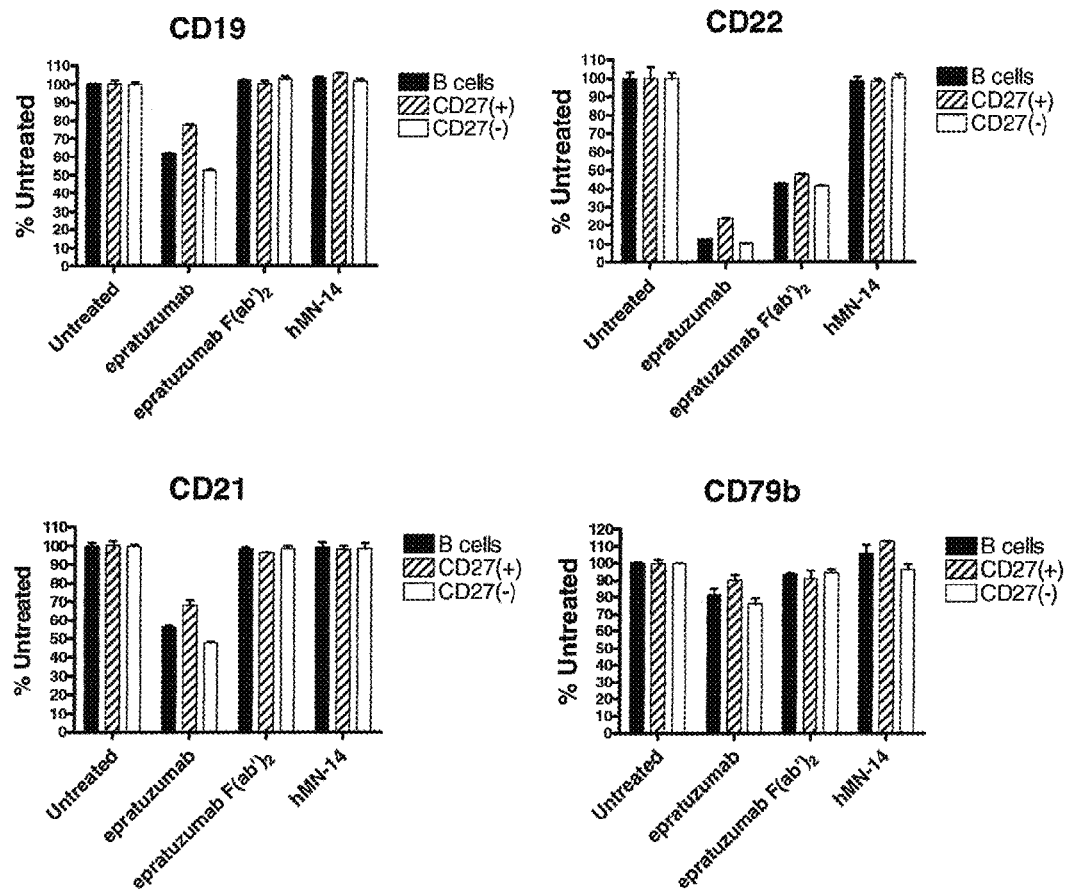
FIG. 29. PBMCs were isolated from blood specimens of naive SLE patients and treated overnight with 10 µg/mL epratuzumab, an $F(ab')_2$ of epratuzumab or hMN-14. B cells were gated further into $CD27^+$ and $CD27^-$ populations before analysis. The figure shows an example from one naive SLE patient. The relative levels of CD19, CD22, CD21 and CD79b on the B cell sub-populations post-treatment were measured by flow cytometry and graphed as the % mean fluorescence intensity of untreated PBMCs.

PBMCs were isolated from blood specimens of systemic lupus erythematosus (SLE, lupus) patients, who had yet to receive any therapy for their disease (naïve), and treated ex vivo with epratuzumab, using the same method that was applied to PBMCs from healthy donors. PBMCs of naive SLE patients responded similarly to healthy PBMCs (as in Example 1), where CD22, CD19, CD21 and CD79b on the surface of B cells were reduced to 11±4, 53±8, 45±4 and 75±1% control, respectively (FIG. 27). Also similar to the results from normal donor PBMCs, CD27− naive B cells were more responsive than CD27+ memory B cells (FIG. 28), and, a F(ab')$_2$ fragment of epratuzumab did not induce the reduction of CD19, CD21 or CD79b (FIG. 29). PBMCs isolated from blood specimens of SLE patients who currently were on epratuzumab immunotherapy had minimal response to the ex vivo treatment with epratuzumab (not shown), presumably due to low levels of CD22 on their B cells, resulting from therapy.

Example 11

Figure 30:
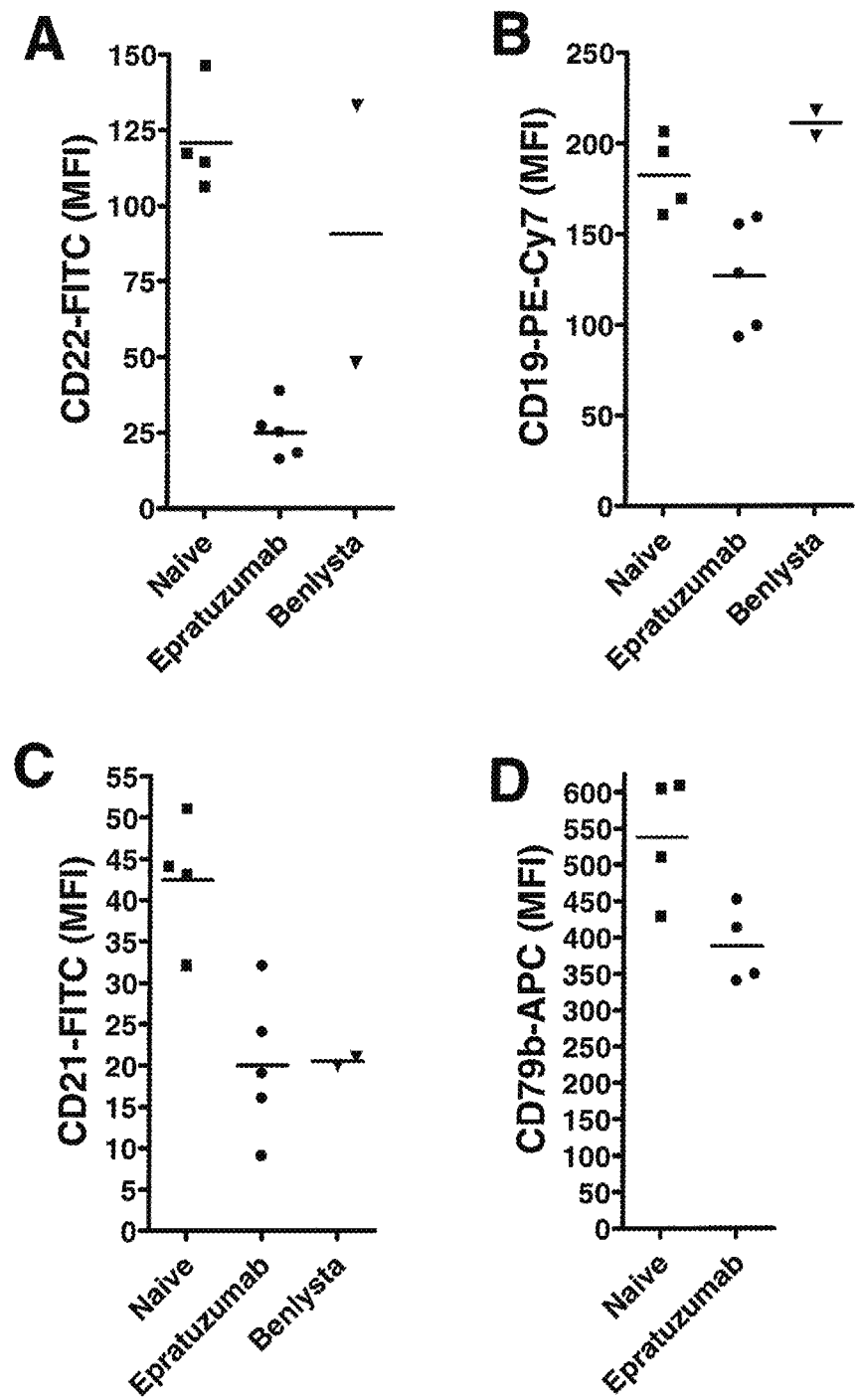
FIG. 30. The MFI levels of CD22 (A), CD19 (B), CD21 (C) and CD79b (D) were measured by flow cytometry on B cells gated from PBMCs that were isolated from four SLE patients who had yet to receive any treatment (naïve), five patients on active immunotherapy with epratuzumab and two patients on immunotherapy with BENLYSTA®. Each point represents an individual patient sample.

Surface Levels of CD19, CD21, CD22 and CD79b on SLE Patient B Cells on Epratuzumab Immunotherapy The relative levels of CD22, CD19, CD21 and CD79b on B cells from five SLE patients who were receiving epratuzumab immunotherapy, were compared the results obtained from four naive lupus patients and two receiving BENLYSTA®, using identical conditions (Table 9). Only one of the epratuzumab group (S7) had a markedly reduced B cell count; however, this patient was also taking prednisone and methotrexate. Each of the four patients on epratuzumab without methotrexate had B cell counts in the same range as the naive patients. Both BENLYSTA® patients had low B cell counts. As expected, CD22 was significantly (P<0.0001) lower (>80%) on the B cells of epratuzumab-treated patients (FIG. 30A). Notably, CD19, CD21 and CD79b were each significantly (P<0.02) lower for the epratuzumab group (FIG. 30B-D). We also compared the results for the epratuzumab patient specimens with those of two patients who were receiving immunotherapy with BENLYSTA®. Although the sample size is small, both CD19 and CD22 levels were significantly (P<0.05) lower on the B cells of patients on epratuzumab compared to BENLYSTA®. The level of CD21 was similarly low for the epratuzumab and BENLYSTA® patient B cells. Because anti-CD79b-PE (instead of APC) was used to measure CD79b on B cells from BENLYSTA® patients, we could only compare these results with one epratuzumab patient specimen, which was measured similarly. The CD79-PE MFI was greater for each of the BENLYSTA® specimens (MFI=425 and 470) compared to that of the epratuzumab sample (MFI=186).

TABLE 9

Comparison of B cells from lupus patients

| Patient | Treatment | % B cell in lymph-gate | CD19 (PE-Cy7) | CD21 (FITC) | CD22 (FITC) | CD79b (APC) |
|---|---|---|---|---|---|---|
| S7 | E, P, M | 0.5 | 99 | 9 | 16 | 186$^{PE}$ |
| S8 | P, I | 5.0 | 145 | nd | 84 | nd |
| S9 | B | 0.5 | 218 | 21 | 48 | 470$^{PE}$ |
| S10 | B | 0.9 | 204 | 20 | 133 | 425$^{PE}$ |
| S11 | None | 18.0 | 195 | 51 | 106 | 608 |
| S12 | None | 13.1 | 160 | 44 | 114 | 428 |
| S13 | None | 13.3 | 206 | 43 | 117 | 510 |
| S14 | None | 11.1 | 169 | 32 | 146 | 604 |
| S16 | E, P | 8.9 | 128 | 24 | 27 | 452 |
| S17 | E, P | 4.5 | 93 | 16 | 25 | 340 |
| S18 | E, P | 17.6 | 159 | 32 | 18 | 413 |
| S19 | E, P | 20.3 | 155 | 19 | 38 | 349 |

E, epratuzumab;
P, prednisone;
M, methotrexate;
I, Imuran;
B, BENLYSTA ®;
$^{PE}$used instead of APC;
nd, not determined The present studies disclose previously unknown, and potentially important, mechanisms of action of epratuzumab in normal and lupus B cells, as well as B-cell lymphomas, which may be more pertinent to the therapeutic effects of epratuzumab in autoimmune patients. The prominent loss of CD19, CD21, CD20, and CD79b induced by epratuzumab is not only Fc-dependent, but also requires further engagement with FcγR-expressing effector cells present in PBMCs. The findings of reduced levels of CD19 are of particular relevance for the efficacy of epratuzumab in autoimmune diseases, because elevated CD19 has been correlated with susceptibility to SLE in animal models as well as in patients, and loss of CD19 would attenuate activation of B cells by raising the BCR signaling threshold. Based on these findings, the activity of epratuzumab on B cells is two-fold, one via binding to CD22, which also occurs with F(ab')$_2$, and the other via engagement of FcγR-bearing effector cells. Whereas the former leads to internalization of CD22, as well as its phosphorylation with concurrent relocation to lipid rafts (resulting in the activation of tyrosine phosphatase to inhibit the activity of Syk and PLCr2), the latter results in the trogocytosis (shaving) of CD19, among others.

We propose that the consequences of losing CD19 from B cells are as follows. BCR activation upon encountering membrane-bound antigen involves the initial spreading and the subsequent formation of microclusters. Because CD19 is critical for mediating B-cell spreading, CD19-deficient B cells are unable to gather sufficient antigen to trigger B-cell activation. In addition, loss of CD19 on B cells may severely affect the ability of B cells to become activated in response to T cell-dependent antigens. Thus, the epratuzumab-mediated loss of CD19 (and possibly other BCR markers and cell-adhesion molecules) on target B cells may incapacitate such B cells and render them unresponsive to activation by T cell-dependent antigen. In summary, epratuzumab inactivates B cells via the loss of CD19, other BCR constituents, and cell-adhesion molecules that are involved in sustaining B-cell survival, leading to therapeutic control in B-cell-mediated autoimmune diseases. Although targeting B cells with either epratuzumab to CD22 or rituximab to CD20 appears to share a common effect of reducing CD19 by trogocytosis, we are currently investigating whether rituximab has a scope of trogocytosis as broad as epratuzumab. The results also caution that using CD19 as a marker for quantifying B cells by flow cytometry from patients treated with agents that induce CD19 trogocytosis may result in an over-estimation of B-cell depletion.

It has been shown with rituximab administered to chronic lymphocytic leukemia cells that too much antibody results in removal of complexes of rituximab-CD20 from the leukemia cells by trogocytosis to monocytes, and can enable these malignant cells to escape the effects of the antibody by antigenic modulation. It was then found that reducing the dose of therapeutic antibody could limit the extent of trogocytosis and improve the therapeutic effects (Herrera et al., 2006). Based on our present findings, a similar process of antigen shaving (trogocytosis) by anti-CD22 or anti-CD20 antibodies that extends beyond the respective targeted antigens can be implicated in the therapy with epratuzumab or rituximab (or the humanized anti-CD20 mAb, veltuzumab). This could explain the clinical observations that higher doses of epratuzumab administered to SLE or lymphoma patients did not show an improvement in efficacy over the mid-range dose used, because the concentrations of epratuzumab in serum would be in the μM range (150 μg/mL or higher) and could mask the low-affinity FcγR5 on effector cells, thus reducing the likely events of trogocytosis.

Example 12

Administration of Epratuzumab in Systemic Lupus Erythematosus (SLE)

An open-label, single-center study of patients with moderately active SLE (total British Isles Lupus Assessment Group (BILAG) score 6 to 12) is conducted. Patients receive dosages of epratuzumab of 100, 200, 400 and 600 mg subcutaneously (SC) every week for 6 weeks. Evaluations include safety, SLE activity (BILAG), blood levels of B and T cells, human anti-epratuzumab antibody (HAHA) titers, and levels of cell surface CD19, CD20, CD21, CD22 and CD79b on B cells. It is determined that a dosage of 400-600 mg per SC injection results in optimal depletion of B cell CD19, while producing less than 50% depletion of normal B cells. Subsequently, a subcutaneous dose of 400 mg epratuzumab is administered to a new group of patients with moderately active SLE.

Total BILAG scores decrease by at least 50% in all patients, with 92% having decreases continuing to at least 18 weeks. Almost all patients (93%) experience improvement in at least one BILAG B- or C-level disease activity at 6, 10 and 18 weeks. Additionally, 3 patients with multiple BILAG B involvement at baseline have completely resolved all B-level disease activities by 18 weeks. Epratuzumab is well tolerated, with no evidence of immunogenicity or significant changes in T cells, immunoglobulins or autoantibody levels. B-cell levels decrease by an average of 35% at 18 weeks and remain depressed for 6 months post-treatment.

Example 13

Prediction of Epratuzumab Response in Systemic Lupus Erythematosus (SLE)

Another open-label, single-center study of patients with moderately active SLE is conducted. Patients receive a single dose of 400 mg epratuzumab subcutaneously. Blood levels of B and T-cells and levels of cell surface CD19, CD20, CD21, CD22 and CD79b on B cells are determined.

Patients are divided into two groups, based on whether they show a decrease in B-cell CD19 levels above (responders) or below (non-responders) the median response for the group. It is observed that decreased B-cell CD19 levels are correlated with decreases in B-cell CD20, CD21, CD22 and CD79b. Subsequent s.c. administration of 400 mg of epratuzumab occurs every week for 8 weeks and SLE activity (BILAG) is monitored.

The group of responders shows a substantial improvement in BILAG scores compared with the group of non-responders. Three of ten patients in the responders group have completely resolved all BILAG B-level disease activities by 18 weeks, compared with zero of ten patients in the non-responders group. In addition, a significant improvement in total BILAG scores is observed in the responders group compared to the non-responders. It is concluded that trogocytosis (antigen-shaving) of CD19 and other BCR antigens is predictive of therapeutic response to therapy with anti-CD22 antibody in SLE.

Example 14

Administration of Epratuzumab in Hairy Cell Leukemia

Patients with previously untreated or relapsed hairy cell leukemia receive 4 doses of 80, 160, 320 or 640 mg epratuzumab injected s.c. every week or every two weeks. Occasional mild to moderate transient injection reactions are seen with the s.c. injection and no other safety issues are observed. The s.c. epratuzumab exhibits a slow release pattern over several days. Transient B-cell depletion is observed at all dosage levels of epratuzumab. Depletion of B cell surface levels of CD19, CD20, CD21, CD22 and CD79b is observed at a moderate level with 320 mg and at a much higher level at 640 mg epratuzumab.

Objective responses are observed at all dose levels of s.c. epratuzumab, but with particularly high responses of 30% (mostly partial responses) at the dose of 320 mg. All serum samples evaluated for human anti-epratuzumab antibody (HAHA) are negative. Six months after treatment, optimal outcome is observed in the group treated with 320 mg epratuzumab, with decreased response at either higher or lower dosages. It is concluded that under these conditions, 320 mg epratuzumab is the optimum dosage that was used. Monitoring response of BCR levels to therapeutic antibody provides an effective surrogate marker for determining antibody efficacy and is predictive of disease prognosis in response to therapy.

Example 15

Trogocytosis of BCR-Response Modulating Proteins Induced by the RFB4 Anti-CD22 Antibody Trogocytosis of BCR-regulating proteins, including CD19, CD21, CD22 and CD79b is assayed as described in Example 1 in response to exposure to the anti-CD22 antibody RFB4, which binds to a different epitope of CD22 than epratuzumab. Control antibody (hMN-14) is used as described in Example 1. Exposure to RFB4 antibody induces trogocytosis of BCR-regulating proteins, similar to that induced by epratuzumab as disclosed in Example 1. CD27⁻ naive B cells are more responsive to RFB4 compared to CD27⁺ memory B cells. The effect is essentially complete within a few hours. The reductions in surface CD19 and CD21 are not significantly different following 2-h or overnight treatment.

Example 16

Mechanism of Cytotoxicity Induced on Malignant B Cells by Anti-CD22 Antibody (Epratuzumab)

Summary

Epratuzumab has shown activity in patients with non-Hodgkin lymphoma, systemic lupus erythematosus, and Sjögren's syndrome, but the mechanism by which it depletes B cells in vivo has previously been unknown. In vitro, epratuzumab is cytotoxic to CD22-expressing human Burkitt lymphoma lines only when immobilized onto plastic plates or combined with a secondary antibody plus anti-IgM.

We used a Daudi lymphoma subclone selected for high expression of membrane IgM (mIgM) to investigate the cytotoxic mechanism of immobilized epratuzumab, and showed that it induced similar intracellular changes as observed upon crosslinking mIgM with anti-IgM. Specifically, we identified phosphorylation of CD22, CD79a and CD79b, and their translocation to lipid rafts, as essential for cell killing. Other findings include the co-localization of CD22 with mIgM, forming caps before internalization; induction of caspase-dependent apoptosis (25-60%); and a pronounced increase of pLyn, pERKs and pJNKs with a concurrent decrease of constitutively-active p38. The apoptosis was preventable by JNK or caspase inhibitors, and involved mitochondrial membrane depolarization, generation of reactive oxygen species, upregulation of pro-apoptotic Bax, and downregulation of anti-apoptotic Bcl-xl, Mcl-1 and Bcl-2. These findings indicated, for the first time, that epratuzumab and anti-IgM behave similarly in perturbing multiple BCR-mediated signals in malignant B cells.

Introduction

Epratuzumab (hLL2), a humanized anti-CD22 monoclonal antibody, is currently under clinical investigation for the treatment of non-Hodgkin lymphoma (NHL) and systemic lupus erythematosus (SLE). CD22, also referred to as sialic acid-binding Ig-like lectin-2 (Siglec-2) or B-lymphocyte adhesion molecule (BL-CAM), is a transmembrane type-I glycoprotein of 140 kDa, widely and differentially expressed on B cells (Kelm et al., 1994, Curr Biol 4:965-972; Law et al., 1995, J Immunol 155:3368-76; Wilson et al., 1991, J Exp Med 173:137-46). Structurally, the extracellular portion of CD22 comprises 7 Ig-like domains, of which the two N-terminal domains are involved in ligand binding, while the cytoplasmic tail contains 6 conserved tyrosine residues localized within the immunoreceptor tyrosine-based inhibition motifs (ITIM) and immunoreceptor tyrosine-based activation motifs (ITAM) (Wilson et al., 1991, J Exp Med 173:137-46; Schulte et al., 1992, Science 258:1001-4; Tones et al., 1992, J Immunol 149:2641-49). Functionally, CD22 recognizes α2,6-linked sialic acids on glycoproteins in both cis (on the same cell) and trans (on different cells) locations, and modulates B cells via interaction with CD79a and CD79b, the signaling components of the B-cell receptor (BCR) complex (Leprince et al., 1993, Proc Natl Acad Sci USA 90:3236-40; Peaker et al., 1993, Eur J Immunol 23:1358-63). Crosslinking BCR with cognate antigens or appropriate antibodies against membrane immunoglobulin (mIg) on the cell surface induces translocation of the aggregated BCR complex to lipid rafts, where CD79a, CD79b and CD22, among others, are phosphorylated by Lyn (Marshall et al., 2000, Immunol Rev 176:30-46; Niiro et al., 2002, Nat Rev Immunol 2:945-56; Smith et al., 1998, J Exp Med 187:807-11), which in turn triggers various downstream signaling pathways, culminating in proliferation, survival, or death (Peaker et al., 1993, Eur J Immunol 23:1358-63; Niiro et al., 2002, Nat Rev Immunol 2:945-56; Pierce & Liu, 2010, Nat Rev Immunol 10:767-77). Importantly, phosphorylated CD22, depending on environmental cues, can either positively or negatively affect BCR-mediated signaling pathways (Niiro et al., 2002, Nat Rev Immunol 2:945-56; Pierce & Liu, 2010, Nat Rev Immunol 10:767-77; Nitschke, 2005, Curr Opin Immunol 17:290-97; Otipoby et al., 2001, J Biol Chem 276:44315-22). Understanding the role of CD22 in B-cell malignancies, as well as B-cell-implicated autoimmune diseases, is of considerable interest.

As a single agent, epratuzumab is well-tolerated and depletes circulating B cells in patients with NHL, SLE, and Sjögren's syndrome by 35 to 50% (Goldenberg, 2006, Expert Rev Anticancer Ther 6:1341-53; Leonard & Goldenberg, 2007, Oncogene 26:3704-13; Leonard et al., 2003, J Clin Oncol 21:3051-59; Leonard et al., 2004, Clin Cancer Res 10:5327-34; Dorner et al., 2006, Arthritis Res Ther 8:R74). It has modest antibody-dependent cellular cytotoxicity (ADCC) but no complement-dependent cytotoxicity in vitro (Carnahan et al., 2007, Mol Immunol 44:1331-41). In vivo, it targets CD27⁻ naïve and transitional B cells, and decreases surface CD22 expression (Jacobi et al., 2008, Ann Rheum Dis 67:450-57). Epratuzumab downregulates the surface expression of certain adhesion molecules (CD62L and (β7 integrin), and increases the expression of β1 integrin on CD27⁻ B cells, resulting in migration of B cells towards the chemokine, CXCL12 (Daridon et al., 2010, Arthritis Res Ther 12:R204). Soluble epratuzumab does not have cytotoxic or cytostatic effects in vitro or in xenografts of human lymphoma in vivo (Carnahan et al., 2007, Mol Immunol 44:1331-41; Carnahan et al., 2003, Clin Cancer Res 9:3928 S-90S; Stein et al., 1993, Cancer Immunol Immunother 37:293-98). However, when immobilized to plastic plates or added in combination with suboptimal amounts of anti-IgM along with a crosslinking secondary antibody, it induces growth-inhibition in NHL cell lines, such as Ramos and Daudi (D1-1), a subclone of Daudi selected for a high expression of BCR (Qu et al., 2008, Blood 111:2211-19). We have reported previously that soluble epratuzumab phosphorylates and translocates CD22 to lipid rafts upon engagement (Qu et al., 2008, Blood 111:2211-19), but the exact mechanism by which epratuzumab kills normal and malignant B cells in patients, and inhibits the growth of lymphoma lines in vitro upon immobilization, remains elusive.

In this study, we evaluated key signaling pathways and molecules affected by immobilized epratuzumab. We showed in D1-1 cells that epratuzumab by either non-covalent adsorption on microtiter plates or conjugated covalently to polystyrene beads induces phosphorylation of CD22, CD79a and CD79b, and their translocation to lipid rafts, which are instrumental for cell death via caspase-dependent apoptosis. Additional experiments showed that immobilization of epratuzumab also induces substantial apoptosis (25 to 60%) in Ramos lymphomas. A pronounced phosphorylation of ERK and JNK MAP kinases, accompanied by a decrease in phosphorylated p38 MAP kinase, also was observed. Selective experiments interrogating intracellular events identified changes in mitochondrial membrane potential, generation of reactive oxygen species (ROS), involvement of caspases, and modulation of pro- and anti-apoptotic proteins, in the mechanisms of immobilized epratuzumab.

Materials and Methods

Cell lines, antibodies, and reagents—The Burkitt lymphoma cell lines, Daudi and Ramos, were obtained from ATCC (Manassas, Va.). D1-1, a subclone of Daudi selected for a higher expression of the BCR, was developed in-house (Qu et al. 2008, Blood 111:2211-19). Phospho-specific and other antibodies were obtained from CELL SIGNALING TECHNOLOGY® (Danvers, Mass.) and SANTA CRUZ BIOTECHNOLOGY® (Santa Cruz, Calif.). Anti-tyrosine antibody 4G10 was bought from Millipore (Billerica, Mass.), anti-IgM antibody, secondary goat anti-human Fc specific and rhodamine conjugated F(ab')$_2$ fragment goat anti-human IgG, F(ab')$_2$ fragment specific were obtained from Jackson ImmunoResearch (West Grove, Pa.). Cell culture media, supplements, annexin V ALEXA FLUOR® 488 conjugate, TMRE, and CM-H$_2$DCF-DA were supplied by INVITROGEN™ (Grand Island, N.Y.). One Solution Cell Proliferation assay reagent was obtained from Promega (Madison, Wis.). PHOSPHOSAFE™ and RIPA buffers were procured from EMD chemicals (Billerica, Mass.). For epratuzumab immobilization, non-tissue-culture flat-bottom polystyrene plates were obtained from BD Biosciences (San Jose, Calif.), and CP-30-10 carboxyl-coated polystyrene beads were bought from Spherotech (Lake Forest, Ill.). All other chemicals were obtained from SIGMA-ALDRICH® (St. Louis, Mo.).

Immobilization of epratuzumab—Epratuzumab (10 g/mL or as indicated) in carbonate/bicarbonate buffer (50 mM; pH 9.6) was immobilized on non-tissue-culture flat-bottom plates by incubating the plate at 4° C. overnight. Next day, plates were washed 2× with RPMI-1640 medium. Besides immobilizing epratuzumab onto plates, 100 μg was also immobilized to Protein A beads (100 μL). Supernatants were analyzed for the amounts of epratuzumab bound to the beads. Epratuzumab-bound beads were washed 3× with PBS and reconstituted in 100 μL of the RPMI-1640 medium. For flow cytometry, epratuzumab also was conjugated to CP-30-10 carboxyl-coated polystyrene beads using the manufacturer's protocol. Briefly, 50 μg of epratuzumab was conjugated to 200 μL of polystyrene beads in 1 mL of MES buffer containing 20 mg of EDC for 30 min. Beads were washed 3× with PBS and reconstituted in 0.05M MES buffer containing 0.05% BSA.

Cell culture and cytotoxicity assay—Cell lines were cultured in RPMI-1640 medium supplemented with 10% heat-inactivated fetal bovine serum (FBS), 2 mM L-glutamine, 200 U/mL penicillin, and 100 g/mL streptomycin in a humidified incubator at 37° C. with 5% CO$_2$. To evaluate the functional activity of epratuzumab or epratuzumab F(ab')$_2$, different amounts (5, 10 and 20 g/mL) were immobilized in 48-well plates. Plates were washed and D1-1 or Ramos cells were seeded (1×10$^4$ cells per well) and incubated for 4 days. The number of viable cells was then determined using the MTS assay per the manufacturer's protocol, plotted as percent of the untreated. Activity of soluble epratuzumab or epratuzumab F(ab')$_2$ was also evaluated.

Annexin V binding assay—Cells in 6-well plates (2×10$^5$ cells per well) were either treated with epratuzumab immobilized to polystyrene beads or immobilized to plates for 24 or 48 h, washed, resuspended in 100 1 of annexin-binding buffer, and stained with 5 1 of Annexin V-ALEXA FLUOR® 488 conjugate for 20 min. Cells were then stained with 1 g/mL propidium iodide (PI) in 400 1 of annexin-binding buffer, and analyzed by flow cytometry (FACSCALIBUR™). When required, cells were pretreated with the indicated inhibitors for 2 h before adding the test article.

Immunoblot analysis—D1-1 and Ramos cells (2×10$^7$ cells) were added to plates immobilized with epratuzumab (10 g/mL) for varying time points as indicated. Cells were washed with PBS, lysed in ice-cold PHOSPHOSAFE™ buffer, and the lysates clarified by centrifugation at 13,000×g. Protein samples (25 g/lane) were resolved by SDS-PAGE on 4-20% gradient tris-glycine gels followed by transfer onto nitrocellulose membranes.

Isolation of lipid rafts—D1-1 cells (3×10$^7$) were treated with the indicated antibodies or added to plates coated with epratuzumab (10 g/mL) for 2 h. After treatment, cells were lysed in 2 mL of buffer containing CHAPS/low-salt (20 mM NaCl and 40% sucrose), and lysates were fractionated in a sucrose gradient and lipid rafts were prepared as described earlier (Qu et al., 2008, Blood 111:2211-19).

Co-immunoprecipitation analysis—Six-well plates were coated with the required antibodies (10 g/mL) in carbonate/bicarbonate buffer for 24 h. Plates were washed with RPMI-1640 medium containing 5% FBS, and D1-1 cells were added to the wells (5×10$^6$ cell/well) for 2 h. Following incubation, cells were lysed in ice-cold RIPA buffer, and co-immunuprecipitation was performed using phospho-tyrosine antibody (4G10; 1:200 dilution), as described earlier (Gupta et al., 2006, Cancer Res 66:8182-91). 20 1 of the samples were separated by SDS-PAGE and transferred onto a nitro-cellulose membrane, followed by probing with the indicated antibodies.

Mitochondrial membrane potential ($\Delta\psi_m$) and reactive oxygen species (ROS) assays—D1-1 cells (2×10$^5$ cells per well) were added to the 6-well plates coated with epratuzumab (10 g/mL) for 48 h. Cells were washed and stained for 30 min in the dark at 37° C., either with TMRE (50 nM) for $\Delta\psi_m$ analysis or CM-H$_2$DCF-DA (1 M) for ROS analysis. Samples were washed 3× with PBS and analyzed for changes in fluorescence using flow cytometry.

Immunofluorescence analysis—To analyze the co-localization of CD22 and IgM receptors, D1-1 cells were treated with epratuzumab (7.5 g/mL) or anti-IgM conjugated to ALEXA FLUOR® 488 (1 g/mL) alone and in combination with a secondary crosslinking goat anti-human antibody for 5 min at 37° C. Cells were washed with PBS to remove the antibodies and incubated at room temperature for 30 min, followed by fixation with 4% paraformaldehyde, and staining with rhodamine-conjugated Fc-specific goat anti-human IgG for 20 min. Cells were washed with PBS and visualized by fluorescence microscopy. To evaluate the translocation of CD22 in lipid rafts, D1-1 cells were incubated with Protein A-immobilized epratuzumab for 4 h, fixed, and permeabilized with 0.1% Triton X-100 in PBS. CD22 and IgM receptors were evaluated by epratuzumab-dylight 550 and anti-IgM-ALEXA FLUOR® 488, respectively. Images were overlaid using Photoshop software.

Cell cycle analysis—Cells were seeded in 6-well plates (2×10$^5$ cells per well) and treated with epratuzumab conjugated to polystyrene beads or the indicated antibodies for 72 h. Following incubation, cell cycle analysis was performed by flow cytometry as described (Gupta et al., 2010, Blood 116: 3258-67).

Results

Figure 31:
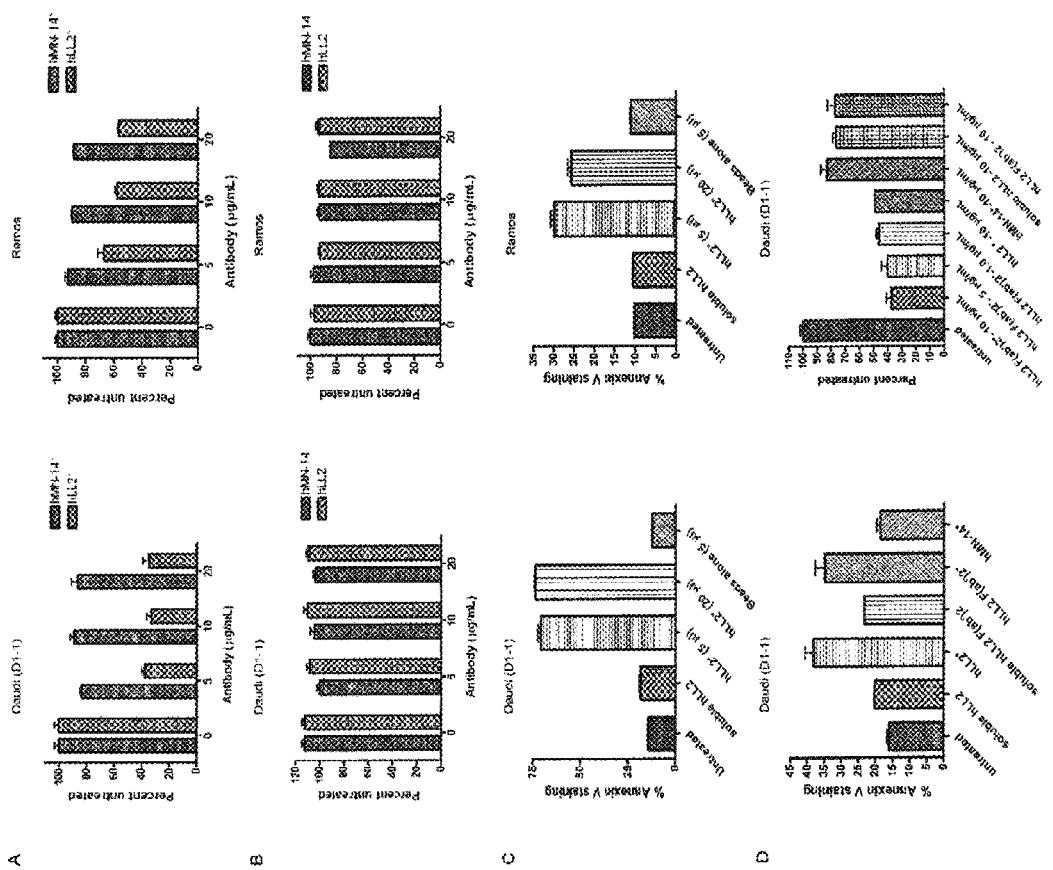
FIG. 31. Epratuzumab (hLL2) immobilized on plastics (hLL2*) displays cytotoxicity against Daudi (D1-1) and Ramos cells. (A) Cells ($1 \times 10^4$ cells per well in 48-well plate) were added to the plates coated with varying amounts of hLL2* for 4 days and viability was determined using the MTS reagent. (B) Effect of similar concentrations of soluble epratuzumab on the growth of cells. (C) D1-1 and Ramos cells ($2 \times 10^5$ cells per well in 6-well plate) were treated with 5 and 20 µl of hLL2* on polystyrene beads for 24 and 48 h respectively followed by Annexin staining analysis. (D) D1-1 cells were added to the plates coated with F(ab')2 fragments of hLL2 (10 µg/mL) and apoptosis was determined 24 h later (left panel). Growth inhibition by varying concentrations of immobilized F(ab')2 fragments of hLL2 was evaluated in the MTS assay (right panel). Nonspecific isotype-matched control antibody, hMN-14, was evaluated in solution as well as immobilized to determine specificity of hLL2*. Error bars represent standard deviation (SD), where n=3.

Immobilization of epratuzumab induces growth-inhibition and apoptosis—The ability to induce growth-inhibition was evaluated by immobilizing epratuzumab to non-tissue-culture coated flat-bottom plates. Varying amounts of epratuzumab were immobilized. In the cell viability assay, 5 g/mL of immobilized epratuzumab induced significant growth-inhibition in D1-1 cells (FIG. 31A). About 60% growth-inhibition was observed at this concentration, and little change was found at higher concentrations of 10 and 20 g/mL, indicating saturation (FIG. 31A). Similar growth-inhibition of the Burkitt lymphoma line, Ramos, was observed, although it was slightly less than with D1-1. In Ramos cells, 10 g/mL epratuzumab induced about 45% growth-inhibition (FIG. 31A). This difference in sensitivity could be due to the levels of CD22 and overexpression of BCR components in D1-1. Immobilized nonspecific hMN-14 antibody did not induce growth-inhibition in either cell line (FIG. 31A). Soluble epratuzumab in the media, even at the highest concentration (20 g/mL), did not induce growth-inhibition in either cell line, indicating the requirement of immobilization (FIG. 31B).

We next evaluated the role of apoptosis in the effect of epratuzumab. Carboxyl-coated polystyrene beads were used to immobilize epratuzumab. As shown in FIG. 31C, 5 and 20 L of epratuzumab-coated beads induced apoptosis in both D1-1 and Ramos at 24 h. In D1-1, 5 L of epratuzumab-coated beads induced about 75% apoptosis, while similar amounts of uncoated beads displayed annexin V staining, comparable to untreated cells (FIG. 31C). Significant apoptosis was also observed in Ramos cells by epratuzumab-coated beads (FIG. 31C). Likewise, Protein A-immobilized epratuzumab induced apoptosis and growth-inhibition in both D1-1 and Ramos cells (data not shown). These results demonstrate the requirement of epratuzumab immobilization onto plastic or to beads for inducing growth-inhibition and apoptosis in the target malignant cells. Similar to epratuzumab, the immobilized F(ab')$_2$ fragments of epratuzumab also induced apoptosis and growth inhibition in D1-1 cells (FIG. 31D). These results negate the role of Fc effector functions and confirm the role of signaling events in the target cells for observed growth inhibition though immobilization.

Figure 32A:
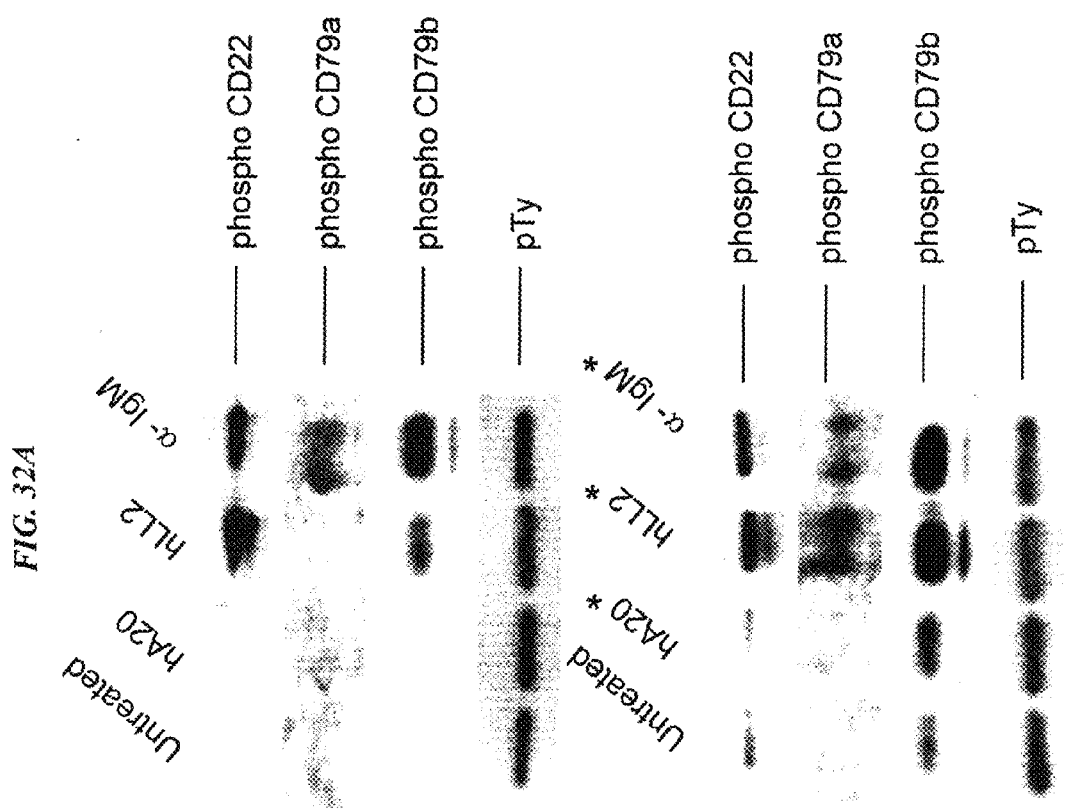
FIG. 32. Immobilized epratuzumab (hLL2*) induces phosphorylation of CD79a and CD79b and their translocation into lipid rafts along with CD22. (A) D1-1 ($3\times10^7$) cells were added to plates coated with hLL2* for 2 h. Co-immunoprecipitation (Co-IP) experiments were performed using p-Tyr antibody 4G10. Phosporylation was determined probing the membranes with CD22, CD79a or CD79b antibodies. (B) Phosphorylation profile of CD22, CD79a and CD79b with soluble epratuzumab (7.5 µg/mL) along with suboptimal amounts of anti-IgM (1 µg/mL) and a crosslinking secondary antibody (10 µg/mL). (C) Cells as described earlier were treated with hLL2* and cells lysates were fractionated by sucrose density gradient ultracentrifugation. The lipid rafts were collected from the interface of 5% to 30% sucrose. Distribution of CD22, CD79a and CD79b in the lipid rafts was analyzed by Western blotting using specific antibodies. (D) Immunofluorescence analysis of CD22 and IgM receptors by soluble hLL2 with or without anti-IgM. The receptors colocalize in the caps when hLL2 and anti-IgM are added together. (E) Immunofluorescence analysis of CD22 and IgM receptors by hLL2 immobilized to protein A beads.
Figure 32B:
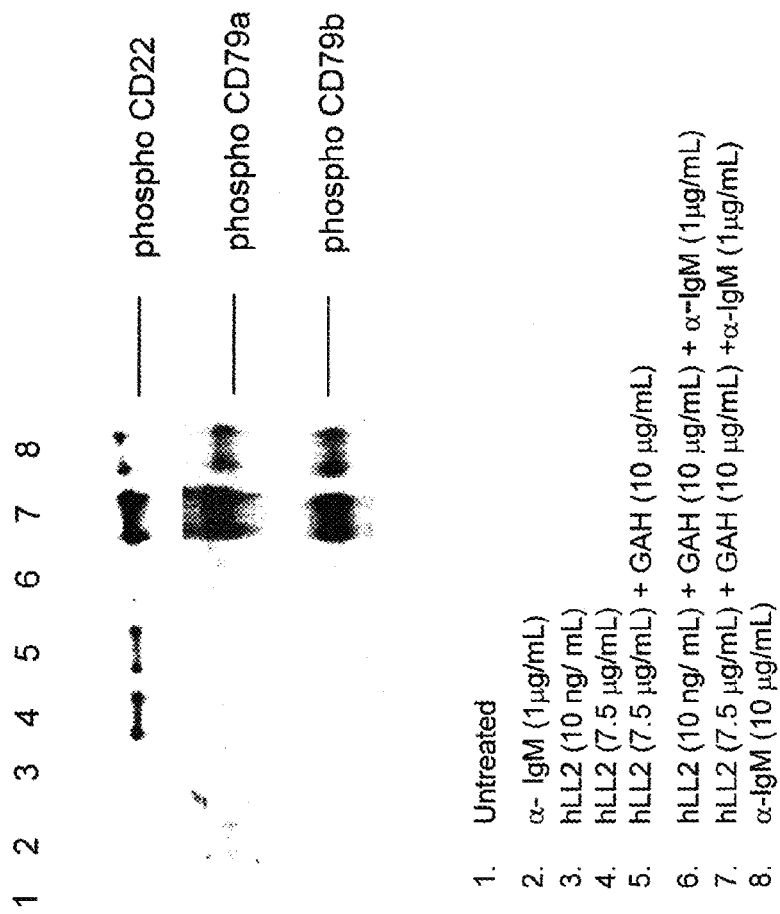

Immobilized epratuzumab induces phosphorylation of CD22, CD79a and CD79b- To understand the mechanism by which immobilized epratuzumab inhibits growth in these lymphoma lines, we evaluated the phosphorylation profiles of the BCR components, CD79a and CD79b. CD79a and CD79b form hetrodimers and are noncovalently-bound membrane immunoglobulins that regulate BCR-mediated signaling by ITAM motifs in their cytoplasmic tails. Cells were subjected to immobilized epratuzumab and other antibodies for 2 h, and co-immunoprecipitation experiments were performed using the phospho-tyrosine antibody, 4G10. As shown in FIG. 32A (top panel), anti-IgM (10 g/mL) antibody induced phosphorylation of CD22, CD79a and CD79b molecules, while soluble epratuzumab induced phosphorylation of CD22, but not CD79a and CD79b. Immobilization of anti-IgM and epratuzumab induced phosphorylation of CD22 as well as CD79a and CD79b (FIG. 32A; bottom panel). Ligation of CD22 on D1-1 by immobilized epratuzumab was similar to ligation of BCR by anti-IgM (above a threshold concentration, i.e., 10 g/mL), in that both resulted in the phosphorylation of CD22, CD79a and CD79b. Similar phosphorylation of CD22, CD79a and CD79b was observed with soluble epratuzumab combined with suboptimal amounts of anti-IgM (1 g/mL) and a secondary crosslinking goat anti-human IgG, while anti-IgM (1 g/mL) alone did not induce phosphorylation of any of these molecules (FIG. 32B). Soluble epratuzumab in combination with anti-IgM and a secondary crosslinking antibody has been observed previously to induce growth-inhibition in lymphoma lines. These results with respect to differences in the phosphorylation profiles of CD79a and CD79b by soluble and immobilized epratuzumab clearly implicate components of BCR in the growth-inhibition due to immobilized epratuzumab or the combination of epratuzumab and anti-IgM antibody.

Figure 32C:
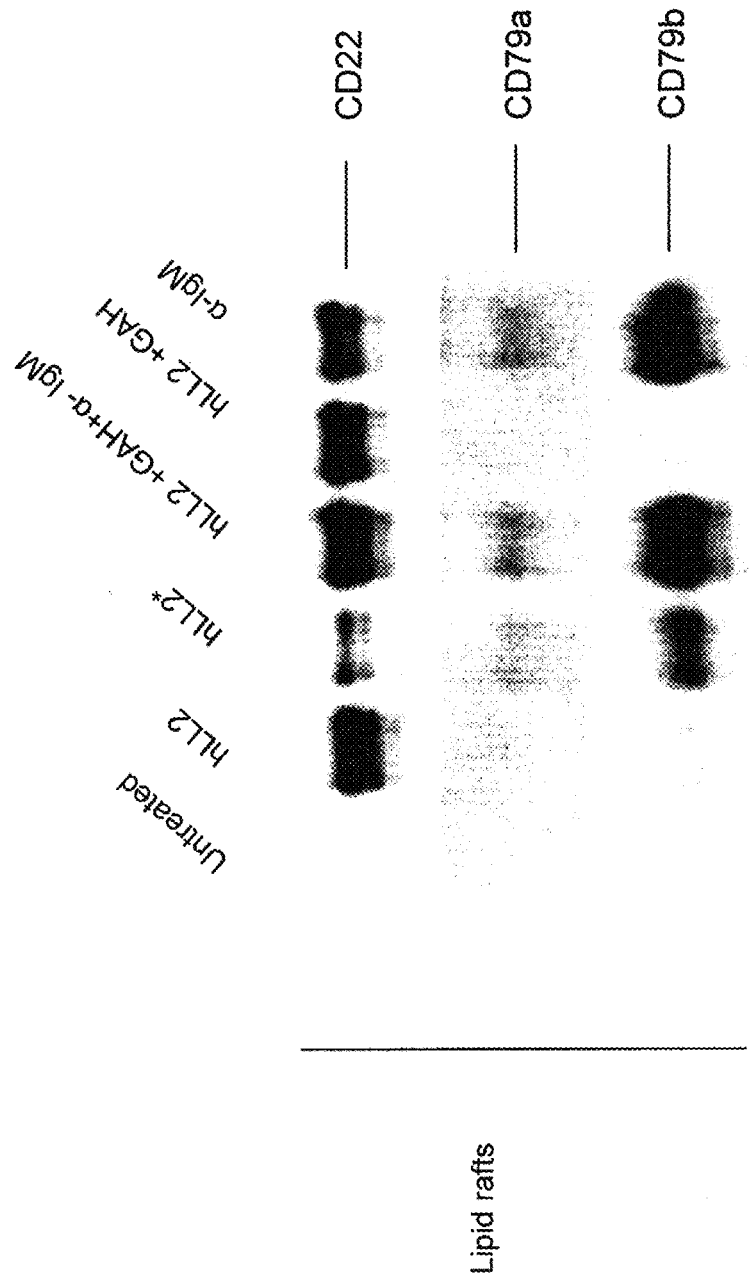

Immobilized epratuzumab translocates CD22 and CD79 to lipid rafts—The observation that immobilized epratuzumab induces phosphorylation of BCR components, CD79a and CD79b, prompted us to investigate the membrane distribution of CD22, CD79a and CD79b in lipid rafts, using sucrose density gradient ultracentrifugation. Anti-IgM (10 g/mL) treatment resulted in the distribution of CD22, CD79a and Cd79b into lipid rafts (FIG. 32C). Soluble epratuzumab, which is known to induce phosphorylation of CD22 and migration of CD22 into lipid rafts (Qu et al., 2008, Blood 111:2211-19), did not induce redistribution of CD79a and CD79b into lipid rafts (FIG. 32C). However, soluble epratuzumab together with suboptimal amounts of anti-IgM (1 g/mL) and a secondary crosslinker resulted in the migration of CD22, CD79a and CD79b into lipid rafts. Since soluble epratuzumab together with anti-IgM (1 g/mL) and a crosslinker induced growth-inhibition in these malignant cells, the presence of phosphorylated CD22, CD79a and CD79b in lipid rafts seems to be critical for the effects of epratuzumab. Immobilized epratuzumab also induced migration of these components into lipid rafts, although the signals were not as strong as they were for other samples; this could be due to loss of some treated cells because of adherence to the epratuzumab-coated plates (FIG. 32C).

Figure 32D:
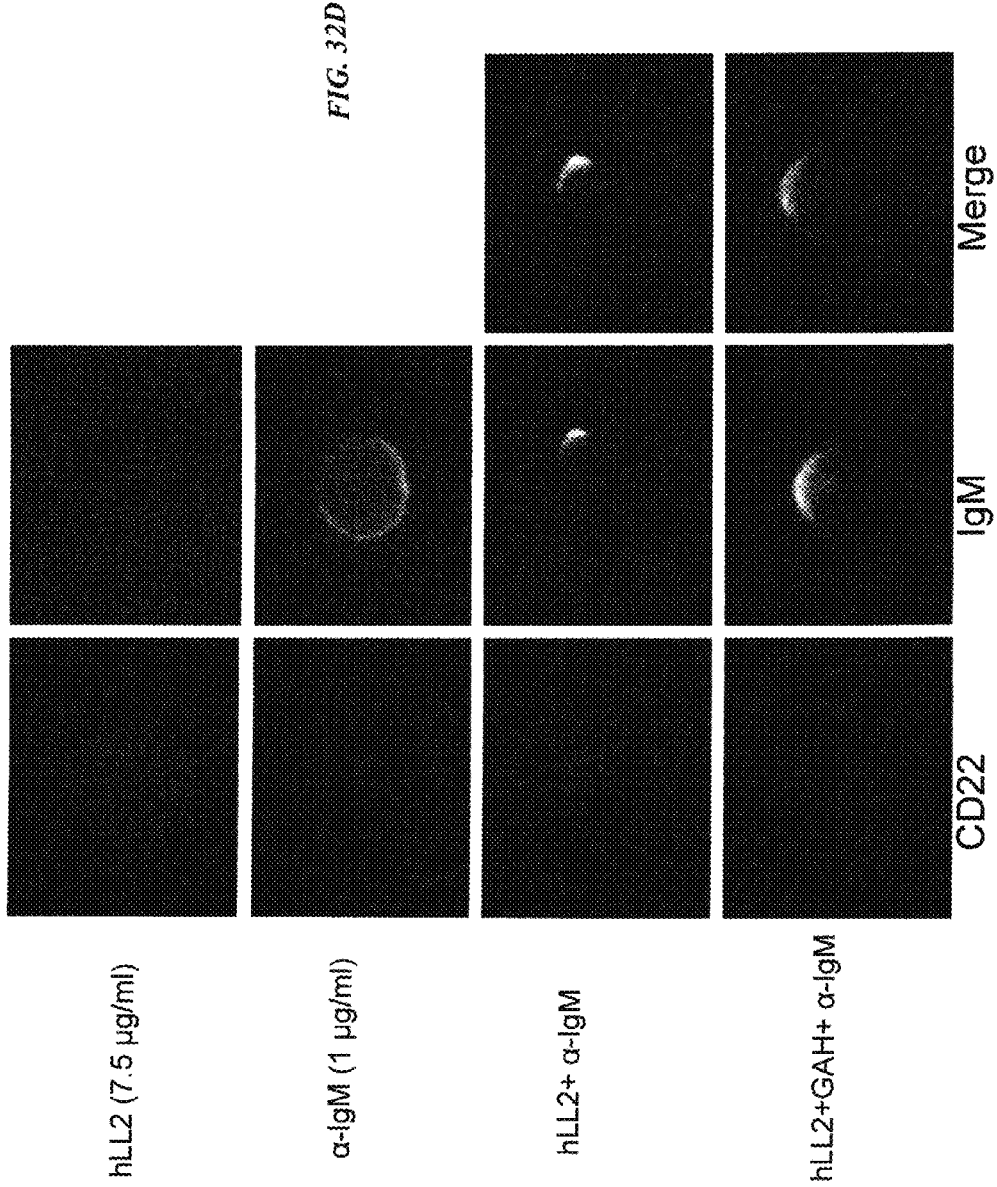
Figure 32E:
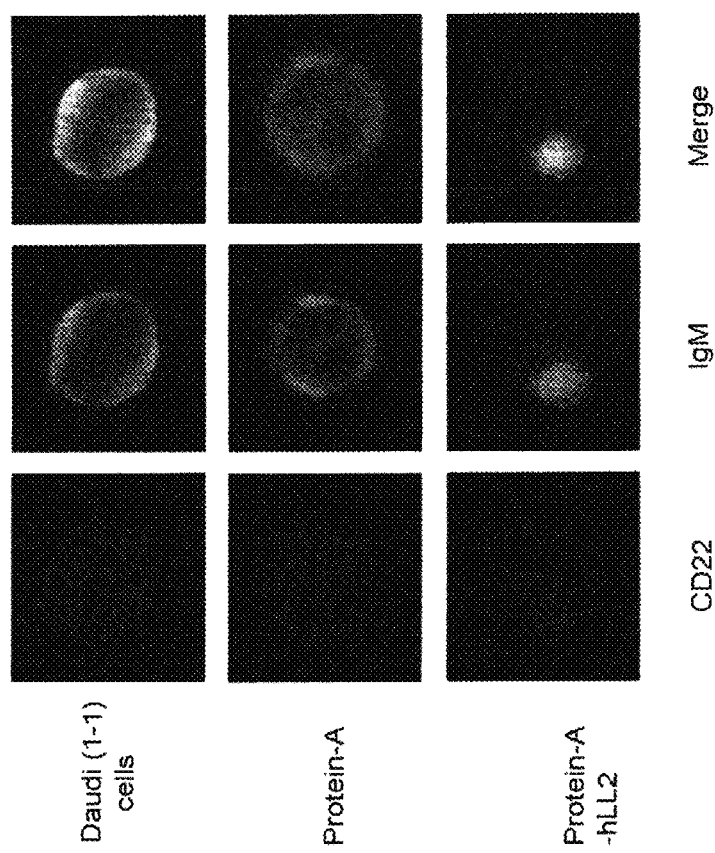
Figure 33:
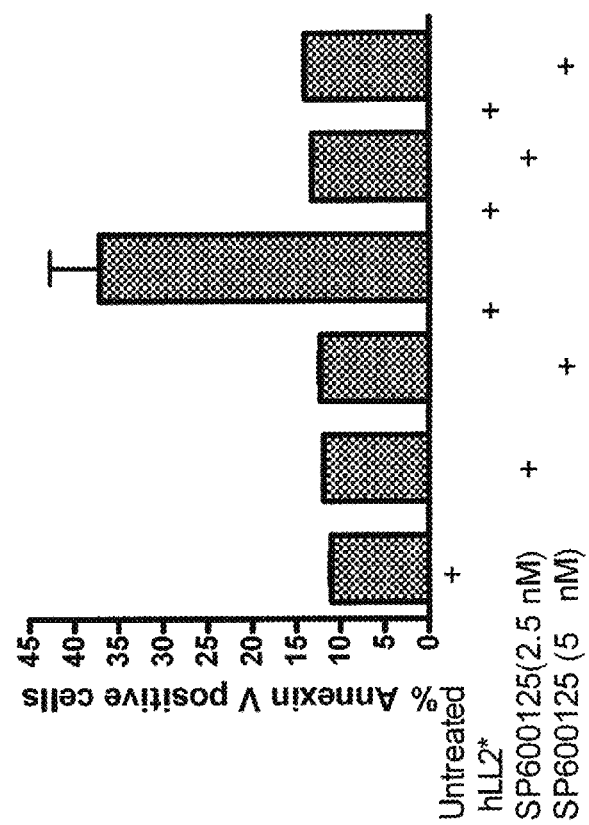
FIG. 33. Inhibition of JNK pathway inhibits hLL2* induced apoptosis. SP600125, a chemical inhibitor for stress activated JNK MAP kinase, inhibits the apoptosis in D1-1 cells induced by hLL2*. Cells were pretreated with inhibitor SP600125 (2.5 or 5 nM) for 2 h followed by addition of cells in media containing the inhibitor to wells coated with hLL2* (10 µg/mL), and apoptosis was determined by annexin V staining 24 h later. Error bars represent SD, where n=3.
Figure 34:
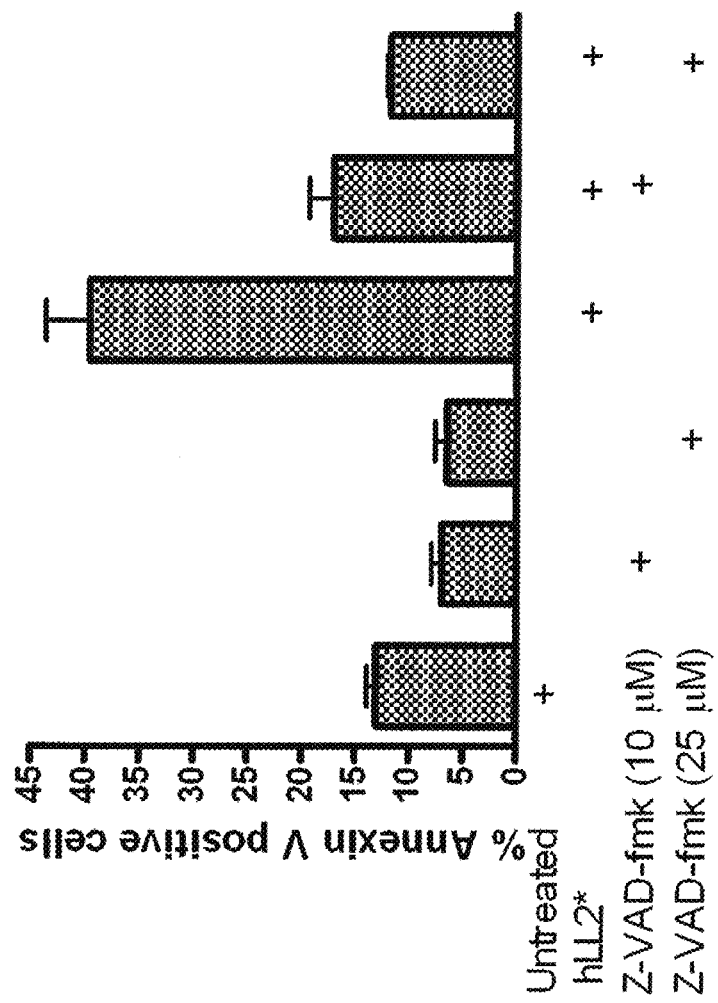
FIG. 34. Immobilized epratuzumab (hLL2*) induces caspase-dependent apoptosis. Caspase inhibitor z-vad-fmk inhibits apoptosis in D1-1 cells induced by hLL2*. Cells were pretreated with z-vad-fmk pan-caspase inhibitor (10 or 25 µM) for 2 h, followed by addition of cells in media containing the inhibitor to wells coated with hLL2* (10 µg/mL), and apoptosis was determined by annexin V staining 24 h later. Error bars represent SD, where n=3.

We also examined the distribution of CD22 and BCR components by immunofluorescence. Soluble epratuzumab binds to CD22 and internalizes rapidly into the cells (Carnahan et al., 2003, Clin Cancer Res 9:3982 S-90S). To study the distribution of CD22 and IgM receptors, we treated the cells with different antibodies alone or in combination for 5 min at 37° C. Cells were fixed after 30 min. Immunofluorescence analysis revealed the binding of soluble epratuzumab and anti-IgM to cell-surface CD22 and IgM receptors, respectively, when the two antibodies were evaluated separately (FIG. 32D). However, when soluble epratuzumab combined with suboptimal amounts of anti-IgM (1 g/mL) were added, they formed caps and co-localized in about 70% of cells (FIG. 32D). Similar co-localization of CD22 and IgM receptors was observed when cells were treated with Protein A-bound epratuzumab (FIG. 32E). These observations indicate the co-localization and requirement of both IgM and CD22 receptors, either when soluble epratuzumab is used together with suboptimal amounts of anti-IgM or when epratuzumab is immobilized.

Requirement of Lyn for growth-inhibition by immobilized epratuzumab—Lyn plays a critical role in regulating BCR activity by phosphorylating tyrosine residues in the ITAM domain of CD79a, CD79b, and ITIM domain in CD22, followed by recruitment of SHP-1 to CD22 (Schulte et al., 1992, Science 258:1001-4; Nitschke, 2005, Curr Opin Immunol 17:290-97; Chaouchi et al., 1995, J Immunol 154:3096-104; Doody et al., 1995, Science 269:242-44; Nitschke 2009, Immunol Rev 230:128-43). To understand this growth-inhibition, we evaluated the phosphorylation profiles of Lyn as a function of time. D1-1 cells were added to epratuzumab-coated plates for different times up to 4 h. Cells were lysed in RIPA buffer and phospho-tryosine residues were immunoprecipitated using monoclonal antibody 4G10. Immobilized epratuzumab induced rapid phosphorylation of tyrosine residues that continued for 4 h (not shown). Probing the same membranes with different antibodies depicted rapid and sustained phosphorylation of Lyn and Syk molecules (not shown). In a separate experiment, we repeated these studies until 24 h, and observed that immobilized epratuzumab induces the phosphorylation of Lyn and PLCγ2 (not shown). Although we observed phosphorylation of Syk by co-immunoprecipitation, we did not observe a similar time-dependent phosphorylation of Syk by using anti-phospho Syk antibodies (not shown).

To further elucidate the role of Lyn in this growth-inhibition by immobilized epratuzumab, we evaluated the binding of SHP-1 to the tyrosine residues. Cells were treated with various antibody combinations and a co-immunoprecipitation experiment was performed using antibody 4G10. Membranes were probed with SHP-1 antibody and the results indicate binding of SHP-1 to tyrosine residues in the samples treated with immobilized epratuzumab (not shown). Similar binding of SHP-1 was observed in samples treated with epratuzumab and suboptimal amounts of anti-IgM in presence of a secondary crosslinking antibody (not shown). In contrast, no significant binding was observed in samples treated with soluble epratuzumab or suboptimal amounts of anti-IgM alone (not shown). These results establish the requirement of phosphorylation of Lyn and recruitment of SHP-1 to CD22 to negatively regulate BCR signaling resulting in growth-inhibition.

Modulation of MAP kinases—Mitogen-activated protein (MAP) kinases are a group of serine threonine protein kinases that respond to a variety of environmental cues, such as growth factors, cellular stress (e.g., UV, osmotic shock, DNA damage) and others, by either inducing survival and cell growth, or apoptosis. Previously, we observed that the anti-HLA-DR mAb, IMMU-114, induced growth-inhibition by hyperactivation of the ERK and JNK group of MAP kinases, while p38 was not affected (Stein et al., 2010, Blood 115: 5180-90). To further elucidate the mechanism of growth-inhibition by immobilized epratuzumab, we studied the effects on all three MAP kinases. Immobilized epratuzumab induced modest activation and phosphorylation of the ERK and JNK group of MAP kinases (not shown). This activation was rapid, and could be detected within 30 min and sustained over a period of 24 h. In contrast, p38, the third group of MAP kinases, was inhibited and the phoshorylation of p38 was downregulated by immobilized epratuzumab within 30 min of treatment of the target cells (not shown).

We further studied the role of stress in the growth-inhibition by immobilized epratuzumab in the presence of an inhibitor of stress-activated JNK MAP kinase, SP600125. Two doses (2.5 and 5 nM) of the inhibitor were evaluated and at both doses, apoptosis was inhibited significantly in D1-1 cells (FIG. 3). Thus, this differential activation/inhibition of MAP kinases attests to the fact that immobilized epratuzumab affects target cells by invoking multiple signaling pathways.

Immobilized epratuzumab induces production of ROS and changes in mitochondrial membrane potential—Induction of stress in cells results in the generation of free oxygen radicals in mitochondria. ROS are chemically-reactive oxygen molecules that induce mitochondrial membrane depolarization, activating pro-apoptotic proteins such as Bax, and resulting in programmed cell death in the target cells. To further investigate the role of stress in this growth-inhibition by immobilized epratuzumab, we studied the generation of ROS and changes in mitochondrial membrane potential in the affected cells. Treatment with immobilized epratuzumab resulted in about 24% cells having enhanced ROS production compared to about 10% in D1-1 cells treated with soluble epratuzumab or untreated (not shown).

Immobilized epratuzumab induced mitochondrial membrane depolarization in about 45% of D1-1 cells, compared to about 20% of cells treated with immobilized nonspecific hMN-14 antibody or untreated (not shown). Similar results for ROS and changes in mitochondrial membrane potential were observed in Ramos (data not shown).

Immobilized epratuzumab induces caspase-mediated apoptosis—We next evaluated the effect of immobilized epratuzumab on pro-/anti-apoptotic proteins and caspases in D1-1 and Ramos cells subjected to immobilized epratuzumab for 24, 48 and 72 h. Cell lysates were evaluated for the expression profiles of anti-apoptotic proteins, Bcl-2, Bcl-xL and Mcl-1, and pro-apoptotic protein, Bax. In both cell lines, immobilized epratuzumab downregulated anti-apoptotic proteins, Bcl-xL and Mcl-1, and increased the expression levels of pro-apotoic, Bax (not shown). Bcl-2 was downregulated in D1-1, and very low levels were detected in Ramos. The observed apoptosis by immobilized epratuzumab in both D1-1 and Ramos was caspase-dependent, as observed by the cleavage of caspase 3, caspase 9 and PARP molecules, which are known to induce apoptosis in the target cells (not shown). The observed apoptosis was abrogated by the pan-caspase inhibitor, z-vad-fmk (10 μM) in D1-1, confirming the requirement of caspases in the apoptosis induced by immobilized epratuzumab (FIG. 4).

Deregulation of the cell cycle—Immobilized epratuzumab was observed to arrest D1-1 cells in G1 phase of the cell cycle (not shown), while soluble epratuzumab had no effect. Epratuzumab conjugated to beads resulted in about 10% more cells in the G1 phase. A similar increase in the levels of cells was observed in samples treated with anti-IgM or epratuzumab combined with suboptimal amounts of anti-IgM. This deregulation of the cell cycle was associated with changes in the levels of CDK inhibitors, such as p21, p27, and p57 and expression levels of cyclin D1, Rb and phosphorylation of Rb (not shown).

Calcium release assay—We did not observe any release of calcium by immobilized epratuzumab. Also, we did not find an inhibitory effect of epratuzumab or immobilized epratuzumab on the anti-IgM-mediated release of calcium, even after preincubating the cells for 18 h (not shown).

Discussion

In the present study, we confirmed that ligation of mIgM by a sufficient amount of anti-IgM (10 μg/mL) induces the phosphorylation of CD22, CD79a and CD79b, and the localization of all three phosphorylated proteins in the lipid rafts, leading to cell death in the Burkitt D1-1 line. We further show that ligation of CD22 with immobilized epratuzumab induces a similar change in CD22, CD79a and CD79b, including phosphorylation, translocation into lipid rafts, and subsequent cell death. Thus, it appears that for a CD22-binding agent to kill Daudi cells in particular, and perhaps other CD22-expressing B-cell lymphomas, two critical events must occur in concert, (i) phosphorylation of CD22, CD79a and CD79b above a threshold level, and (ii) their movement to lipid rafts. This notion is supported by the finding that little or no cell death was observed for D1-1 with either soluble epratuzumab at 50 nM plus a secondary crosslinking antibody or with a suboptimal amount of anti-IgM (1 μg/mL). The former treatment efficiently induced phosphorylation of CD22 and the localization of phospho-CD22 into lipid rafts, but was unable to translocate the weakly phosphorylated CD79a and CD79b to lipid rafts, whereas the latter treatment failed to phosphorylate CD22, CD79a and CD79b at all. On the other hand, combining these two treatments could effect both phosphorylation of CD22, CD79a and CD79b, along with their localization into lipid rafts, and consequently, cell death, as observed for anti-IgM at 10 μg/mL or immobilized epratuzumab.

Binding of CD22 to beads coated with B3 antibody for human CD22 was reported to lower the threshold concentration of anti-IgM required for stimulating DNA synthesis in tonsillar B cells by two orders of magnitude, presumably due to sequestration of CD22 from mIgM by restricting the lateral movement of CD22 in the plane of the cell membrane (Doody et al., 1995, Science 269:242-44). Our immunofluorescence results obtained with D1-1 cells, however, show otherwise, as demonstrated by the colocalization of mIgM and CD22 into a cap-like structure with both soluble epratuzumab and anti-IgM added, and an even more massive coaggregation with epratuzumab immobilized on beads. Thus, we believe that the ability of immobilized epratuzumab to promote such a high degree of mIgM crosslinking without the need for anti-IgM constitutes a sufficient condition for cell killing and negates the inhibitory effect of phosphorylated CD22 in close proximity.

Knowing that binding of CD22 by soluble epratuzumab leads to prompt internalization, and engagement of CD22 with epratuzumab immobilized on plastics should not, raises the question whether internalization of CD22 plays a role in the mechanism of cell killing. Also, the intracellular fate of CD22 after internalization needs to be addressed with experiments designed to determine the kinetics of CD22 recycling, which may reveal that internalized CD22 is predominantly degraded, rather than recycled.

Taking a cue from CD20, which also interacts with BCR and affects calcium mobilization (Walshe et al., 2008, J Biol Chem 283:16971-84) and its own degradation Kheirallah et al., 2010, Blood 115:985-94), the expression levels of CD22 as well as BCR on the cell surface may be critical for the activity of anti-CD22 mAbs, in particular for a non-blocking anti-CD22 mAb like epratuzumab.

Intriguingly, we neither observed any transient increase in intracellular calcium by immobilized epratuzumab nor any inhibitory effect of immobilized epratuzumab on calcium release after stimulation with anti-IgM (not shown). Experiments with longer incubation (16 h) of immobilized epratuzumab followed by stimulation with anti-IgM also did not have any effect on resulting calcium release (not shown). These results were corroborated by a recent finding that a multivalent sialylated polymer synthesized to bind only CD22, but not mIgM, failed to induce any calcium flux (Courtney et al., 2009, Proc Natl Acad Sci USA 106:2500-5), and highlight a key dissimilarity between the mechanism of anti-IgM and immobilized epratuzumab is calcium mobilization, which may require direct engagement of mIgM with anti-IgM. However, resemblances of anti-IgM and immobilized epratuzumab in their characteristic mechanism of action abound, as demonstrated by a similar profile of signal alterations in ERKs, JNKs and p38 MAPK, caspase-dependent apoptosis, change in mitochondria membrane potential, and the generation of ROS.

In conclusion, we provide evidence for the mechanism of action by which immobilized epratuzumab induces cytotoxic and cytostatic effects in CD22-expressing B lymphoma lines (D1-1 and Ramos), both of which have BCR of the IgM isotype. These findings indicate, for the first time, that immobilized epratuzumab and anti-IgM behave similarly in perturbing the BCR-mediated signals in malignant B cells.

\* \* \*

All patents and other references cited in the specification are indicative of the level of skill of those skilled in the art to which the invention pertains, and are incorporated herein by reference, including any Tables and Figures, to the same extent as if each reference had been incorporated by reference individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the invention.

SEQUENCE LISTING

```
<160> NUMBER OF SEQ ID NOS: 125

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55
```

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

```
Cys Gly Phe Glu Glu Leu Ala Trp Lys Ile Ala Lys Met Ile Trp Ser
1               5                   10                  15

Asp Val Phe Gln Gln Gly Cys
            20
```

<210> SEQ ID NO 8
<211> LENGTH: 51
<212> TYPE: PRT
<213> ORGANISM: Homo sapiens

<400> SEQUENCE: 8

```
Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50
```

<210> SEQ ID NO 9
<211> LENGTH: 54
<212> TYPE: PRT
<213> ORGANISM: Homo sapiens

<400> SEQUENCE: 9

```
Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50
```

<210> SEQ ID NO 10
<211> LENGTH: 44
<212> TYPE: PRT
<213> ORGANISM: Homo sapiens

<400> SEQUENCE: 10

-continued

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Ser His Ile Gln Ile Pro Pro Gly Leu Thr Glu Leu Gln Gly Tyr
1               5                   10                  15

Thr Val Asp Val Leu Arg Gln Gln Pro Pro Asp Leu Val Phe Ala
            20                  25                  30

Val Glu Tyr Phe Thr Arg Leu Arg Glu Ala Arg Ala
        35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Gln Gly Tyr
1               5                   10                  15

Thr Val Glu Val Leu Lys Gln Gln Pro Pro Asp Leu Val Phe Ala
            20                  25                  30

Val Glu Tyr Phe Thr Arg Leu Arg Glu Ala Arg Ala
        35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ile Glu Tyr Leu Ala Lys Gln Ile Val Asp Asn Ala Ile Gln Gln
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala
```

```
<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
1               5                   10                  15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15
```

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ile Glu Tyr Leu Ala Lys Asn Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Leu Ala Lys Gln Ile Val Asp Asn Ala Ile Gln Gln
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

-continued

```
Gln Ile Glu Tyr Leu Ala Lys Gln Ile Val Asp Asn Ala Ile Gln Gln
1               5                   10                  15
Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15
Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15
Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr His Ala Lys Gln Ile Val Asp His Ala Ile His Gln
1               5                   10                  15
Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15
Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
            20

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25
```

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
```

```
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 87

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
```

```
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 88

Xaa Xaa Xaa Xaa Xaa Ala Xaa Xaa Ile Val Xaa Xaa Ala Ile Xaa Xaa
1               5                   10                  15

Xaa

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
```

```
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: DOTA-Phe
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES
<222> LOCATION: (4)..(4)
<223> OTHER INFORMATION: Lys(HSG)-NH2

<400> SEQUENCE: 90

Phe Lys Tyr Lys
1

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
aatgcggcgg tggtgacagt a                                            21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aagctcagca cacagaaaga c                                            21

<210> SEQ ID NO 93
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 93
uaaaaucuuc cugcccacct t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 94
ggaagcuguu ggcugaaaat t                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aagaccagcc ucuuugccca g                                              21

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ggaccaggca gaaaacgag                                                 19

<210> SEQ ID NO 97
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cuaucaggau gacgcgg                                                   17

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
```
ugacacaggc aggcuugacu u                                          21

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggtgaagaag ggcgtccaa                                             19

<210> SEQ ID NO 100
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gatccgttgg agctgttggc gtagttcaag agactcgcca acagctccaa cttttggaaa    60

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aggtggtgtt aacagcagag                                            20

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aaggtggagc aagcggtgga g                                          21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
aaggagttga aggccgacaa a                                          21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

```
<400> SEQUENCE: 104
uauggagcug cagaggaugt t                                              21

<210> SEQ ID NO 105
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tttgaatatc tgtgctgaga acacagttct cagcacagat attctttt               49

<210> SEQ ID NO 106
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aatgagaaaa gcaaaaggtg ccctgtctc                                     29

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
aaucaucauc aagaaagggc a                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 108
augacuguca ggauguugct t                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gaacgaaucc ugaagacauc u                                              21

<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 110
aagcctggct acagcaatat gcctgtctc                                29

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 111
ugaccaucac cgaguuuaut t                                        21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aagtcggacg caacagagaa a                                        21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 113
cuaccuuucu acggacgugt t                                        21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ctgcctaagg cggatttgaa t                                        21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 115 ttauccuuc uucgggaagu c                                         21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
aaccttctgg aacccgccca c                                              21

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gagcatcttc gagcaagaa                                                 19

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
catgtggcac cgtttgcct                                                 19

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
aactaccaga aaggtatacc t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:
      Synthetic oligonucleotide

<400> SEQUENCE: 120
ucacaguguc cuuuauguat t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description Combined DNA/RNA Molecule:

```
            Synthetic oligonucleotide

<400> SEQUENCE: 121
gcaugaaccg gaggcccaut t                                              21

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ccggacagtt ccatgtata                                                 19

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Cys Ser Ser Ser Pro Ser Lys His Cys Gly
1               5                   10

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Phe Cys Ile Gly Arg Leu Cys Gly
1               5

<210> SEQ ID NO 125
<211> LENGTH: 12
<212> TYPE: PRT
<213> ORGANISM: Human immunodeficiency virus

<400> SEQUENCE: 125

Gly Arg Lys Lys Arg Arg Asn Arg Arg Arg Cys Gly
1               5                   10
```

What is claimed is:

1. A method of selecting the dosage of anti-CD22 antibody to be administered to a human patient with a B-cell malignancy comprising:
   a) exposing B cells from the human patient to a chimeric, humanized or human anti-CD22 antibody in vitro in the presence of cells selected from the group consisting of PBMCs (peripheral blood mononuclear cells), monocytes, NK cells, and granulocytes,
   b) measuring the depletion of one or more antigens selected from the group consisting of CD19, CD20, CD21, CD22 and CD79b on the surface of said B cells in vitro using a range of concentrations of the antibody, wherein the antigens are depleted by trogocytosis; and
   c) selecting a dosage of anti-CD22 antibody to be administered to the patient based on the concentrations of antibody effective to deplete the one or more antigens selected from the group consisting of CD19, CD20, CD21, CD22 and CD79b in vitro, wherein the dosage is capable of inducing trogocytosis of the one or more antigens from the patient's B cells.

2. The method of claim 1, wherein the amount of trogocytosis of the one or more antigens from the surface of B cells depends on the amount of anti-CD22 antibody to which the B cell is exposed.

3. The method of claim 1, wherein the anti-CD22 antibody is epratuzumab.

4. The method of claim 1, wherein the B-cell malignancy is selected from the group consisting of non-Hodgkin's lymphoma, B-cell acute and chronic lymphoid leukemias, Burkitt lymphoma, Hodgkin's lymphoma, hairy cell leukemia, multiple myeloma and Waldenstrom's macroglobulinemia.

5. The method of claim 1, wherein the anti-CD22 antibody is a naked antibody.

6. The method of claim 1, wherein the anti-CD22 antibody is a bispecific antibody that binds CD20 and CD 22.

7. The method of claim 1, further comprising measuring a response to the anti-CD22 antibody selected from the group consisting of (i) inducing phosphorylation of CD22, CD79a and CD79b; (ii) inducing translocation of CD22, CD79a and CD79b to lipid rafts; (iii) inducing caspase-dependent apoptosis; (iv) increasing pLyn, pERKs and pJNKs; (v) decreasing constitutively-active p38; and (vi) induce mitochondrial membrane depolarization, generation of reactive oxygen species, upregulation of pro-apoptotic Bax and downregulation of anti-apoptotic Bcl-xl, Mcl-1 and Bcl-2.

* * * * *